(12) United States Patent
Goetz et al.

(10) Patent No.: US 7,676,273 B2
(45) Date of Patent: Mar. 9, 2010

(54) STIMULATION TEMPLATES FOR PROGRAMMING A STIMULATION LEAD WITH COMPLEX ELECTRODE ARRAY GEOMETRY

(75) Inventors: Steven M. Goetz, Brooklyn Center, MN (US); Richard T. Stone, Minneapolis, MN (US); Warren W. Ball, Coon Rapids, MN (US); Carl D. Wahlstrand, Columbia Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 574 days.

(21) Appl. No.: 11/591,189

(22) Filed: Oct. 31, 2006

(65) Prior Publication Data
US 2007/0203542 A1 Aug. 30, 2007

Related U.S. Application Data

(60) Provisional application No. 60/776,454, filed on Feb. 24, 2006, provisional application No. 60/785,181, filed on Mar. 23, 2006.

(51) Int. Cl.
*A61N 1/00* (2006.01)
(52) U.S. Cl. .................................................. 607/62
(58) Field of Classification Search .............. 607/59–62
See application file for complete search history.

(56) References Cited

U.S. PATENT DOCUMENTS

| 4,328,809 A | 5/1982 | Hirschowitz et al. |
| 4,735,204 A | 4/1988 | Sussman et al. |
| 4,793,353 A | 12/1988 | Borkan |
| 5,370,672 A | 12/1994 | Fowler et al. |
| 5,443,486 A | 8/1995 | Hrdlicka et al. |
| 5,626,629 A | 5/1997 | Faltys et al. |
| 5,643,330 A | 7/1997 | Holsheimer et al. |
| 5,724,985 A | 3/1998 | Snell et al. |

(Continued)

FOREIGN PATENT DOCUMENTS

EP 0811395 12/1997

(Continued)

OTHER PUBLICATIONS

Honeywell Inc. Systems and Research Division Research Department, "Experimental Evaluation of Symbolic and Pictorial Displays for Submarine Control," U.S. Dept. of Commerce Nat'l Technical Info. Service, Sep. 1965.

(Continued)

*Primary Examiner*—George Manuel
(74) *Attorney, Agent, or Firm*—Shumaker & Sieffert, P.A.

(57) ABSTRACT

The disclosure is directed to programming implantable stimulators to deliver stimulation energy via one or more implantable leads having complex electrode array geometries. A user interface of a programmer allows a user to define stimulation therapy by interacting with one or more representations of the lead that delivers the therapy. The disclosure also contemplates selecting stimulation parameters to satisfy a user defined stimulation field by selecting one or more volumetric stimulation templates that best fit the stimulation field. The user interface may display the stimulation templates in relation to different perspectives of a lead and the stimulation field. Use of stimulation templates may simplify the determination of stimulation parameters in response to any of a variety of types of user definition of a stimulation field.

34 Claims, 48 Drawing Sheets

U.S. PATENT DOCUMENTS

| | | | |
|---|---|---|---|
| 5,740,037 A | 4/1998 | McCann et al. | |
| 5,769,875 A | 6/1998 | Peckham | |
| 5,776,171 A | 7/1998 | Peckham | |
| 5,893,883 A | 4/1999 | Torgerson et al. | |
| 5,895,416 A | 4/1999 | Barreras et al. | |
| 5,938,690 A | 8/1999 | Law et al. | |
| 5,954,758 A | 9/1999 | Peckham | |
| 5,983,140 A | 11/1999 | Smith et al. | |
| 6,004,276 A | 12/1999 | Wright et al. | |
| 6,026,328 A | 2/2000 | Peckham | |
| 6,027,456 A | 2/2000 | Feler et al. | |
| 6,052,624 A | 4/2000 | Mann | |
| 6,077,223 A | 6/2000 | Satherley | |
| 6,099,479 A | 8/2000 | Christopherson et al. | |
| 6,106,464 A | 8/2000 | Bass et al. | |
| 6,120,467 A | 9/2000 | Scallhorn | |
| 6,163,725 A | 12/2000 | Peckham | |
| 6,208,894 B1 | 3/2001 | Schulman et al. | |
| 6,249,703 B1 | 6/2001 | Stanton et al. | |
| 6,289,247 B1 | 9/2001 | Faltys et al. | |
| 6,308,102 B1 | 10/2001 | Sieracki et al. | |
| 6,358,245 B1* | 3/2002 | Edwards et al. | 606/34 |
| 6,381,496 B1 | 4/2002 | Meadows et al. | |
| 6,393,325 B1* | 5/2002 | Mann et al. | 607/46 |
| 6,477,424 B1 | 11/2002 | Thompson et al. | |
| 6,564,104 B2 | 5/2003 | Nelson et al. | |
| 6,574,503 B2 | 6/2003 | Ferek-Petric | |
| 6,587,724 B2 | 7/2003 | Mann | |
| 6,609,031 B1 | 8/2003 | Law et al. | |
| 6,609,032 B1 | 8/2003 | Woods et al. | |
| 6,622,048 B1* | 9/2003 | Mann et al. | 607/46 |
| 6,659,968 B1 | 12/2003 | McClure | |
| 6,748,276 B1 | 6/2004 | Daignault, Jr. et al. | |
| 6,873,872 B2 | 3/2005 | Gluckman et al. | |
| 7,003,349 B1 | 2/2006 | Andersson et al. | |
| 7,033,326 B1 | 4/2006 | Pianca et al. | |
| 7,035,690 B2 | 4/2006 | Goetz | |
| 7,065,412 B2 | 6/2006 | Swoyer et al. | |
| 7,184,837 B2 | 2/2007 | Goetz | |
| 7,252,090 B2 | 8/2007 | Goetz | |
| 7,266,412 B2 | 9/2007 | Stypulkowski | |
| 2001/0007950 A1 | 7/2001 | North et al. | |
| 2001/0031919 A1 | 10/2001 | Strommer et al. | |
| 2002/0038137 A1 | 3/2002 | Stein | |
| 2002/0044059 A1 | 4/2002 | Reeder et al. | |
| 2002/0065686 A1 | 5/2002 | Monteleone et al. | |
| 2002/0072785 A1 | 6/2002 | Nelson et al. | |
| 2002/0095098 A1 | 7/2002 | Marinello | |
| 2002/0103512 A1 | 8/2002 | Echauz et al. | |
| 2002/0116036 A1 | 8/2002 | Daignault | |
| 2002/0120188 A1 | 8/2002 | Brock et al. | |
| 2003/0040291 A1 | 2/2003 | Brewer | |
| 2003/0158587 A1 | 8/2003 | Esteller et al. | |
| 2003/0171789 A1 | 9/2003 | Malek et al. | |
| 2003/0174066 A1 | 9/2003 | Goetz et al. | |
| 2003/0174069 A1 | 9/2003 | Goetz et al. | |
| 2003/0176906 A1 | 9/2003 | Lee | |
| 2004/0034394 A1 | 2/2004 | Woods et al. | |
| 2004/0059395 A1 | 3/2004 | North | |
| 2004/0098063 A1* | 5/2004 | Goetz | 607/48 |
| 2005/0070781 A1 | 3/2005 | Dawant et al. | |
| 2005/0267347 A1 | 12/2005 | Oster | |
| 2006/0017749 A1* | 1/2006 | McIntyre et al. | 345/664 |
| 2006/0094951 A1 | 5/2006 | Dean et al. | |
| 2006/0155333 A1 | 7/2006 | Goetz | |
| 2006/0229687 A1 | 10/2006 | Goetz et al. | |
| 2007/0055322 A1 | 3/2007 | Forsberg et al. | |
| 2008/0215125 A1 | 9/2008 | Farah et al. | |

FOREIGN PATENT DOCUMENTS

| | | |
|---|---|---|
| EP | 1134003 | 9/2001 |
| EP | 0939661 B1 | 8/2002 |
| WO | WO 92/17240 | 10/1992 |
| WO | WO 98/43701 | 10/1998 |
| WO | WO 99/56820 | 11/1999 |
| WO | WO 00/02623 | 1/2000 |
| WO | WO 01/39831 | 6/2001 |
| WO | WO 01/43818 | 6/2001 |
| WO | WO 01/47411 | 7/2001 |
| WO | WO 01/80732 | 11/2001 |
| WO | WO 01/83028 | 11/2001 |
| WO | WO 01/93952 | 12/2001 |
| WO | WO 01/93953 | 12/2001 |
| WO | WO 02/01387 | 1/2002 |
| WO | WO 02/34331 | 5/2002 |
| WO | WO 02/39250 | 5/2002 |
| WO | WO 02/47760 | 6/2002 |
| WO | WO 02/49500 | 6/2002 |
| WO | WO 03/037430 | 5/2003 |
| WO | WO 03/077993 | 9/2003 |
| WO | WO 03/077995 | 9/2003 |

OTHER PUBLICATIONS

Notification of Transmittal of the International Preliminary Report on Patentablity for patent application No. PCT/US2007/002021, mailed Mar. 28, 2008, (8 pages).

Notification of Transmittal of the International Preliminary Report on Patentablity for patent application No. PCT/US2007/002048, mailed Apr. 16, 2008, (7 pages).

Notification of Transmittal of the International Preliminary Report on Patentablity for patent application No. PCT/US2007/002019, mailed Apr. 16, 2008, (5 pages).

Notification of Transmittal of the International Preliminary Report on Patentablity for patent application No. PCT/US2007/002047, mailed Apr. 18, 2008, (8 pages).

Notification of Transmittal of the International Preliminary Report on Patentablity for patent application No. PCT/US2007/001810, mailed Apr. 4, 2008, (8 pages).

Notification of Transmittal of the International Preliminary Report on Patentablity for patent application No. PCT/US2007/001811, mailed Apr. 16, 2008, (5 pages).

Notification of Transmittal of the International Preliminary Report on Patentablity for patent application No. PCT/US2007/001808, mailed Apr. 18, 2008, (5 pages).

Notification of Transmittal of the International Preliminary Report on Patentablity for patent application No. PCT/US2007/001807, mailed Apr. 18, 2008, (5 pages).

Notification of Transmittal of the International Preliminary Report on Patentablity for corresponding patent application No. PCT/US2007/002049, mailed Apr. 9, 2008, (7 pages).

Notification of Transmittal of the International Preliminary Report on Patentablity for patent application No. PCT/US2007/002022, mailed Mar. 7, 2008, (9 pages).

Advanced Neuromodulation Systems Renew Neurostimulation Systems User's Guide, Oct. 1997 (52 pages).

Advanced Neuromodulation Systems PainDoc® Operator's Manual, 2002 (59 pages).

Medtronic MEMORYMOD® Model 7459 Software Programming Guide for Synergy™ and Itrel® 3 Neurostimulation Systems, 1999 (211 pgs.).

International Search Report from PCT Application Serial No. PCT/US03/35883 dated Apr. 14, 2004 (3 pages).

International Preliminary Examination Report from PCT Application Serial No. PCT/US03/35883 dated Nov. 19, 2004 (6 pages).

Office Action for U.S. Appl. No. 11/371,868, mailed May 2, 2008, 12 pages.

U.S. Appl. No. 11/371,868, entitled "Human-Implantable Neurostimulator User Interface Having Multiple Levels of Abstraction", filed Mar. 9, 2006, Steven M. Goetz.

Notification of Transmittal of the International Search Report and the Written Opinion of the International Searching Authority for patent application No. PCT/US2007/001811, filed Jan. 24, 2007, (9 pages).
Notification of Transmittal of the International Search Report and the Written Opinion of the International Searching Authority for patent application No. PCT/US2007/001808, filed Jan. 24, 2007, (9 pages).
Notification of Transmittal of the International Search Report and the Written Opinion of the International Searching Authority for patent application No. PCT/US2007/001807, filed Jan. 24, 2007, (9 pages).
Notification of Transmittal of the International Search Report and the Written Opinion of the International Searching Authority for corresponding patent application No. PCT/US2007/002049, filed Jan. 24, 2007, (9 pages).
Notification of Transmittal of the International Search Report and the Written Opinion of the International Searching Authority for patent application No. PCT/US2007/002022, filed Jan. 24, 2007, (9 pages).
Office Action for U.S. Appl. No. 11/591,176, dated Apr. 6, 2009, 11 pages.
Office Action for U.S. Appl. No. 11/591,281, dated Apr. 6, 2009, 12 pages.
Office Action for U.S. Appl. No. 11/591,178, dated Apr. 6, 2009, 13 pages.
Office Action for U.S. Appl. No. 11/591,193, dated Apr. 6, 2009, 9 pages.
Office Action for U.S. Appl. No. 11/591,188, dated Apr. 6, 2009, 9 pages.
Office Action for U.S. Appl. No. 11/591,280, dated Apr. 6, 2009, 9 pages.
Office Action for U.S. Appl. No. 11/591,170, dated Mar. 20, 2009, 7 pages.
Office Action for U.S. Appl. No. 11/591,187, dated Apr. 6, 2009, 12 pages.
European Office Action for European Application No. 07 709 862.2-2305, dated Feb. 19, 2009, 2 pages.
Response to European Office Action for European Application No. 07 709 862.2-2305, dated Jun. 29, 2009, 6 pages.
European Office Action for European Application No. 07 717 004.1-2305, dated Feb. 18, 2009, 2 pages.
Response to European Office Action for European Application No. 07 717 004.1-2305, dated Jun. 29, 2009, 6 pages.
European Office Action for European Application No. 07 749 226.2-2305, dated Feb. 18, 2009, 2 pages.
Response to European Office Action for European Application No. 07 749 226.2-2305, dated Jun. 29, 2009, 6 pages.
European Office Action for European Application No. 07 716 942.3-2305, dated Feb. 18, 2009, 2 pages.
Response to European Office Action for European Application No. 07 716 942.3-2305, dated Jun. 17, 2009, 6 pages.
Responsive Amendment for U.S. Appl. No. 11/591,176, filed Jun. 30, 2009, 13 pages.
Responsive Amendment for U.S. Appl. No. 11/591,281, filed Jun. 18, 2009, 18 pages.
Responsive Amendment for U.S. Appl. No. 11/591,178, filed Jun. 30, 2009, 21 pages.
Responsive Amendment for U.S. Appl. No. 11/591,193, filed Jun. 18, 2009, 15 pages.
Responsive Amendment for U.S. Appl. No. 11/591,188, filed Jun. 12, 2009, 10 pages.
Responsive Amendment for U.S. Appl. No. 11/591,280, filed Jun. 30, 2009, 21 pages.
Response for U.S. Appl. No. 11/591,170, filed May 12, 2009, 8 pages.
Responsive Amendment for U.S. Appl. No. 11/591,187, filed Jul. 1, 2009, 23 pages.
Responsive Amendment for U.S. Appl. No. 11/371,868, filed Aug. 19, 2008, 13 pages.
Office Action for U.S. Appl. No. 11/371,868, dated Nov. 28, 2008, 8 pages.
Response for U.S. Appl. No. 11/371,868, filed Jan. 27, 2009, 5 pages.
Advisory Action for U.S. Appl. No. 11/371,868, dated Feb. 25, 2009, 3 pages.
Responsive Amendment for U.S. Appl. No. 11/371,868, filed Apr. 28, 2009, 14 pages.
Final Office Action for U.S. Appl. No. 11/591,281, mailed Aug. 25, 2009, 13 pages.
Responsive Amendment for U.S. Appl. No. 11/591,281, filed Oct. 22, 2009, 18 pages.
Office Action for U.S. Appl. No. 11/591,299, mailed Jul. 14, 2009, 10 pages.
Responsive Amendment for U.S. Appl. No. 11/591,299, filed Oct. 14, 2009, 16 pages.
Final Office Action for U.S. Appl. No. 11/591,193, mailed Oct. 6, 2009, 8 pages.

* cited by examiner

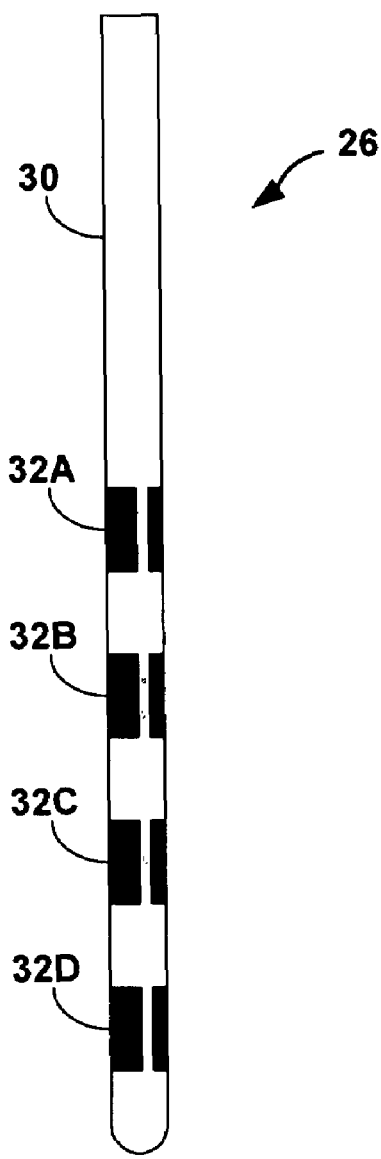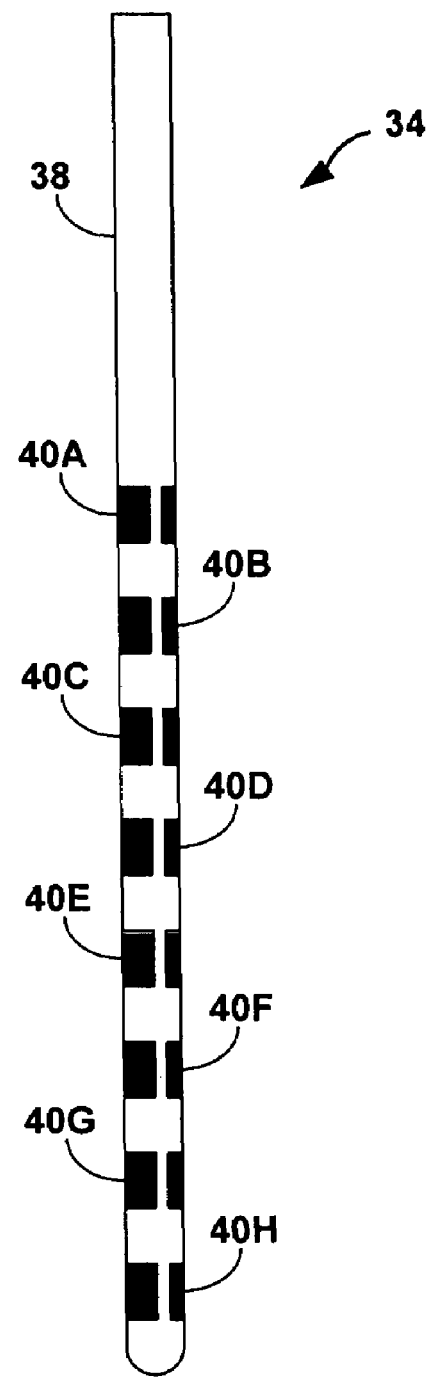
FIG. 2A
FIG. 2B

| + | + | + | + |
|---|---|---|---|
| - | - | - | - |
| 3A | 3B | 3C | 3D |
| 4A | 4B | 4C | 4D |

FIG. 27A

| 1A | 1B | 1C | 1D |
|---|---|---|---|
| + | + | + | + |
| - | - | - | - |
| 4A | 4B | 4C | 4D |

FIG. 27B

| 1A | 1B | 1C | 1D |
|---|---|---|---|
| 2A | 2B | 2C | 2D |
| + | + | + | + |
| - | - | - | - |

FIG. 27C

| 1A | 1B | 1C | 1D |
|---|---|---|---|
| + | 2B | 2C | 2D |
| - | 3B | 3C | 3D |
| 4A | 4B | 4C | 4D |

FIG. 27D

| 1A | 1B | 1C | 1D |
|---|---|---|---|
| 2A | + | 2C | 2D |
| 3A | - | 3C | 3D |
| 4A | 4B | 4C | 4D |

FIG. 27E

| 1A | 1B | 1C | 1D |
|---|---|---|---|
| 2A | 2B | + | 2D |
| 3A | 3B | - | 3D |
| 4A | 4B | 4C | 4D |

FIG. 27F

| 1A | 1B | 1C | 1D |
|----|----|----|----|
| 2A | -  | +  | 2D |
| 3A | 3B | -  | 3D |
| 4A | 4B | 4C | 4D |

FIG. 28A

| 1A | 1B | 1C | 1D |
|----|----|----|----|
| 2A | 2B | +  | 2D |
| 3A | -  | -  | 3D |
| 4A | 4B | 4C | 4D |

FIG. 28B

| 1A | 1B | 1C | 1D |
|----|----|----|----|
| 2A | 2B | +  | -  |
| 3A | 3B | -  | 3D |
| 4A | 4B | 4C | 4D |

FIG. 28C

| 1A | 1B | -  | 1D |
|----|----|----|----|
| 2A | 2B | +  | -  |
| 3A | 3B | 3C | 3D |
| 4A | 4B | 4C | 4D |

FIG. 28D

| 1A | 1B | -  | 1D |
|----|----|----|----|
| 2A | -  | +  | 2D |
| 3A | 3B | 3C | 3D |
| 4A | 4B | 4C | 4D |

FIG. 28E

| 1A | 1B | 1C | 1D |
|----|----|----|----|
| 2A | 2B | 2C | 2D |
| 3A | -  | +  | 3D |
| 4A | 4B | -  | 4D |

FIG. 28F

STIMULATION TEMPLATES FOR PROGRAMMING A STIMULATION LEAD WITH COMPLEX ELECTRODE ARRAY GEOMETRY

This application claims the benefit of U.S. provisional application No. 60/776,454, filed Feb. 24, 2006, and U.S. provisional application No. 60/785,181, filed Mar. 23, 2006. The entire content of both provisional applications is incorporated herein by reference.

TECHNICAL FIELD

The invention relates to electrical stimulation therapy and, more particularly, to selection of electrode combinations for delivery of stimulation therapy to a patient.

BACKGROUND

Implantable electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more leads that include electrodes located proximate to target locations associated with the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

In general, a physician selects values for a number of programmable parameters in order to define the electrical stimulation therapy to be delivered by the implantable stimulator to a patient. For example, the physician ordinarily selects a combination of electrodes carried by one or more implantable leads, and assigns polarities to the selected electrodes. In addition, the physician selects an amplitude, which may be a current or voltage amplitude, a pulse width and a pulse rate for stimulation pulses to be delivered to the patient. A group of parameters, including electrode combination, electrode polarity, amplitude, pulse width and pulse rate, may be referred to as a program in the sense that they drive the neurostimulation therapy to be delivered to the patient. In some applications, an implantable stimulator may deliver stimulation therapy according to multiple programs either simultaneously or on a time-interleaved, overlapping or non-overlapping, basis.

The process of selecting electrode combinations and other parameters can be time consuming, and may require a great deal of trial and error before a therapeutic program is discovered. The "best" program may be a program that best balances greater clinical efficacy and minimal side effects experienced by the patient. In addition, some programs may consume less power during therapy. The physician typically needs to test a large number of possible electrode combinations within the electrode set implanted in the patient, in order to identify an optimal combination of electrodes and associated polarities. As mentioned previously, an electrode combination is a selected subset of one or more electrodes located on one or more implantable leads coupled to an implantable neurostimulator. As a portion of the overall parameter selection process, the process of selecting electrodes and the polarities of the electrodes can be particularly time-consuming and tedious.

The physician may test electrode combinations by manually specifying combinations based on intuition or some idiosyncratic methodology. The physician may then record notes on the efficacy and side effects of each combination after delivery of stimulation via that combination. In some cases, efficacy can be observed immediately within the clinic. For example, spinal cord stimulation may produce parasthesia and side effects that can be observed by the physician based on patient feedback. In other cases, side effects and efficacy may not be apparent until a program has been applied for an extended period of time, as is sometimes the case in deep brain stimulation. Upon receipt of patient feedback and/or observation of symptoms by the physician, the physician is able to compare and select from the tested programs.

In order to improve the efficacy of neurostimulation therapy, electrical stimulators have grown in capability and complexity. Modern neurostimulators tend to have larger numbers of electrode combinations, larger parameter ranges, and the ability to simultaneously deliver multiple therapy configurations by interleaving stimulation pulses in time. Although these factors increase the physician's ability to adjust therapy for a particular patient or disease state, the burden involved in optimizing the device parameters has similarly increased. Unfortunately, fixed reimbursement schedules and scarce clinic time present challenges to effective programming of neurostimulator therapy.

Existing lead sets include axial leads carrying ring electrodes disposed at different axial positions, and so-called "paddle" leads carrying planar arrays of electrodes. Selection of electrode combinations within an axial lead, a paddle lead, or among two or more different leads presents a challenge to the physician. The emergence of more complex electrode array geometries presents still further challenges. The design of the user interface used to program the implantable neurostimulator, in the form of either a physician programmer or patient programmer, has a great impact on the ability to efficiently define and select efficacious stimulation programs.

SUMMARY

In general, the disclosure is directed to techniques for programming implantable stimulators to deliver stimulation energy via one or more implantable leads having complex electrode array geometries. The techniques may be applied to a programming interface associated with a clinician programmer, a patient programmer, or both. In addition, the disclosure contemplates techniques for guided programming to select electrode combinations and parameter values to support therapeutic efficacy.

The disclosure contemplates selecting electrode combinations according to a user defined stimulation field by selecting one or more stimulation templates that best fit the stimulation field. The user interface may display the stimulation templates set in relation to different perspectives of a lead and the stimulation field. Use of stimulation templates may simplify the determination of stimulation parameters in response to any of a variety of types of user definition of a stimulation field, such as drawing a representation of a stimulation field or modifying a previously displayed representation of a stimulation field.

A user may also be able to select electrode combinations within a complex electrode array geometry, in accordance with this disclosure, a user interface permits a user to view electrodes from different perspectives relative to the lead. For example, the user interface may provide an axial perspective of a lead and a cross-sectional perspective of the lead. In addition, the user interface may include an axial control medium to select and/or view electrodes at different positions along the length of a lead from the axial perspective, and a rotational control medium to select and/or view electrodes at different angular positions around a circumference of the lead from the cross-sectional perspective.

A complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead. Another example of a simple electrode array geometry is a planar array of electrodes on a paddle lead.

An example of a complex electrode array geometry, in accordance with this disclosure, is an array of electrodes positioned at different axial positions along the length of a lead, as well as at different angular positions about the circumference of the lead. In some embodiments, the electrodes in the complex array geometry may appear similar to non-contiguous, arc-like segments of a conventional ring electrode. A lead with a complex electrode array geometry may include multiple rings of electrode segments. Each ring is disposed at a different axial position. Each electrode segment within a given ring is disposed at a different angular position. The lead may be cylindrical or have a circular cross-section of varying diameter. Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section.

An electrode combination is a selected subset of one or more electrodes located on one or more implantable leads coupled to an implantable stimulator. The electrode combination also refers to the polarities of the electrodes in the selected subset. The electrode combination, electrode polarities, amplitude, pulse width and pulse rate together define a program for delivery of electrical stimulation therapy by an implantable stimulator via an implantable lead or leads.

A user interface that permits a user to view electrodes from different perspectives relative to the lead and/or actuate both axial and rotation control media to select or view electrodes can facilitate efficient evaluation, selection and programming of electrode combinations and stimulation programs including the electrode combinations. In some embodiments, the user interface may support automated guidance techniques that permit guided selection of electrode combinations and parameters, e.g., pursuant to a predetermined or dynamically created sequence of electrode combinations to be evaluated.

The user interface also may present, on a selective basis, an electrode view or a field view of the lead or leads. The electrode view or field view may present one or multiple perspectives such as axial and cross-sectional perspectives of a lead. In the electrode view, the user selects individual electrodes to form an electrode combination, and specifies parameters for stimulation delivered via the electrode combination. In a field view, the user manipulates a representation of an electrical stimulation field produced by a selected electrode combination. For example, the user may change the size, shape or position of the field using graphical input media such as cursor or stylus control.

For example, in the field view, the user may perform various field manipulation operations such as a grow/shrink operation to expand or contract the size of a field, a spread/focus operation to expand or contract the number of electrodes included in an electrode combination, and a split/merge operation to divide a single electrode combination into multiple combinations or vice versa. In response to such operations, a programmer selects appropriate electrode combinations, polarities, amplitudes, pulse widths, and pulse rates sufficient to support the specified operation.

The techniques described herein may be used during a test or evaluation mode to select different electrode combinations in an effort to identify efficacious electrode combinations. Additionally, the techniques may be used to select different electrode combinations associated with different stimulation programs during an operational mode, either directly or by selection of programs including such electrode combinations. For example, the techniques and associated user interfaces may be implemented in a clinician programmer used by a clinician to program a stimulator, in a patient programmer used by a patient to program or control a stimulator, or in an external stimulator including both pulse generation and programming functionality.

In one embodiment, the disclosure provides a method that includes-presenting on a display at least one view of a representation of an implantable lead having a complex electrode array geometry, receiving user input defining a stimulation field on the representation of the lead, selecting at least one volumetric stimulation template from a memory based on the stimulation field, and selecting an electrical stimulation parameter set associated with the selected volumetric stimulation template in the memory.

In another embodiment, the disclosure provides a system that includes a programmer having a user interface that displays at least one view of a representation of an implantable lead having a complex electrode array geometry, and receives user input defining at least one stimulation field on the representation of the lead, a memory that stores a plurality of volumetric stimulation templates, and a processor that selects at least one of the plurality of stimulation templates based on the at least one user-defined stimulation field and selects an electrical stimulation parameter set associated with the selected volumetric stimulation template in the memory.

In an additional embodiment, the disclosure provides a computer-readable medium including instructions to cause a processor to present on a display at least one view of a representation of an implantable lead having a complex electrode array geometry, receive user input defining a stimulation field on the representation of the lead, select at least one volumetric stimulation template from a memory based on the stimulation field, and select an electrical stimulation parameter set associated with the selected volumetric stimulation template in the memory.

The disclosure may provide one or more advantages. For example, the programmer may more quickly select the best one or more stimulation templates that fit a user-defined stimulation field instead of generating stimulation parameters every time the user changes the desired field. In addition, the user interface may present the stimulation template set to the user with respect to the represented lead and the defined stimulation field. In this manner, the user may easily review the effect of parameters that will be used to deliver therapy and change them if necessary. The user interface represents the complex electrode array geometry with multiple views that allow the user to view the lead in a two-dimensional display.

The details of one or more embodiments of the invention are set forth in the accompanying drawings and the descrip-

BRIEF DESCRIPTION OF DRAWINGS

FIGS. 2A and 2B are conceptual diagrams illustrating two different implantable stimulation leads.

FIGS. 27 and 28 are diagrams illustrating selection of different electrode combinations on a lead having a complex electrode array geometry.

DETAILED DESCRIPTION

Figure 1:
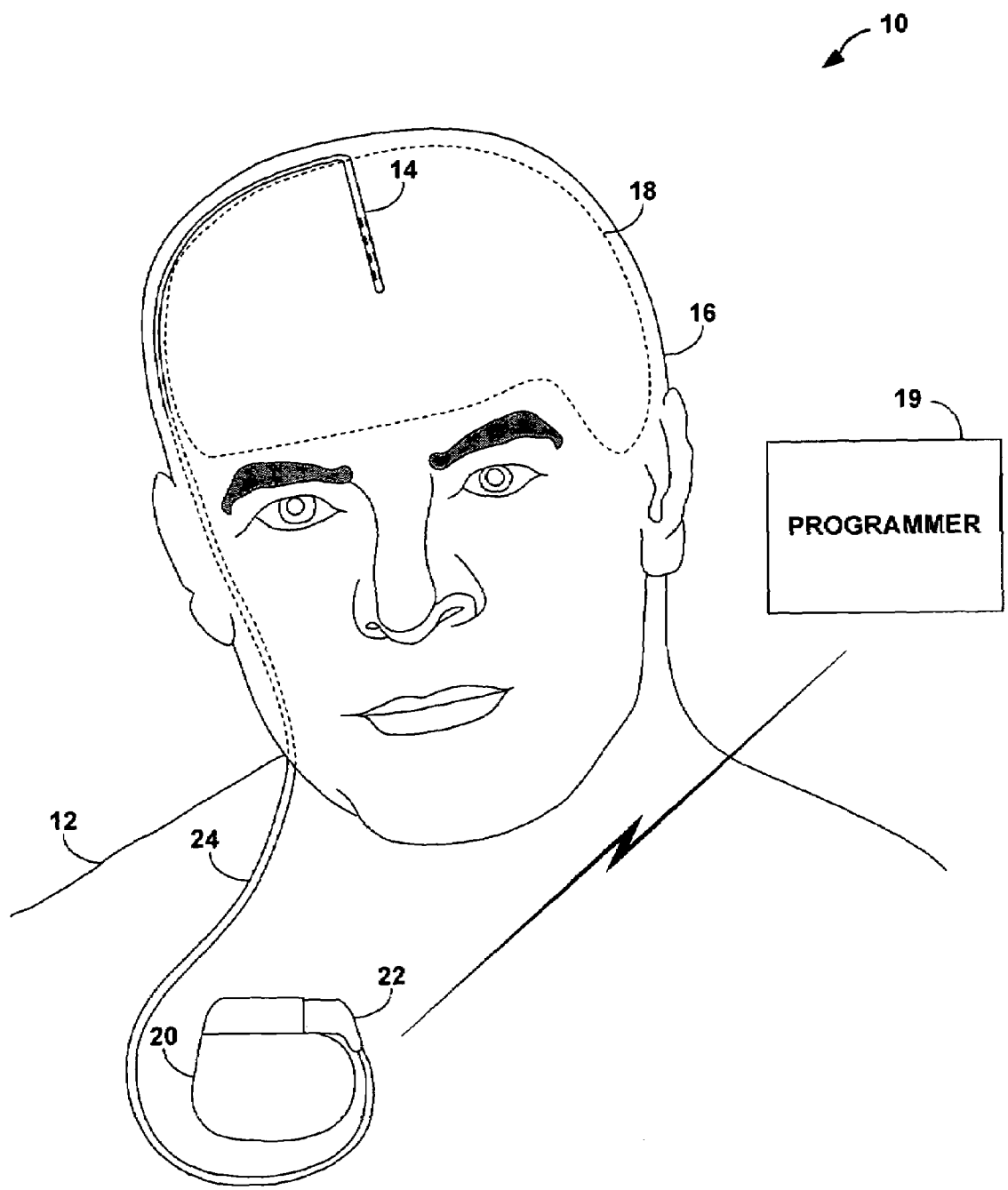
FIG. 1 is a conceptual diagram illustrating an example stimulation system with a stimulation lead implanted in the brain of a patient.

Electrical stimulation therapy may provide relief to a patient from many conditions. However, the stimulation therapy efficacy is contingent on a physician, or clinician, correctly configuring, or programming, the stimulation parameters in a manner that provides therapy to the patient while minimizing side-effects produced from the stimulation. Efficacy may be judged in terms of the extent to which therapy relieves symptoms or a disorder or disease, in combination with the absence of undesirable side effects. Due to physiological diversity, different disease states, and inaccuracies in stimulation lead placement, the parameters may vary greatly between patients. Therefore, the physician must individually program stimulation parameters for each patient. This programming process may continue throughout the therapy as patient needs change.

Implanting stimulation leads with complex electrode array geometries introduces more complex programming challenges for the physician. Although leads with complex electrode array geometries provide greater flexibility in defining a stimulation field to provide therapy, the physician must identify effective electrodes, electrode polarity, current and voltage amplitudes, pulse widths, and pulse frequencies for electrode combination at different axial and angular positions. Physicians may prefer to focus on stimulating a particular anatomical structure or target tissue of the patient, which becomes difficult when facing potentially millions of programming options presented by a complex electrode array geometry.

A complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead. Another example of a simple electrode array geometry is a planar array of electrodes on a paddle lead.

An example of a complex electrode array geometry, in accordance with this disclosure, is an array of electrodes positioned at different axial positions along the length of a lead, as well as at different angular positions about the circumference of the lead. In some embodiments, the electrodes in the complex array geometry may appear similar to non-contiguous, arc-like segments of a conventional ring electrode. A lead with a complex electrode array geometry may include multiple rings of electrode segments. Each ring is disposed at a different axial position. Each electrode segment within a given ring is disposed at a different angular position. The lead may be cylindrical or have a circular cross-section of varying diameter.

Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section in a plane transverse to the longitudinal axis of the lead. As further examples, electrodes may be arranged at different axial and angular positions on leads defining spherical, hemispherical or generally rounded surfaces. Leads with complex electrode array geometries may have a defined shape or be at least partially conformable to an anatomical structure.

An electrode combination is a selected subset of one or more electrodes located on one or more implantable leads coupled to an implantable stimulator. The electrode combination also refers to the polarities of the electrode segments in the selected subset. The electrode combination, electrode polarities, amplitude, pulse width and pulse rate together define a program for delivery of electrical stimulation therapy by an implantable stimulator via an implantable lead or leads. By selecting particular electrode combinations, a physician can target particular anatomic structures. By selecting values for amplitude, pulse width and pulse rate, the physician can attempt to optimize the electrical therapy delivered to the patient via the selected electrode combination or combinations.

This disclosure is directed to techniques for programming implantable stimulators to deliver stimulation energy via one or more implantable leads having complex electrode array geometries. The techniques may be applied to a programming interface associated with a physician programmer, a patient programmer, or both. In addition, the disclosure contemplates techniques for guided programming to select electrode combinations and parameter values to support therapeutic efficacy. For example, the user interface may support automated guidance techniques that permit guided selection of electrode combinations and parameters, e.g., pursuant to a predetermined or dynamically created sequence of electrode combinations to be evaluated.

To select electrode combinations within a complex electrode array geometry, in accordance with this disclosure, a user interface permits a user to view electrodes from different perspectives relative to the lead. For example, the user interface may provide an axial perspective of a lead, and a cross-sectional perspective of the lead in a plane transverse to a longitudinal axis of the lead. In addition, the user interface may include an axial control medium to select and/or view electrodes at different positions along the length of a lead from the axial perspective, and a rotational or translational control medium to select and/or view electrodes at different angular positions around a circumference of the lead from the cross-sectional perspective The user interface also may present, on a selective basis, an electrode view or a field view of the lead or leads. The electrode view or field view may present one or multiple perspectives such as axial and cross-sectional perspectives of a lead. In the electrode view, the user selects individual electrodes to form an electrode combination, and specifies parameters for stimulation delivered via the electrode combination. In a field view, the user manipulates a representation of an electrical stimulation field produced by a selected electrode combination. For example, the user may change the size, shape or position of the field using graphical input media such as cursor or stylus control.

In the field view, the user may perform various field manipulation operations such as a grow/shrink operation to expand or contract the size of a field, a spread/focus operation to expand or contract the number of electrodes included in an electrode combination, and a split/merge operation to divide a single electrode combination into multiple combinations or vice versa. In response to such operations, a programmer selects appropriate electrode combinations, polarities, amplitudes, pulse widths, and pulse rates sufficient to support the specified operation.

In some embodiments, the electrode view may permit a user to select individual electrodes from either an axial or cross-sectional perspective. The user may use a combination of axial and rotational or translational input media to select individual electrodes or electrode combinations, move an electrode combination up or down along the axial length of the lead, or rotate or translate an electrode combination around the circumference of the lead. Likewise, the field view may permit a user to manipulate fields from either an axial or cross-sectional perspective. For example, the user may expand a field by manipulating an axial field representation or a cross-sectional field representation.

In other embodiments, the programmer may automatically generate stimulation parameters that best fit a defined stimulation field created by the user instead of manual electrode selection. One method of generating the stimulation parameters may include creating a stimulation template set from a plurality of stored volumetric stimulation templates which best fit a stimulation field that the user defined. The template set is representative of stimulation parameters that will govern the stimulation therapy, and may be shown by the programmer in relation to the stimulation field. The process of generating stimulation parameters from the stimulation field may be simplified through the selection of a stimulation template, and the user may benefit by being shown the best therapy that can be delivered from the defined stimulation field.

Further, in some embodiments, the field view of the stimulation parameters may be specific to patient 12 instead of utilizing generic tissue characteristics. The programmer may generate an electrical field model according to the stimulation parameters, e.g., determined based on a user-defined stimulation field, and patient anatomy data stored in the programmer. The patient anatomy data may indicate one or more characteristics of patient tissue proximate to an implanted lead created from any type of imaging modality, e.g., computed tomography, magnetic resonance imaging, etc. The resulting electrical field may be presented by the programmer in relation to one or more views of the lead. The electrical field illustrates to the user what the electrical propagation through the tissue would look like in contrast to the user-defined stimulation field. In addition, the programmer may apply a neuron model that indicates one or more characteristics of patient neural tissue proximate to an implanted lead to the electrical field model to generate an activation field model of the stimulation therapy defined by the stimulation field. The activation field model illustrates the actual neurons that will be activated by the electrical field. Similar to the electrical field model, the activation field model may be presented to the user by the programmer over the appropriate location of the displayed lead. The user may also modify the stimulation field based upon the activation field model or simply alter the activation field model to create the desired therapy.

The techniques described herein may be used during a test or evaluation mode to select different electrode segment combinations in an effort to identify efficacious electrode combinations. Additionally, the techniques may be used to select different electrode combinations associated with different stimulation programs during an operational mode, either directly or by selection of programs including such electrode combinations. For example, the techniques and associated user interfaces may be implemented in a physician programmer used by a physician to program a stimulator, in a patient programmer used by a patient to program or control a stimulator, or in an external stimulator including both pulse generation and programming functionality. As a further alternative, the programming techniques described herein are not necessarily limited to use with implantable stimulators, and may be used in conjunction with external stimulators that deliver stimulation, e.g., via percutaneous leads.

FIG. 1 is a conceptual diagram illustrating an example stimulation system with a stimulation lead implanted in the brain of a patient. As shown in FIG. 1, stimulation system 10 includes implantable stimulator 20, lead plug 22, lead wire 24 and lead 14 implanted within patient 12. Specifically, lead 14 enters through cranium 16, e.g., via a burr hole cap, and is implanted within brain 18 to deliver deep brain stimulation (DBS). One or more electrodes of lead 14 provide electrical pulses to surrounding anatomical regions of brain 18 in a therapy that may alleviate a condition of patient 12. In some embodiments, more than one lead 14 may be implanted within brain 18 of patient 12 to stimulate multiple anatomical regions of the brain. An external programmer 19 may be provided in the form of a handheld device, portable computer, or workstation that provides a user interface to a physician or patient. The physician or patient interacts with the user interface to program stimulation parameters for implantable stimulator 20, or a neurostimulator, via external programmer 19.

Although application of implantable stimulator 20 to DBS is depicted in FIG. 1, implantable electrical stimulators incorporating one or more leads with complex electrode array geometries may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. For example, stimulation may be delivered via complex electrode array geometries to serve different therapeutic applications, such as deep brain stimulation (DBS), spinal cord stimulation (SCS), pelvic stimulation, gastric stimulation, or peripheral nerve stimulation. Stimulation via complex electrode array geometries also may be used for muscle stimulation, e.g., functional electrical stimulation (FES) to promote muscle movement or prevent atrophy. In addition, stimulation may be delivered via one, two or more leads. DBS via one or two leads will be described for purposes of illustration throughout this disclosure, but should not be considered limiting of the inventions as broadly embodied and described herein.

DBS may be used to treat dysfunctional neuronal activity in the brain which manifests as diseases or disorders such as Huntington's Disease, Parkinson's Disease, or movement disorders, for example. The exact mechanisms explaining why electrical stimulation therapy is capable of treating such conditions of the brain are not fully known, but symptoms of these diseases can be lessened or eliminated with stimulation therapy. Certain anatomical regions of brain 18 are responsible for producing the symptoms of brain disorders. For example, stimulating an anatomical region called the Substantia Nigra in brain 18 may reduce the number and magnitude of tremors experienced by patient 12. Other examples include stimulation of the subthalamic nucleus, globus pallidus interna, ventral intermediate nucleus, or zona inserta. Anatomical regions such as these are targeted by the physician during implantation or lead 14 and programming of implantable stimulator 20. During implantation, the physician attempts to position the lead as close to these regions as possible.

Although DBS may successfully reduce symptoms of some neurological diseases, the stimulation commonly causes unwanted side effects as well. Side effects may include incontinence, tingling, loss of balance, paralysis, slurred speech, loss of memory, and many other neurological problems. Side effects may be mild to severe; however, most side effects are reversible when stimulation is stopped. DBS may cause one or more side effects by inadvertently providing electrical stimulation pulses to anatomical regions near the targeted anatomical region. For this reason, the physician typically programs the stimulation parameters in order to balance effective therapy and minimal side effects to promote overall therapeutic efficacy.

Typical DBS leads include one or more ring electrodes placed along the longitudinal axis of the lead, such as lead 14. Each ring electrode extends around the entire circumference of the lead. Therefore, electrical current from the ring electrodes propagates radially in all directions from the active electrode. The resulting stimulation field reaches anatomical regions of brain 18 within a certain distance in all directions. The stimulation field may reach the target anatomical region, but the stimulation field may also affect non-target anatomical regions and produce unwanted side effects. Implanting a lead with a more complex electrode array geometry may help to customize the stimulation field and provide improved therapy while decreasing side effects. For example, stimulation fields may be delivered on a more directional basis to more selectively target specific anatomical structures. By selecting electrodes at particular angular positions, a field may be generally limited to one side of a lead rather than all sides of the lead, making the field more directional.

Lead 14 has a complex electrode array geometry. In the example of FIG. 1, lead 14 includes four electrode "levels" at different axial positions along the length of the lead. Each level includes four electrodes generally arranged in a ring. However, the electrodes are non-contiguous with one another. The electrodes may be referred to as segmented electrodes or electrode segments. Each electrode is coupled to a respective electrical conductor within lead 14. Hence, lead 14 includes multiple electrical conductors, e.g., wires, cables or the like, that extend from the proximal end of the lead to respective electrodes to electrically couple the electrodes to electrical terminals associated with implantable stimulator 20.

Each electrode is positioned at a different angular position around the circumference of implantable lead 14, which has a generally circular cross-section in the example of FIG. 1. Each electrode is independently selectable so that stimulation energy can be delivered from the lead at different axial and angular positions. In some embodiments, lead 14 may include combinations of complex electrode array geometries and simple electrode array geometries. For example, ring electrodes that extend about the entire circumference of the lead may be used in combination with electrodes disposed at different axial and angular positions. Selective activation of the electrodes carried by lead 14 can produce customizable stimulation fields that may be directed to a particular side of lead 14 in order to isolate the stimulation field around a target anatomical region of brain 18.

Producing directional or irregular stimulation fields with lead 14 not only allows system 10 to more effectively treat certain anatomical regions of brain 18, but can also reduce or eliminate side effects relative to spherical stimulation fields produced by a leads with simple electrode array geometries. The center of the stimulation field may be moved away from lead 14 to avoid unwanted stimulation or compensate for inaccurately placed leads. Since leads may also migrate within brain 18 or other stimulation sites slightly, a customizable stimulation field may provide a longer duration of effective therapy as stimulation needs of patient 12 change.

Programming delivery of stimulation via lead 14 is more involved and complex when compared to leads having simple electrode array geometries because of the increased number of electrode combinations and positions, and resulting stimulation fields. Effective programming may be difficult for the physician if the physician is required to systematically select each electrode of lead 14 in order to find the electrode combinations that provide therapy and minimal side effects. While the physician may still desire the ability to manually select certain general areas of electrodes of lead 14, i.e. the group of electrodes at one level of the lead, programming time may be reduced if the physician is able to view the lead from different positions and manipulate axial and rotational or translational controls in an electrode view or field view. In addition, the physician may be able to manipulate or even initially define a stimulation field in a field view such that the programmer automatically generates the stimulation parameters that would produce the stimulation field in patient 12, in contrast to manually selecting electrode combinations and stimulation parameters. These aspects of programming the stimulation parameters will be further discussed in more detail.

The user interface of programmer 19 displays, e.g., with a liquid crystal display (LCD), a representation of lead 14 with multiple perspectives, e.g., an axial perspective and a cross-sectional perspective. The multiple perspectives may be displayed individually on a selective basis, or simultaneously so that the user can view two or more perspectives at the same time. In effect, axial and cross-sectional perspectives provide two different two-dimensional perspectives that together illustrates a three-dimensional electrode programming space.

In some embodiments, lead 14 may be represented on the display of the user interface in conjunction with a representation of a target anatomical region, such as the brain or spinal cord, and positioned according to the actual implantation location. The positioning of the representation of the lead 14 relative to the anatomical region can be controlled manually by the physician or directly from imaging information taken indicating the actual position of the lead within brain 18.

The physician interacts with the user interface to manually select and program particular electrodes of lead 14 via an electrode selection view, or select an electrode level of the lead and adjust the resulting stimulation field. Once the physician has defined the one or more stimulation fields, programmer 19 generates the stimulation parameters associated with each of the stimulation fields and transmits the parameters to implantable stimulator 20. Hence, the user interface of programmer 19 may permit the user to manually select electrode combinations and associated stimulation parameters, or simply specify and manipulate a stimulation field in terms of size, direction and shape, in which case programmer 19 or implantable stimulator 20 automatically adjusts electrode combinations and parameters to approximate the desired stimulation field. In some embodiments, the user interface may restrict the ability of the physician to define the stimulation fields based upon the stimulation capabilities of implantable stimulator 20 and lead 14. For example, the physician may not make the stimulation field larger when the voltage or current amplitude cannot be increased any further, or when no more electrodes are available in the desired direction of the stimulation field.

Additionally, the user interface may restrict the physician from applying the stimulation field to anatomical regions specifically banned from stimulation. These anatomical regions may severely alter the physiology of patient 12 and cause detrimental side effects or irreversible side effects. Accordingly, the physician may manually lockout potentially unsafe electrodes or electrode levels based upon the actual implantation location of the lead. Therefore, the user interface may be configured to prevent the physician from selecting particular electrodes during the programming of stimulation parameters. Alternatively, or additionally, some electrodes or electrode levels may have predetermined parameter ranges that cannot be violated. For example, a minimum field value or parameter value may be specified to maintain field strength at a minimum level. Similarly, a maximum field value or parameter value may be specified to prevent stimulation in excess of a given level.

In some embodiments where the physician may define the stimulation field or modify a stimulation field from the electrode view, programmer 19 generates the stimulation parameter values required by the stimulation field and transmits the parameter values to implantable stimulator 20 via wireless telemetry. The parameter values may also be saved on programmer 19 for review at a later time. In some cases, programmer 19 may not be capable of generating stimulation parameter values that can produce the defined stimulation field within brain 18. Programmer 19 may display an error message to the physician alerting the physician to adjust the stimulation field. Programmer 19 may also display a reason why the stimulation field cannot be provided, such as the field is too large or an electrode is malfunctioning and cannot be used. Other errors may also be displayed to the physician. In addition, programmer 19 may prompt the physician to return to the electrode view to manually select stimulation parameters if a stimulation field is unacceptable.

The user interface may or may not be used to provide real-time programming of implantable stimulator 20. In one case, the physician uses the user interface to define stimulation fields, and programmer 19 generates the stimulation parameters when the physician has determined that the stimulation field is ready for therapy. In this manner, stimulation therapy perceived by patient 12 does not change at the same time the physician changes the stimulation field. In another case, however, the user interface could be used in a real-time programming environment to immediately adjust stimulation in response to changes made by the physician using the field view or electrode view.

System 10 may also include multiple leads 14 or electrodes on leads of other shapes and sizes. The user interface may allow the physician to program each lead simultaneously or require the physician to program each lead separately. In some DBS patients, two leads 14 are implanted at symmetrical locations within brain 18. For example, a first lead may be placed in the right hemisphere of brain 18 and a second lead may be placed at the same location within the left hemisphere of the brain. Programmer 19 may allow the physician to create a stimulation field for the first lead and create a mirrored stimulation field for the second lead. The physician may be able to make fine adjustment to either stimulation field to accommodate the slight anatomical region differences between the left and right hemispheres.

While lead 14 is described for use in DBS applications throughout this disclosure as an example, lead 14, or other leads, may be implanted at any other location within patient 12. For example, lead 14 may be implanted near the spinal cord, pudendal nerve, sacral nerve, or any other nervous or muscle tissue that may be stimulated. The user interface described herein may be used to program the stimulation parameters of any type of stimulation therapy. In the case of pelvic nerves, defining a stimulation field may allow the physician to stimulate multiple desired nerves without placing multiple leads deep into patient 12 and adjacent to sensitive nerve tissue. Therapy may also be changed if leads migrate to new locations within the tissue or patient 12 no longer perceives therapeutic effects of the stimulation.

FIGS. 2A and 2B are conceptual diagrams illustrating two different implantable stimulation leads. Leads 26 and 34 are embodiments of lead 14 shown in FIG. 1. As shown in FIG. 2A, lead 26 includes four electrode levels 32 (includes levels 32A-32D) located at various axial positions along the lengths of lead housing 30. In a DBS application, a retention device may reside on or within a burr hole in cranium 16 to secure the position of lead 26 within brain 18.

Lead 26 is implanted within brain 18 at a location determined by the physician to be near an anatomical region to be stimulated. Electrode levels 32A, 32B, 32C, and 32D are equally spaced along the length of lead housing 30. Each electrode level 32 may have two or more electrodes located at different angular positions around the circumference of lead housing 30. In one embodiment, each electrode level 32 includes four separate electrodes at four different angular positions. Electrodes at different levels, but the same angular positions, may be aligned with one another in a direction parallel to the longitudinal axis of lead 26.

Alternatively, electrodes of different electrode levels may be staggered at different angular positions around the circumference of lead housing 30. Also, in some embodiments, different electrode levels may include different numbers of electrodes. For example, one electrode level at one axial position may include a single ring electrode that extends around the entire circumference of lead 26, while another electrode level at another axial position may include two electrodes at different angular positions, another electrode level at another axial position may include three electrodes at different angular positions, and another electrode level at another axial position may include four electrodes at different angular positions. In addition, lead 26 or 34 may include asymmetrical electrode locations around the circumference of each lead or electrodes of the same level that have different sizes. These electrodes may include semi-circular electrodes that may or may not be circumferentially aligned between electrode levels. Various combinations of electrode levels having different numbers of electrodes are contemplated.

In some embodiments, lead housing 30 may include a radiopaque stripe (not shown) along the outside of the lead housing. The radiopaque stripe corresponds to a circumferential location that allows the physician to identify electrodes in a transverse cross-sectional view of lead 26 with respect to the orientation of the lead within tissue of patient 12. Using the images of patient 12, the physician can use the radiopaque stripe as a marker to assess the exact orientation of lead 26 within the brain of patient 12. Orientation of lead 26 may be needed to easily program the stimulation parameters without providing the actual anatomy of patient 12 to the physician with respect to lead 26. In other embodiments, a marking mechanism other than a radiopaque stripe may be used to identify the orientation of lead 14. These marking mechanisms may include something similar to a tab, detent, or other structure on the outside of lead housing 30. In some embodiments, the physician may note the position of markings along lead wire 24 during implantation to determine the orientation of lead 14 within patient 12.

FIG. 2B illustrates a lead 34 that includes more electrode levels than lead 26. Lead 34 includes mounting base 36 and lead housing 38. In the example of FIG. 2B, eight electrode levels 40 (40A-40H) are located at the distal end of lead 34. Each electrode level 40 is evenly spaced from the adjacent electrode level and includes one or more electrodes. In a preferred embodiment, each electrode level 40 includes four circumferential electrodes. Therefore, lead 34 includes 32 circumferential electrodes in the example of FIG. 2B. Each electrode may be substantially rectangular in shape. Alternatively, the individual electrodes may have alternative shapes, e.g., circular, oval, triangular, or the like.

In alternative embodiments, electrode levels 32 or 40 are not evenly spaced along the longitudinal axis of the respective leads 26 and 34. For example, electrode levels 32C and 32D may be spaced approximately 3 millimeters (mm) apart while electrodes 32A and 32B are 10 mm apart. Variable spaced electrode levels may be useful in reaching target anatomical regions deep within brain 18 while avoiding potentially dangerous anatomical regions.

Leads 26 and 34 may be substantially rigid to prevent the implanted lead from varying from the expected lead shape. Leads 26 or 34 may be substantially cylindrical in shape. The leads may be substantially straight and rigid, or include one or more curves to reach target anatomical regions of brain 18. In some embodiments, leads 26 or 34 may be similar to a flat paddle lead or a conformable lead shaped for patient 12. Also, in other embodiments, leads 26 and 34 may any of a variety of different polygonal cross sections taken transverse to the longitudinal axis of the lead.

Lead housings 30 and 38 may continue directly into lead wire 24. Lead housing 30 or 38 may include a right angle connector that allows lead 26 and 34 to be inserted into cranium 16. Alternatively, the entire lead extending from the stimulator (or a lead extension) to the stimulation site may have a continuous lead body. For example, the lead may be uniform as it leaves the burr hole in the head. A retention device squeezes the lead as it leaves the burr hole and the lead is then smoothly bent over at approximately 90 degrees to continue onto the outside of the skull and under the skin. The lead may continue to a proximal connector end which will have full ring or half ring connector electrodes. The connector end plugs into an extension. The extension continues down to the stimulator. In embodiments of system 10 including two or more leads 14, each lead may be connected to only one lead wire 24. In this case, a connector at the surface of cranium 16 may couple each lead 14 to lead wire 24.

Figure 3A:
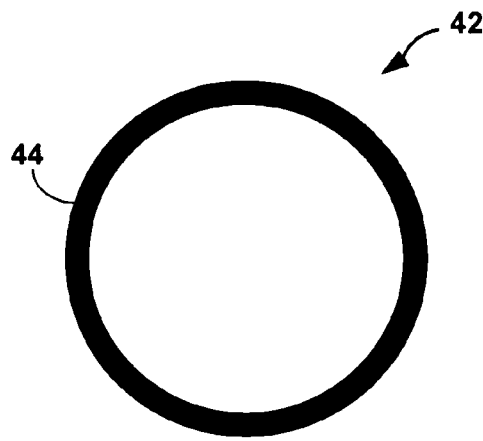
FIGS. 3A-3D are cross-sections of example stimulation leads having one or more electrodes around the circumference of the lead.

FIGS. 3A-3D are transverse cross-sections of example stimulation leads having one or more electrodes around the circumference of the lead. As shown in FIGS. 3A-3D, one electrode level, such as one of electrode levels 32 and 40 of leads 26 and 34, respectively, are shown to include one or more electrodes. FIG. 3A shows an electrode level 42 that includes circumferential electrode 44. Circumferential electrode 44 encircles the entire electrode level 42 and forms a conventional ring electrode. Circumferential electrode 44 may be utilized as a cathode or anode as configured by the user interface.

Figure 3B:
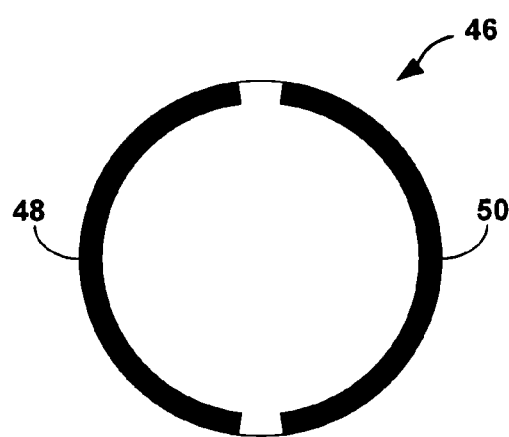

FIG. 3B shows electrode level 46 which includes two electrodes 48 and 50. Each electrode 48 and 50 wraps approximately 170 degrees around the circumference of electrode level 46. Spaces of approximately 10 degrees are located between electrodes 48 and 50 to prevent inadvertent coupling of electrical current between the electrodes. Each electrode 48 and 50 may be programmed to act as an anode or cathode.

Figure 3C:
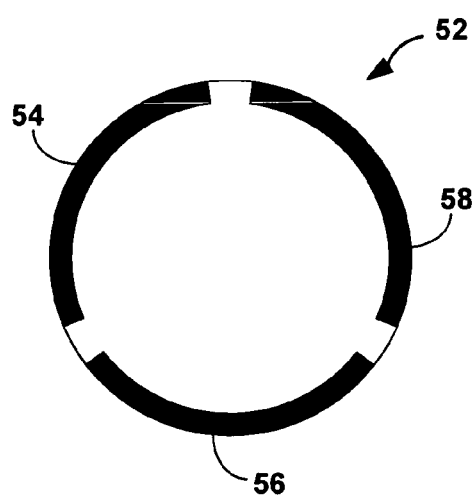

FIG. 3C shows electrode level 52 which includes three equally sized electrodes 54, 56 and 58. Each electrode 54, 56 and 58 encompasses approximately 110 degrees of the circumference of electrode level 52. Similar to electrode level 46, spaces of approximately 10 degrees separate electrode 54, 56 and 58. Electrodes 54, 56 and 58 may be independently programmed as an anode or cathode for stimulation.

Figure 3D:
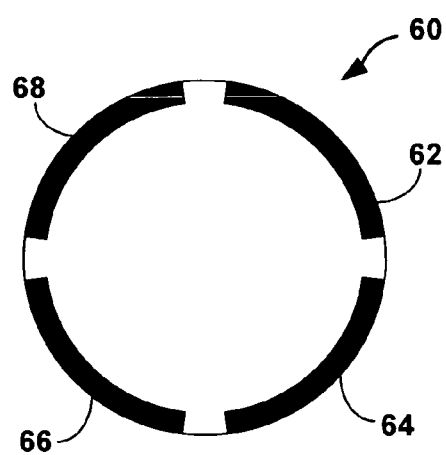

FIG. 3D shows electrode level 60 which includes four electrodes 62, 64, 66 and 68. Each electrode 62-68 covers approximately 80 degrees of the circumference with approximately 10 degrees of insulation space between the electrodes. In other embodiments, up to ten or more electrodes may be included within an electrode level. In alternative embodiments, consecutive electrode levels of lead 14 may include a variety of electrode levels 42, 46, 52 or 60. For example, lead 14 may include alternative electrode levels of electrode levels 62 and 60 depicted in FIGS. 3C and 3D. In this manner, various stimulation field shapes may be produced within brain 18 of patient 12. In addition, circumferential electrodes may not be aligned along the length of their respective lead. Further, the above-described sizes of electrodes within an electrode level are merely examples, and the invention is not limited to the example electrode sizes.

Also, the insulation space, or non-electrode surface area, between adjacent electrodes may be of varying size. Generally, the space may be between approximately 1 degree and approximately 20 degrees. More specifically, the space may be between approximately 5 and approximately 15 degrees. Smaller spaces may allow a greater volume of tissue to be stimulated. In alternative embodiments, circumferential electrode size may be varied around the circumference of an electrode level. In addition, insulation spaces may vary in size as well. Such unsymmetrical electrode levels may be used in leads implanted at tissues needing certain shaped stimulation fields.

Figure 4:
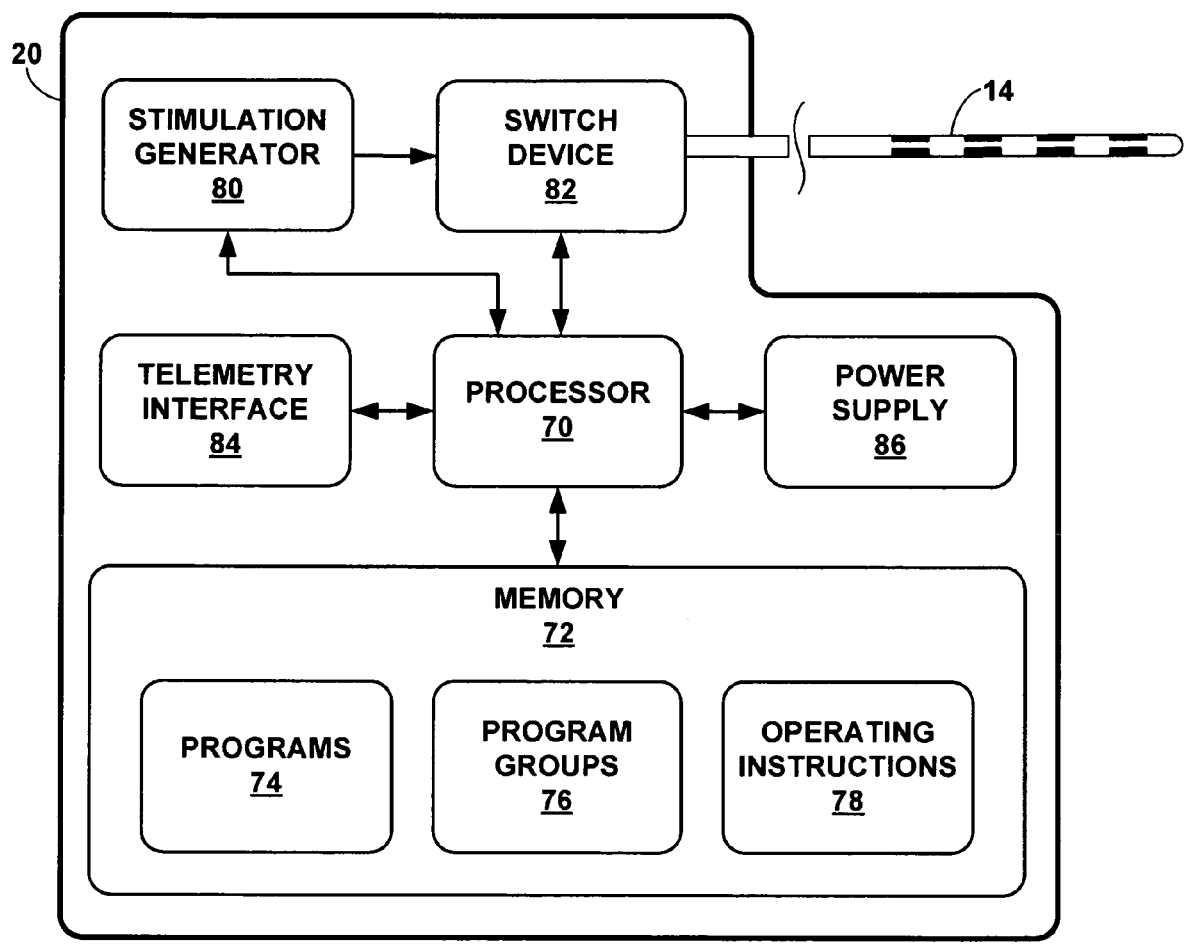
FIG. 4 is a block diagram illustrating an example implantable stimulator for delivery of electrical stimulation therapy via one or more leads having a complex electrode array geometry.

FIG. 4 is a block diagram illustrating an example implantable stimulator 20 for delivery of electrical stimulation therapy via one or more leads having a complex electrode array geometry. As shown in FIG. 4, the implantable stimulator 20 includes lead 14 (of FIG. 1), processor 70, memory 72, stimulation generator 80, switch device 82, power supply 86, and telemetry interface 84. Stimulator 20 delivers neurostimulation therapy via electrodes carried by one or more leads 14. Again, the electrodes may be arranged in a complex electrode array geometry. In the example illustrated in FIG. 4, lead 14 includes four electrode levels, each of which may include multiple non-contiguous electrodes at different angular positions about the circumference of the lead. The configuration, type, and number of electrodes illustrated in FIG. 4 are merely exemplary. For example, implantable stimulator 20 may include any number of leads 14 that each has any number of electrodes.

Memory 72 includes computer-readable instructions that, when executed by processor 70, cause stimulator 20 to perform various functions. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 72 may include programs 74, program groups 76, and operating instructions 78 in separate memories within memory 72 or separate areas within the memory. Each program 74 defines a particular program of therapy in terms of electrode combination, electrode polarity, current or voltage amplitude, pulse width and pulse rate. A program group 76 defines a group of programs that may be delivered together on an overlapping or non-overlapping basis. Operating instructions 78 guide general operation of the neurostimulator under control of processor 70.

Stimulation generator 80 produces stimulation pulses for delivery to the patient via selected electrode combinations. In other embodiments, stimulation generator 80 may produce continuous sine waves or other non-pulse signals for delivery to patient 12. Processor 70 controls stimulation generator 80 according to programs 74 and program groups 76 stored in memory 72 to apply particular stimulation parameters specified by one or more of programs, such as amplitude, pulse width, and pulse rate. Processor 70 may include a microprocessor, a controller, a digital signal processor (DSP), an application specific integrated circuit (ASIC), a field-programmable gate array (FPGA), or equivalent discrete or integrated logic circuitry.

Processor 70 also controls switch device 82 to apply the pulses generated by stimulation generator 80 to selected electrode combinations carried by lead 14. In particular, switch device 82 couples stimulation pulses to selected conductors within lead 14 which, in turn, deliver the stimulation pulses across selected electrodes. Switch device 82 may be a switch array, switch matrix, multiplexer, or any other type of switching device suitable to selectively couple stimulation energy to selected electrodes. Hence, stimulation generator 80 is coupled to electrodes via switch device 82 and conductors within lead 14.

Stimulation generator 80 may be a single- or multi-channel stimulation generator. In particular, stimulation generator 80 may be capable of delivering, a single stimulation pulse, multiple stimulation pulses, or continuous signal at a given time via a single electrode combination or multiple stimulation pulses at a given time via multiple electrode combinations. In some embodiments, however, stimulation generator 80 and switch device 82 may be configured to deliver multiple channels on a time-interleaved basis. In this case, switch device 82 serves to time division multiplex the output of stimulation generator 80 across different electrode combinations at different times to deliver multiple programs or channels of stimulation energy to patient 12.

For testing of electrode combinations, processor 70 controls stimulation generator 80 to smoothly shift stimulation energy between different electrode combinations. In response, stimulation generator 80 shifts between electrode combinations of different programs by incrementally adjusting the amplitudes of the electrode combinations to smoothly shift from one electrode combination to another. For example, processor 70 may be responsive to changes in the programs, as received from programmer 19, to control switch device 82 and stimulation generator 80 to deliver stimulation pulses or groups of pulses to different electrode combinations.

The external programmer 19 controls stimulator 20 to test electrode combinations so that a user may identify desirable combinations. Telemetry interface 84 supports wireless communication between implantable stimulator 20 and an external programmer 19 under control of processor 70. Telemetry interface 84 may allow processor 70 to communicate with programmer 19 during the electrode testing process. In particular, processor 70 receives, as updates to programs, values for stimulation parameters such as amplitude and electrode combination, from programmer 19 via telemetry interface 84, and delivers one or more stimulation pulses according to the received stimulation parameters.

The various components of implantable stimulator 20 are coupled to power supply 86, which may include a rechargeable or non-rechargeable battery. A non-rechargeable battery may be selected to last for several years, while a rechargeable battery may be inductively charged from an external device, e.g., on a daily or weekly basis. In other embodiments, power supply 86 may be powered by proximal inductive interaction with an external power supply carried by patient 12.

Figure 5:
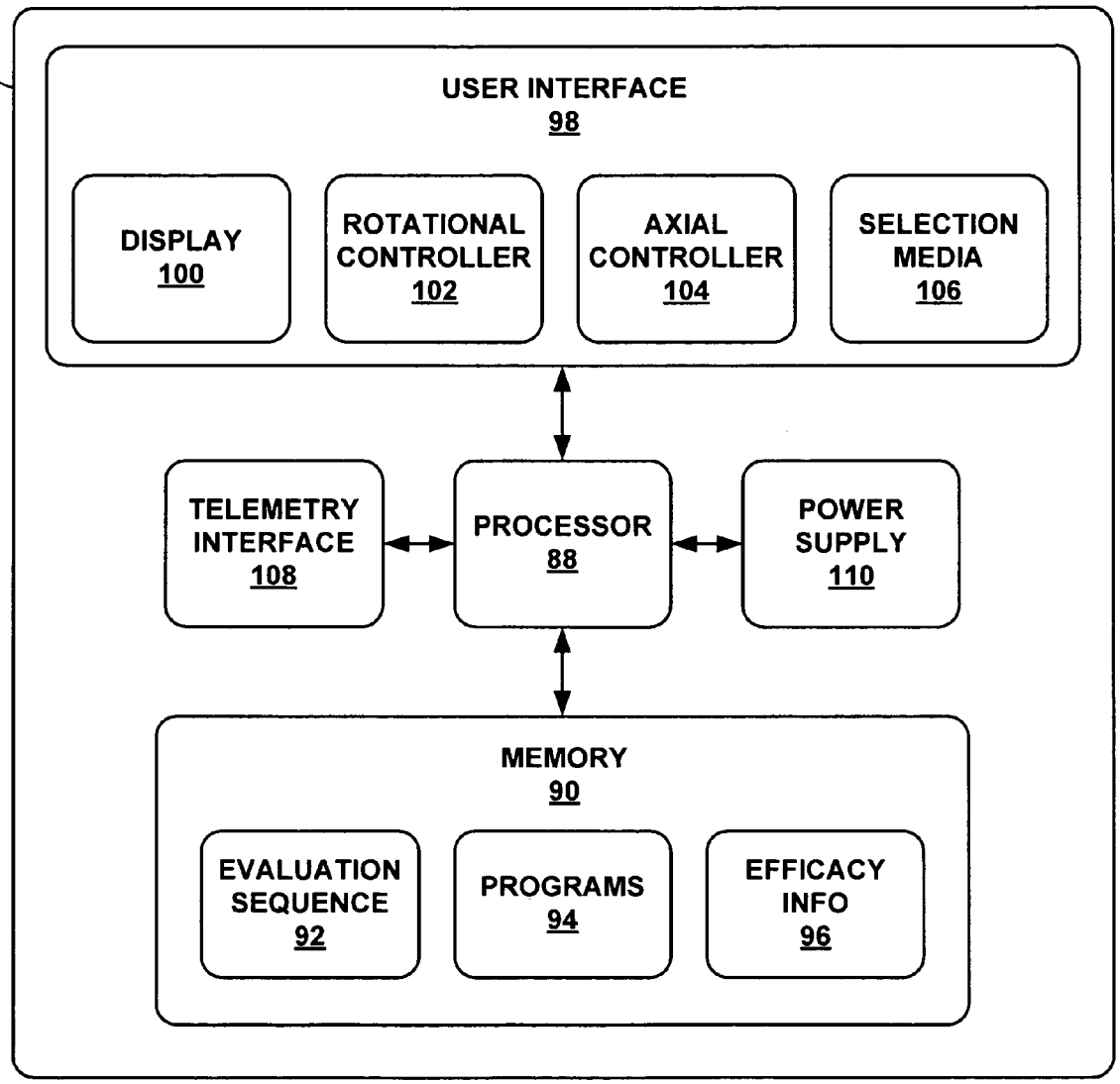
FIG. 5 is a block diagram illustrating an example programmer for programming and controlling the implantable stimulator of FIG. 4.

FIG. 5 is a block diagram illustrating an example programmer for programming and controlling the implantable stimulator of FIG. 4. In the example of FIG. 5, programmer 19 includes processor 88, memory 90, telemetry interface 108, power supply 110 and user interface 98. In general, a user, i.e., a physician or patient, uses programmer 19 to program and control implantable stimulator 20 shown in FIG. 4.

In the example of FIG. 5, memory 90 stores programs 94 specifying electrode combinations, electrode polarities, and stimulation parameters for download to the implantable stimulator 20. Memory 90 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In addition to programs 94, memory 90 may store an evaluation sequence 92 that guides the user in selection of electrode combinations and stimulation parameters, or automatically selects electrode combinations and stimulation parameters for evaluation of efficacy. For example, evaluation sequence 92 may specify a predetermined progression of electrode combinations to be selected for evaluation, or provide rules for dynamic selection of electrode combinations during the course of evaluation.

Memory 90 also may record efficacy information 96 for particular programs 94. Specifically, upon selection of an electrode combination and stimulation parameters as a program, programmer 19 may direct implantable stimulator 20 to apply the program. Upon application of the program, the patient may provide feedback concerning efficacy. The user, which may be a physician or the patient, then records the efficacy information in memory 90 of programmer 19. In this manner, different programs can be rated in terms of efficacy so that the user ultimately may select an effective electrode combination and stimulation parameters.

A user interacts with processor 88 via user interface 98 in order to identify efficacious electrode combinations and stimulation parameters as described herein. Processor 88 may provide display 100, i.e., a graphical user interface (GUI), via user interface 98 to facilitate interaction with the user. Processor 88 may include a microprocessor, a microcontroller, a DSP, an ASIC, an FPGA, or other equivalent discrete or integrated logic circuitry. The user interface may include display 100 and one or more input media. In addition, the user interface may include lights, audible alerts, or tactile alerts.

Notably, as shown in FIG. 5, the input media of user interface 98 includes rotational controller 102 and axial controller 104. Axial controller 104 permits a user to move electrode combinations or stimulation fields up or down along the length of a lead, i.e., lead 14, by selecting different combinations of electrodes. Rotational controller 102 permits the user to move electrode combinations or stimulation fields around the lead by selecting combinations of electrodes at different angular positions. In addition, axial controller 104 and rotational controller 102 may be configured to permit the user to view different electrodes, e.g., from multiple perspectives. User interface 98 also may present selection media 106 to permit the user to select particular electrode combinations for activation.

Using evaluation sequence 92, processor 88 may run a user-controlled test of a predetermined or dynamically generated sequence of electrode combinations to identify effective electrode combinations for alleviating symptom areas. Processor 88 may receive a pre-defined set of electrode combinations to test from a physician and store the pre-defined set of electrode combinations as a set of programs, either alone or in combination with stimulation parameters. Alternatively, processor 88 may execute an electrode combination search algorithm according to evaluation sequence stored 92 in memory 90 to select individual electrodes or electrode combinations to test.

Processor 88 controls stimulator 19 via telemetry interface 108 to test selected electrode combinations by controlling the stimulator to deliver neurostimulation therapy to patient 12 via the selected electrode combinations. In particular, processor 88 transmits programming signals to implantable stimulator 20 via telemetry interface 108. As a sequence of electrode combinations proceeds, the programming signals may be transmitted at a rate consistent with the control input provided by a user. In this manner, the user may quickly observe the effects of each increment in the change between electrode combinations. In some cases, e.g., for DBS applications, effects of an electrode or parameter change may not be immediately evident. In such cases, a change may be activated and evaluated over a period of minutes, hours, or days before another change is initiated.

After completion of electrode testing, processor 88 may transmit one or more of the programs created by the physician to stimulator 20 via telemetry interface 108 for storage in the stimulator, or to another programmer used by patient 12 to control delivery of neurostimulation therapy, e.g., via wireless or wired input/output interface. In either case, the selected electrode combinations can then be used to deliver therapy chronically or over an extended period of time.

Programmer 19 may be provided in the form of a handheld device, portable computer, or workstation that provides a user interface to a physician or patient. The physician or patient interacts with user interface 98 to program stimulation parameters for implantable stimulator 20 via external programmer 19. Hence, various aspects of user interface 98 described herein may be provided in the form of physician programmer, a patient programmer or both.

FIGS. 6-21 are schematic diagrams illustrating example user interfaces presented by embodiments of programmer 19 of FIG. 5. In each example, the user interface is an embodiment of user interface 98 of FIG. 5, and may provide axial and rotational or translational input media to move electrode combinations axially or rotationally, view leads from different perspectives, e.g., side or cross-sectional, and move electric stimulation fields axially or rotationally. In addition, in some embodiments, the user interface may provide field views and electrode views.

In the electrode view, the user selects individual electrodes to form an electrode combination, and specifies parameters for stimulation delivered via the electrode combination. In a field view, the user manipulates a representation of an electrical stimulation field produced by a selected electrode combination. For example, the user may change the size, shape or position of the field using graphical input media such as cursor or stylus control. In some embodiments, the user may be able to create a stimulation field in the field view and direct the programmer to generate stimulation parameters that would best match the stimulation field.

In the field view, the user may perform various field manipulation operations such as a grow/shrink operation to expand or contract the size of a field, a spread/focus operation to expand or contract the number of electrodes included in an electrode combination, and a split/merge operation to divide a single electrode combination into multiple combinations or vice versa. In response to such operations, a programmer selects appropriate electrode combinations, polarities, amplitudes, pulse widths, and pulse rates sufficient to support the specified operation.

Figure 6:
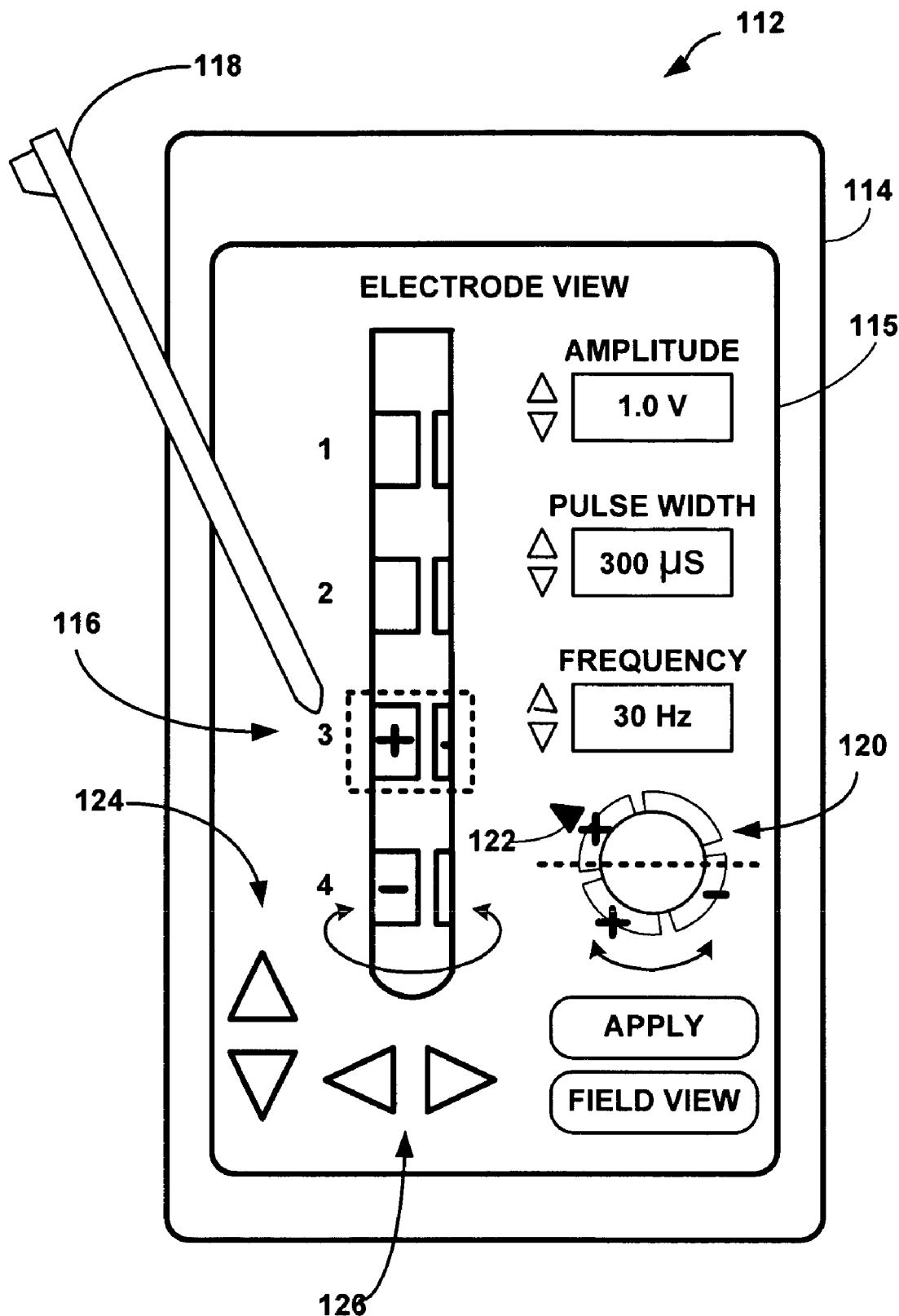
FIGS. 6-21 are schematic diagrams illustrating example user interfaces presented by the programmer of FIG. 5.

In the example of FIG. 6, a user interface 112 is provided by a programmer 114. User interface 112 includes a display screen 115 that shows a single lead having four electrode levels. Display screen 115 may be a touchscreen such that interactive media may be placed on the screen. Alternatively, or in addition, keys, buttons, wheels and other input devices may be provided on programmer 114, independently of display 115. Each electrode level includes four electrodes arranged at different angular positions around the circumference of the lead. User interface 112 provides a side view 116 of the lead, and a cross-sectional view 120 of the lead, e.g., the representation of lead 14. Side view 116 shows all of the electrodes along one side of the lead. In particular, side view 116 is a two-dimensional view that illustrates approximately 180 degrees of the circumference of the lead, and the axial length of a distal portion of the lead. In systems that include more than one lead 14 implanted within patient 12, user interface 112 may provide lead representations of two or more of the leads instead of just a single side and cross-sectional view of one lead.

With a complex electrode array geometry, however, side view 116 does not permit the user to view all electrodes carried by the lead. Again, the view is limited to only one side of the lead. To provide a more complete view, user interface 112 presents another perspective. In particular, cross-sectional view 120 shows a top view, or axial view, of one level of electrodes on the lead. In the example of FIG. 6, the third level of electrodes is shown in side view 116 and includes a cathode (+) and anode (−) in the visible electrodes. Again, however, it is not possible to view the other side of the lead in side view 116. For this reason, cross-sectional view 120 is provided to present electrodes on all sides of the lead at the electrode level being considered.

In the example of FIG. 6, cross-sectional view 120 reveals that there is another cathode in the third electrode level on the side of the lead that is not visible in the side view. The cross-sectional view 120 may include a horizontal dashed line that divides the bottom (front) and top (back) sides of the lead to indicate which portion is visible in the side view 116. In other words, the bottom half of the lead in the cross-sectional view corresponds to the visible (front) side of the lead in the side view 116. The top half of the lead in the cross-sectional view corresponds to the back side of the lead, which is not visible in the side view 116.

Cross-sectional view 120 also may include an arrow 122 that provides an orientation to cross-sectional view 120. For example, arrow 122 may be coincident with a radio-opaque stripe or marker carried by the lead. Alternatively, arrow 122 may indicate a point of reference relative to an anatomical structure near the implanted lead 14. In the context of DBS, for example, arrow 122 may point to the front, back or a selected side of a patient's cranium when viewed as a horizontal plane from the top.

Arrow 122 may be positioned based on known positioning data for lead 14 upon implantation within brain 18. The presentation of arrow 122 helps maintain the physician's or patient's orientation as the lead is rotated as described herein. As the user views the other side of the lead in the side view, for example, it may be difficult to immediately comprehend the spatial relationship between the electrodes on that side and the target anatomy. Simultaneous display of side view 116 and cross-sectional view 120 with arrow 120 may help to maintain the user's orientation.

As further shown in FIG. 6, user interface 112 may further include up/down arrows 124 and side-to-side arrows 126 or other equivalent input media such as vertical and horizontal scroll bars, scroll wheels, arrow buttons, or the like. Up/down arrows 124 serve as an axial control to permit the user to move electrode combinations up or down the length of the lead in the side view 116. For example, a user may walk a bipole up and down the lead to test different electrode positions. Side-to-side arrows 126 serve as a rotational control to permit the user to rotate the lead so that side view 116 rotates to reveal other electrodes on different sides of the lead. At the same, time, the side-to-side arrows 126 are used to rotate the cross-sectional view 120 so that the cross-sectional view always corresponds to an electrode level currently visible within the side view 116.

Side-to-side arrows 126 also rotate side view 116 to provide the user with access to another side of the lead to select additional or alternative electrodes. In the example of FIG. 6, only a single cross-sectional view 120 is presented by user interface 112 at a given time. For example, the cross-sectional view 120 may correspond to an electrode level that is presently being manipulated by the user. In FIG. 6, electrode level 3 (counting from the top of the lead to the bottom of the lead) is highlighted in a dashed box. The dashed box may indicate that the user has selected electrode level 3, e.g., with a stylus or other pointing media, or with up/down arrows 124, and that the user is adjusting the parameters for that combination of electrodes. An example of a stylus 118 is shown in FIG. 6.

In some embodiments, the user may select electrode combinations with stylus 118 by clicking on individual electrodes in the side view 1116. In some embodiments, the user also may select electrodes with stylus 118 by clicking on electrodes in the cross-sectional view. Hence, the user may rely on side view 116 or cross-sectional view 120 to select individual electrodes for inclusion in an electrode combination. To specify whether the electrode is to serve as an anode or cathode, the user may click multiple times on a given electrode. For example, the user may click once to select an electrode, twice to make the electrode an anode, three times to make the electrode a cathode, and four times to deselect the electrode.

When the user actuates the up/down arrows 124 to access a different electrode level in the side view 116, the highlighted or dashed box moves to track the up/down input and identify another electrode level. At the same time, the cross-sectional view 120 changes to depict electrodes at the newly selected electrode level. Hence, the cross-sectional view 120 illustrates the electrodes associated with one electrode level at a time, but changes to illustrate other levels as the user moves up or down to access different levels within the side view 116.

In other words, if the user has selected an electrode on electrode level 3, cross-sectional view 120 shows all of the electrodes at the various angular positions on level 3 and presents the portion of the lead that is visible in side view 116 below the horizontal line. If the user then selects an electrode on electrode level 1 in side view 116, the cross-sectional view 120 immediately tracks the change and shows all of the electrodes on electrode level 1. In addition, the user may proceed to select additional electrodes either within side view 116, e.g., to change levels, or within cross-sectional view 120, e.g., to select or deselect electrodes in that corresponding electrode level of the lead.

For each electrode combination selected by a user, the user may also specify stimulation parameters as shown in FIG. 6. For example, the user may specify voltage or current amplitude, pulse width, and pulse rate for stimulation pulses to be delivered via the selected electrode combination shown in the side and cross-sectional views 116 and 120. The user may use up/down arrows to change the values for respective parameters or directly enter values if numeric input is available in programmer 114.

Upon selecting an electrode combination and desired parameters, the user may download the combination and parameters to implantable stimulator 20 as a program or as adjustments to an existing program, and thereby cause the stimulator to apply the program. For example, the user may press a "program" (apply) button, in which case programmer 114 downloads instructions sufficient for stimulator 20 to carry out the desired program change. Downloads may be sent to stimulator 20 on a frequent basis to test numerous electrode combinations and parameter values. In some cases, the download may specify both an electrode combination and parameter values. In other cases, the download may be only an electrode combination or only a parameter change.

In the illustrated example, the electrode combinations and parameter values selected via programmer 114 may be downloaded at the instruction of a user, e.g., by pressing the "Apply" button shown in FIG. 6. For example, the user may specify an electrode combination and specify parameter values, and then instruct programmer 114 to download the program or program adjustments. Alternatively, in some embodiments, or in a selectable mode of operation, programmer 114 may transmit the changes to stimulator 20 substantially in real time so that a program presently being applied by the stimulator is adjusted as the user adjusts the electrode combination or parameter values.

For example, when the user adds an additional electrode to an electrode combination, removes an electrode from an electrode combination, changes the polarity of an electrode, or adjusts a parameter value, programmer 114 may immediately apply the selection, polarity change or adjustment to stimulator 20 so that the stimulation delivered by the stimulator immediately tracks the user's program changes. In this manner, stimulation may be smoothly shifted between different electrode combinations to identify combinations and parameter values that support therapeutic efficacy.

Figure 7:
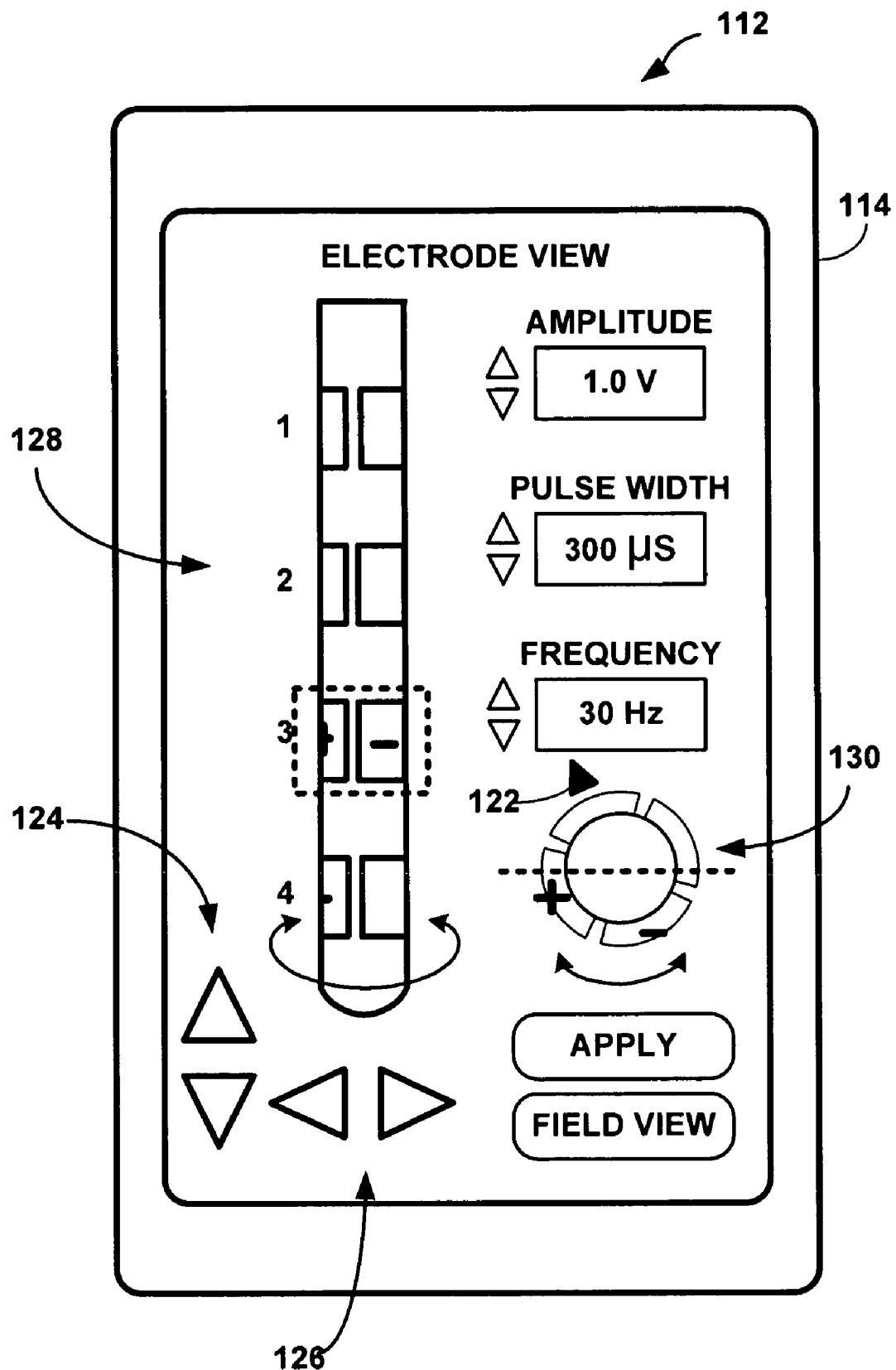

FIG. 7 is substantially identical to FIG. 6, but illustrates rotation of the lead in both the side view 128 and cross-sectional view 130. In the example of FIG. 7, the user has used user interface 114 and pressed the left side-to-side 124 to rotate the lead to left in side view 128 when compared to FIG. 6. Cross-sectional view 130 tracks the side view and shows that the + and − electrodes have rotated clock-wise such that a portion of the + electrode is above the horizontal line, indicating that it is not visible in side view 128. In addition, arrow 122 rotates with the lead in cross-sectional view 130 to preserve the user's sense of orientation of the lead relative to an anatomical structure.

Figure 8:
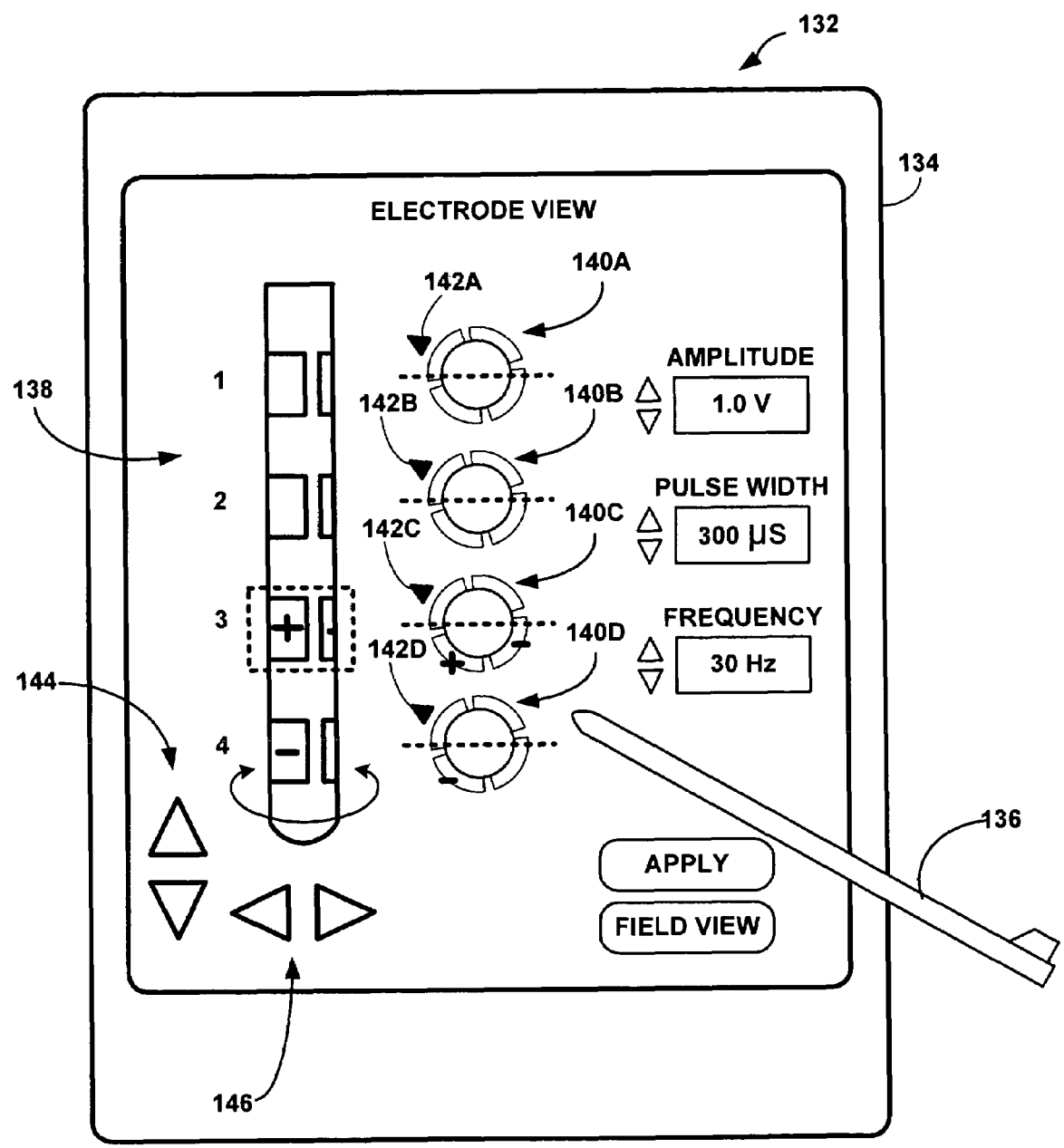

FIG. 8 is similar to FIGS. 6 and 7, but illustrates an example embodiment in which user interface 132 displays multiple cross-sectional views 140A, 140B, 140C, 140D are presented simultaneously so that the user can view the electrodes in all electrode levels of the lead. Each cross-sectional view 140A-140D (collectively "cross-sectional views 140") corresponds substantially to cross-sectional views 120 and 130 of FIGS. 6 and 7. Cross-section views 140 are presented adjacent to the corresponding electrode level in side view 138 of the lead. For example, cross-sectional views 140 correspond to electrode levels 1, 2, 3 and 4 (from top to bottom) in side view 138 of the lead. As the lead is rotated in response to actuation of arrows 146, cross-sectional views 140 track the rotation and may include the horizontal line and arrow 122 shown in FIGS. 6 and 7, to aid in maintaining user orientation.

Figure 9:
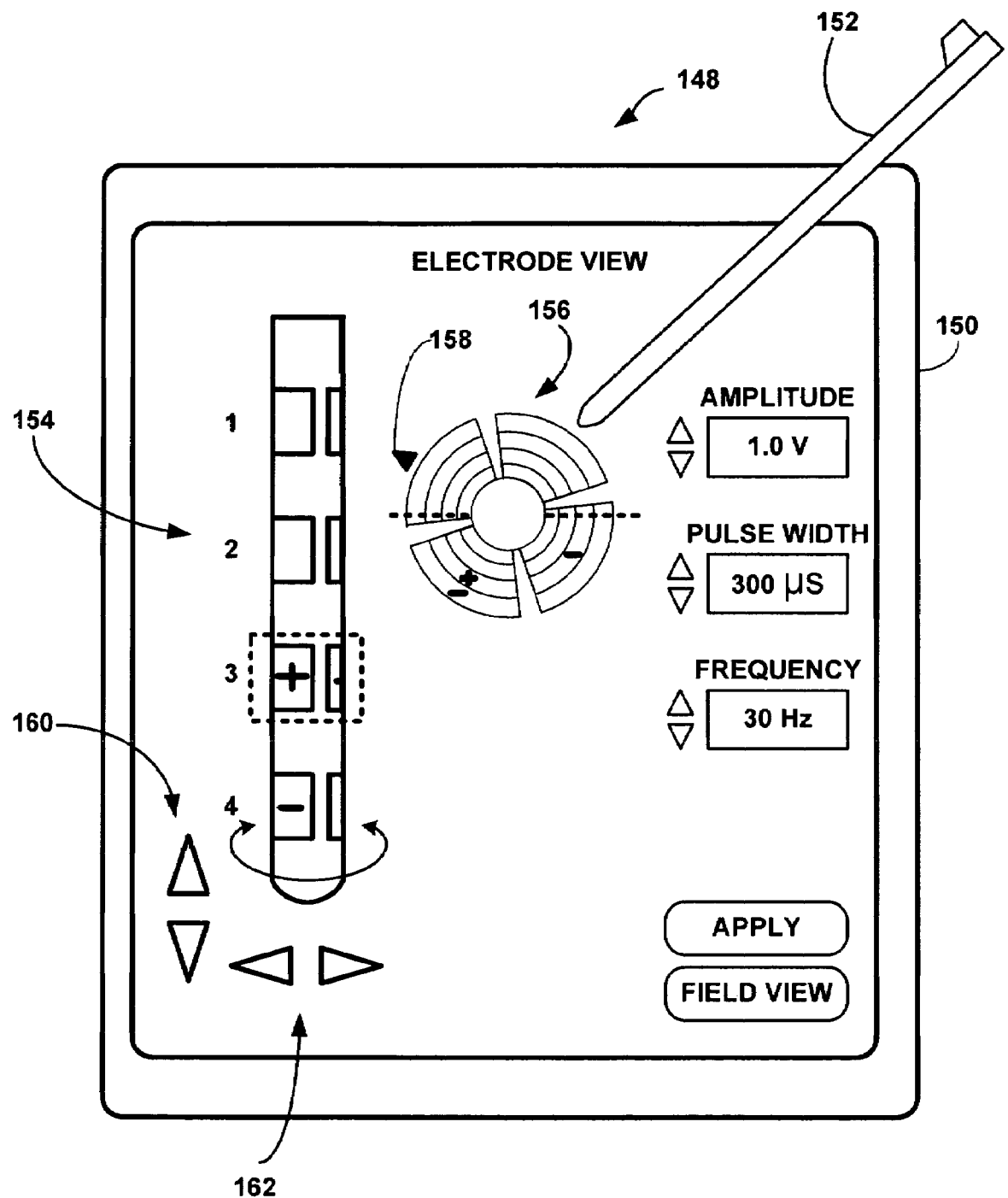

FIG. 9 illustrates an alternative embodiment of user interface 98. Instead of displaying multiple cross-sectional views 140 or a single cross-sectional view 120, user interface 148 of FIG. 9 includes a nested, coaxial, cross-sectional view, i.e., concentric axial view 156, of the various electrode levels of the lead. In particular, FIG. 9 shows side view 154 and arrows 160 and 162, but includes a concentric axial view 156 in which the electrodes arranged at different angular positions within the electrode levels or the lead are displayed concentrically. In this manner, all electrodes can be presented simultaneously in a more compact format, which may be especially desirable for smaller, handheld programmer 150 or applications in which more controls are to be presented to the user at once. In systems that include more than one lead 14 implanted within patient 12, user interface 148 may provide lead representations of two or more of the leads instead of just a single side and concentric axial view of one lead.

The electrodes for electrode level 1 (at the top of the lead) are shown in a first, innermost layer of concentric axial view 156. The electrodes for electrode levels 2, 3 and 4 are then shown in the second, third and fourth layers of the concentric axial view, where the fourth layer is an outermost layer. Again, the horizontal line and arrow 158 may be presented to aid in maintaining orientation. The electrodes in the concentric layers of concentric axial view 156 include + or − signs to indicate whether the electrodes have been selected and, if so, the polarity of the electrode. In addition to viewing the electrodes in concentric axial view 156, a user may select the electrodes in the concentric axial view, e.g., with a stylus, by clicking on the electrodes and then clicking repeatedly to specify polarity or deselect the electrode as mentioned previously.

Figure 10:
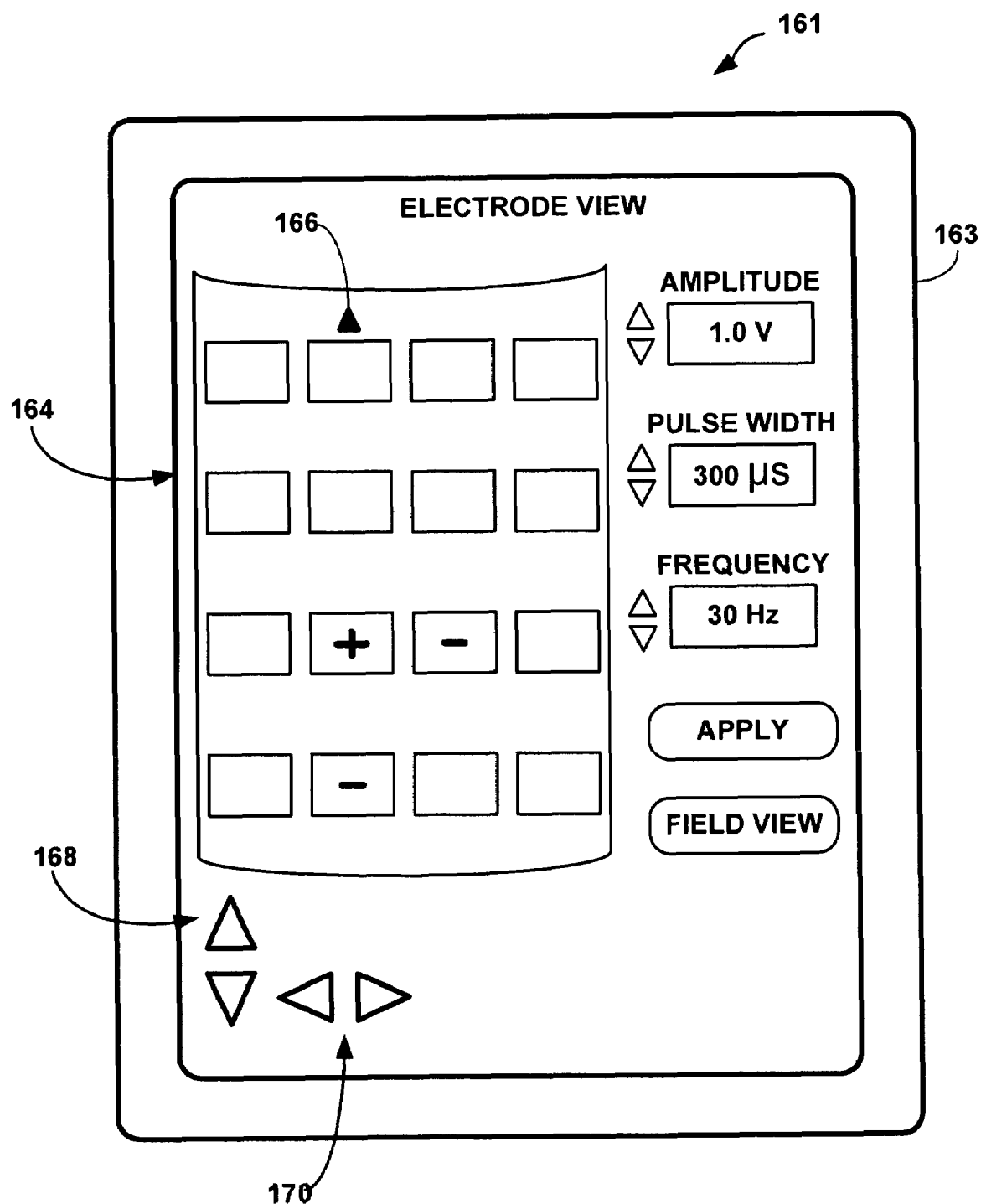

FIG. 10 illustrates another alternative embodiment of a user interface 161 provided by a programmer 163. In the example of FIG. 10, the electrodes at the various angular positions around the circumference of the lead are illustrated in user interface 161 as unwrapped two-dimensional (2D) array view 164 as if the cylindrical surface of the lead were "unrolled" and laid out flat. In this case, all electrodes and electrode levels are simultaneously visible. Arrows 168 and 170 may be used to move electrode combinations up/down or side-to-side, respectively. In particular, arrows 170 permit the user to simulate rotation of an electrode combination around the circumference of the lead. In systems that include more than one lead 14 implanted within patient 12, user interface 161 may provide lead representations of two or more of the leads instead of just an unwrapped view of one lead.

An orientation arrow 166 may be provided to show the orientation of the lead relative to an anatomical structure such as the front of the patient's cranium. As in the previous examples, a user may select individual electrodes and polarities by clicking on the electrodes with a stylus. Once an electrode combination is select, the user may "walk" the combination up, down, or around the unwrapped 2D array view 164 using arrows 74, 76. In addition, user interface 161 of FIG. 10 permits the user to adjust stimulation parameter values such as amplitude, pulse width and frequency.

In FIGS. 6-10, user interfaces 112, 132, 148 and 161 present an electrode view in which a user selects individual electrodes, combinations of electrodes, and stimulation parameter values, and views the electrodes using either an side view or a cross-sectional view with the aid of rotational control media. In each example, each user interface may further include a "Field View" button that enables the user to selectively activate a different viewing mode. In the field view mode, the user may or may not select individual electrodes, depending on design considerations. However, the field view permits the user to manipulate a representation of a stimulation field produced by an electrode combination and a set of parameter values.

Figure 11:
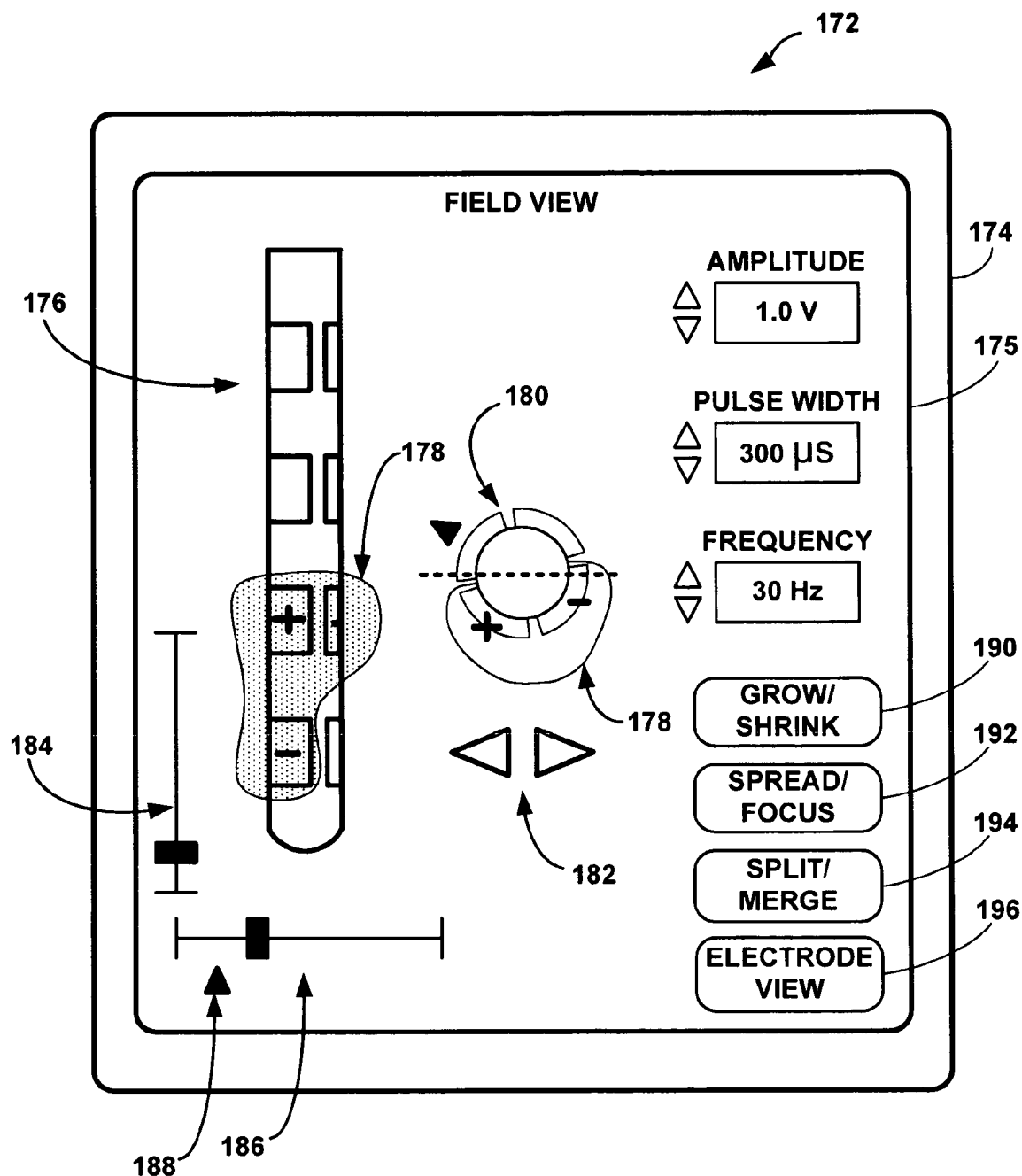
Figure 12:
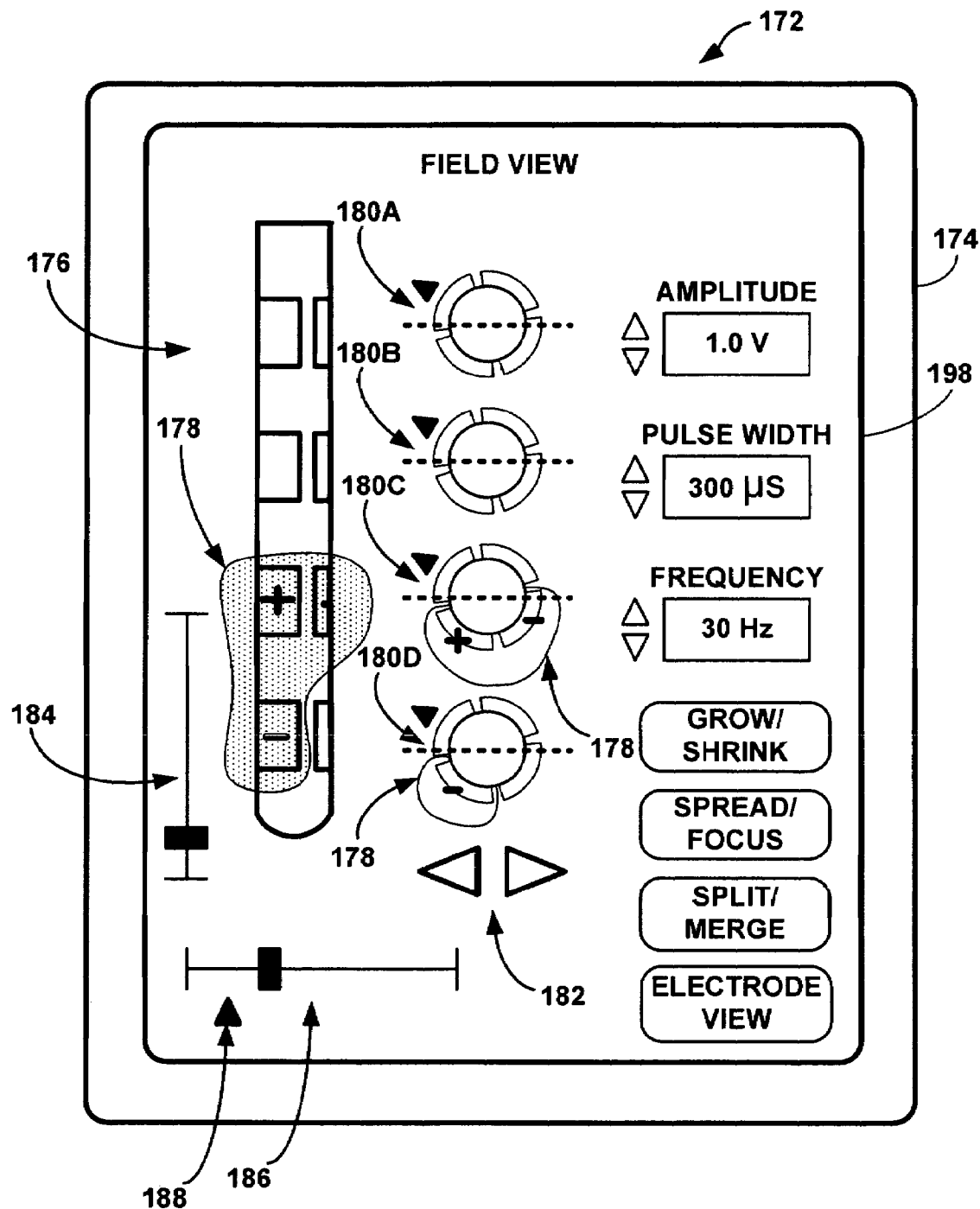

FIG. 11 illustrates user interface 172 that presents field view 175 of a lead having a complex electrode array geometry. FIG. 12 is similar to FIG. 11 but illustrates the presentation of multiple cross-sectional views of the lead in alignment with corresponding electrode levels of the lead in a field view 198. In the example of FIGS. 11 and 12, the user has selected an initial electrode combination, either manually or by selection for a set of electrode combinations provided by programmer 174, and has transitioned to field views 175 or 198 of the electrode combination. In the field view, user interface 172 presents a representation of a stimulation field 178 defined by the user and produced by the electrode combination, given the parameter values associated with stimulation delivered by the electrode combination and general tissue characteristics stored within programmer 174.

The size and shape of stimulation field 178 may be established based on generic physical characteristics of human tissue and known physical characteristics of the electrodes of lead 14. In other words, stimulation field 178 displayed in field view 175 may only be an approximation of what the stimulation field would be in brain 18. However, in some embodiments, physical characteristics of the actual anatomical structure of patient 12 being treated may be used to generate stimulation field 178. This anatomical structure information may be presented to programmer 174 in the form of patient anatomical data generated by an imaging modality, such as computed tomography (CT), magnetic resonance imagine (MRI), or any other volumetric imaging system. In the embodiment that uses the patient anatomical data, stimulation field 178 may be similar to an electrical field model, which is discussed in detail in FIGS. 37, 39, 41, and 44. For example, stimulation field 178 may rely on tissue impedance models, field propagation models, and the like. In some embodiments, stimulation field 178 may be a representation of an electrical field, current density, voltage gradient, or neuron activation, applied to a generic human tissue or the anatomy of patient 12. In addition, the clinician may be able to switch between any of these representations when desired.

In field views 175 or 198, the user may move the field up/down using vertical scroll bar 184 or some similar control device. As stimulation field 176 moves up or down in response to the user input, programmer 174 automatically selects appropriate electrode combinations to support the vertical movement of the stimulation field. For example, programmer 174 may phase electrodes in and out as stimulation field 178 travels upward or downward, reducing the stimulation energy delivered from some electrodes as the stimulation field moves away from them, and increasing the stimulation energy delivered by other electrodes as the filed moves toward them. Also, in FIG. 11, field view 175 may include arrows 182, or similar input media, that permit the user to transition between different electrode levels of the lead in cross-sectional view 180.

In addition, the user may rotate stimulation field 178 using horizontal scroll bar 186 or some similar control device. An arrow 188 may be provided next to horizontal scroll bar 186 to indicate the orientation of the lead relative to an anatomical structure. In addition, arrows may be provided in respective cross-section views 180A-D of field view 198 to maintain orientation. As the user rotates stimulation field 178, programmer 174 automatically selects appropriate electrode combinations to support the rotational movement of the stimulation field. As in the case of vertical movement, rotational movement of stimulation field 178 may be accomplished by gradually reducing the stimulation energy delivered to some electrodes as the stimulation field rotates away from them, and gradually increasing the stimulation energy delivered to other electrodes as the stimulation field rotates toward them. Side view 176 and cross-sectional view 180 permit the user to observe movement of stimulation field 178 from both an axial perspective and a rotational perspective.

Advantageously, movement of stimulation field 178 using scroll bars 184, 186 or similar input media permits the user to evaluate different field positions without the need to manually select electrodes and manually enter parameter values. Instead, programmer 174 automatically selects electrodes and parameter values in response to movement of stimulation field 178 by the user. Although scroll bars 184, 186 are illustrated as examples of input media for movement of stimulation field 178, other types of input media may be used. Examples include up/down arrows or side-to-side arrows, which may be presented on a touch screen or formed by buttons or keys on programmer 174.

As a further alternative, the user may select stimulation field 178 with a stylus, mouse, or other pointing device and drag the field upward, downward, or rotationally. In some embodiments, a mouse or other pointing device may support left or right click functionality to perform different operations relative to stimulation field 178. With a stylus, a first click on stimulation field 178 may initiate movement, dragging with the stylus directs movement, and a second click may terminate movement. In each case, programmer 174 responds to the specified movement by automatically adjusting the electrode combination and the stimulation parameters to approximate the characteristics of the stimulation field 178 presented on the display. As the stimulation parameter values change, the size and shape of stimulation field 178 presented on the display change. Similarly, as the electrode combination changes in terms of polarity or electrode selection, the size, shape or direction of stimulation field 178 presented on the display changes. In other embodiments, programmer 174 may utilize stimulation templates and select the best fitting stimulation template set to a newly modified stimulation field 178. Stimulation templates will be discussed further in FIGS. 30-36. Programmer 174 may limit the rate of movement of stimulation field 178. In other words, stimulation field 178 may only be moved a certain number of steps per second within user interface 172, or any other user interface that allows the clinician to drag the stimulation field. This rate movement limit may prevent unnecessary calculations or ensure patient comfort in real-time programming embodiments.

In addition to moving stimulation field 178, user interface 172 may permit the user to perform one or more operations that result in reconfiguration of the stimulation field. For example, the user may click on a border, i.e., an outer perimeter, of stimulation field 178, and drag it inward or outward to resize the stimulation field. Resizing by enlarging or shrinking stimulation field 178 in user interface 172 results in an increase or decrease in amplitude, pulse width or pulse rate of the stimulation energy. In some embodiments, enlarging or shrinking stimulation field 178 also may result in selection or deselection of electrodes included in the existing electrode combination. In either case, programmer 174 adjusts the electrode combination and/or parameter values in response to the enlargement or shrinkage of stimulation field 178 by the user.

When a user clicks on stimulation field 178 border and drags it, the entire stimulation field may be expanded in two dimensions in equal proportions. Alternatively, stimulation field 178 may expand only in the direction in which the user drags the stimulation field. For example, horizontal dragging of the field perimeter to enlarge stimulation field 178 may result in overall enlargement of the stimulation field, keeping the vertical to horizontal aspect ratio constant. Alternatively, horizontal dragging may result only in horizontal expansion, leaving the vertical dimension constant. The application of a constant or varying aspect ratio may be specified by a user as a user preference. Alternatively, programmer 174 may provide different aspect ratio modes on a selective basis for expansion and shrinkage of stimulation field 178.

To enlarge or shrink stimulation field 178, the user may simply click on the stimulation field border. Alternatively, the user may click on a grow/shrink button 190 as shown in FIGS. 11 and 12, and then click on the border of stimulation field 178 to drag it inward or outward and thereby adjust the size of the stimulation field. In response, programmer 174 automatically reconfigures the electrode combination and/or stimulation parameter values to approximate the resized stimulation field. As will be described, other field adjustment functions such as spread/focus button 192 and split/merge button 194 may be provided by user interface 172. In each case, the user changes stimulation field 178 by simply changing the representation of the stimulation field on field view 175 or 198, thereby avoiding the need to manually select electrodes and parameter values. However, the user may select "electrode view" at any time to return the electrode view screen, if desired. In some of these embodiments that allow the physician to enlarge, shrink, merge, or split stimulation field 178, programmer 174 may employ the use of stimulation templates, as will be further discussed herein.

Figure 13:
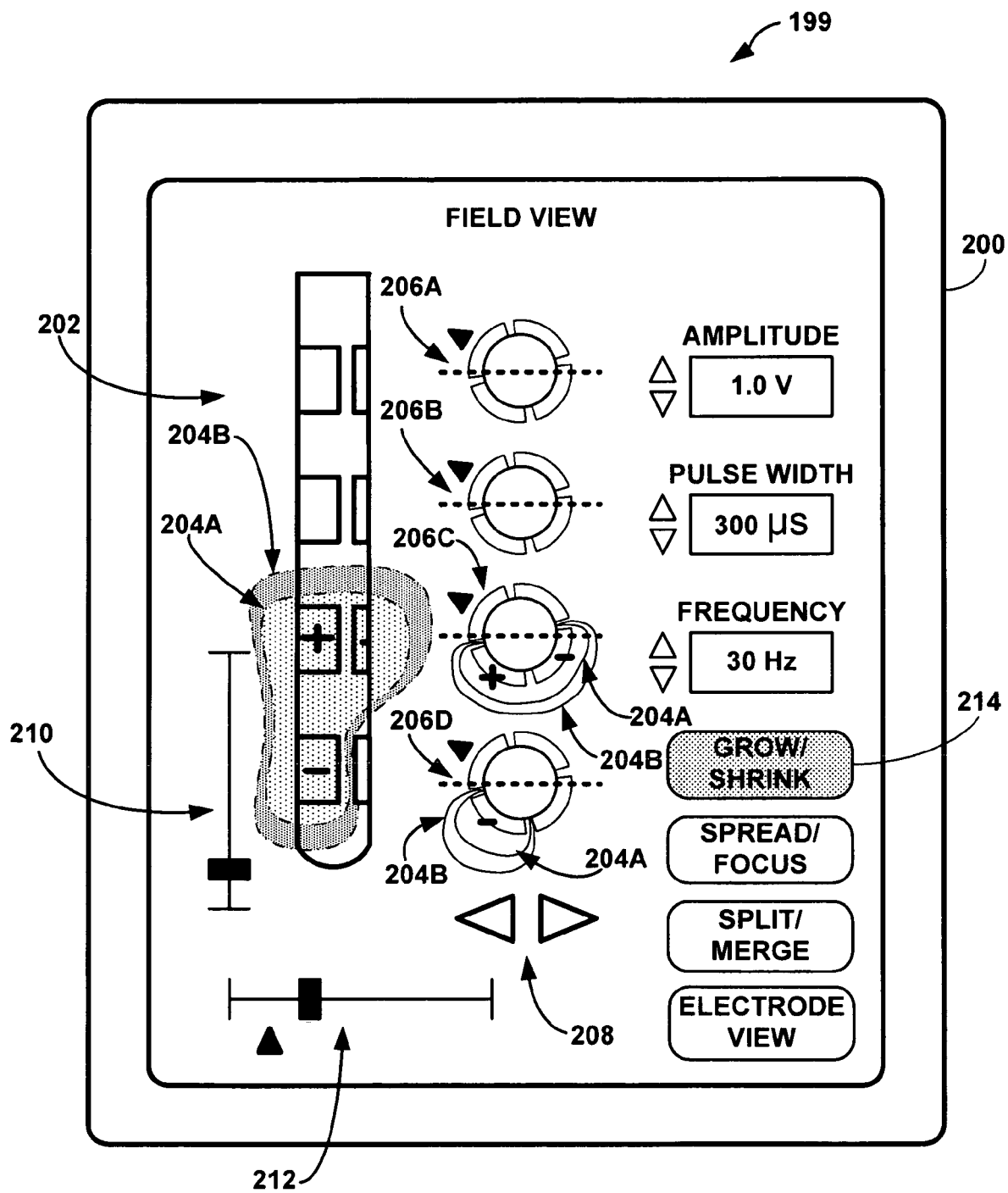

FIG. 13 illustrates selection of the grow/shrink feature by the user. User interface 199 is an embodiment of user interface 98, similar to other user interfaces herein, and is provided by a programmer 200. In the example of FIG. 13, the user expands the representation of stimulation field 204A by clicking and dragging on the field perimeter after selecting grow/shrink button 214. In particular, the user expands the stimulation field from stimulation field 204A to stimulation field 204B. User interface 199 shows the expansion of the stimulation field in side view 202 as well as in cross-sectional views 206C, 206D that include electrodes in the electrode combination that produces the stimulation field. As shown in FIG. 13, the shape of stimulation field 204B in the cross-sectional views 206C, 206D is somewhat different as stimulation field 204A-B may be sized differently at different electrode levels of the lead.

Figure 14:
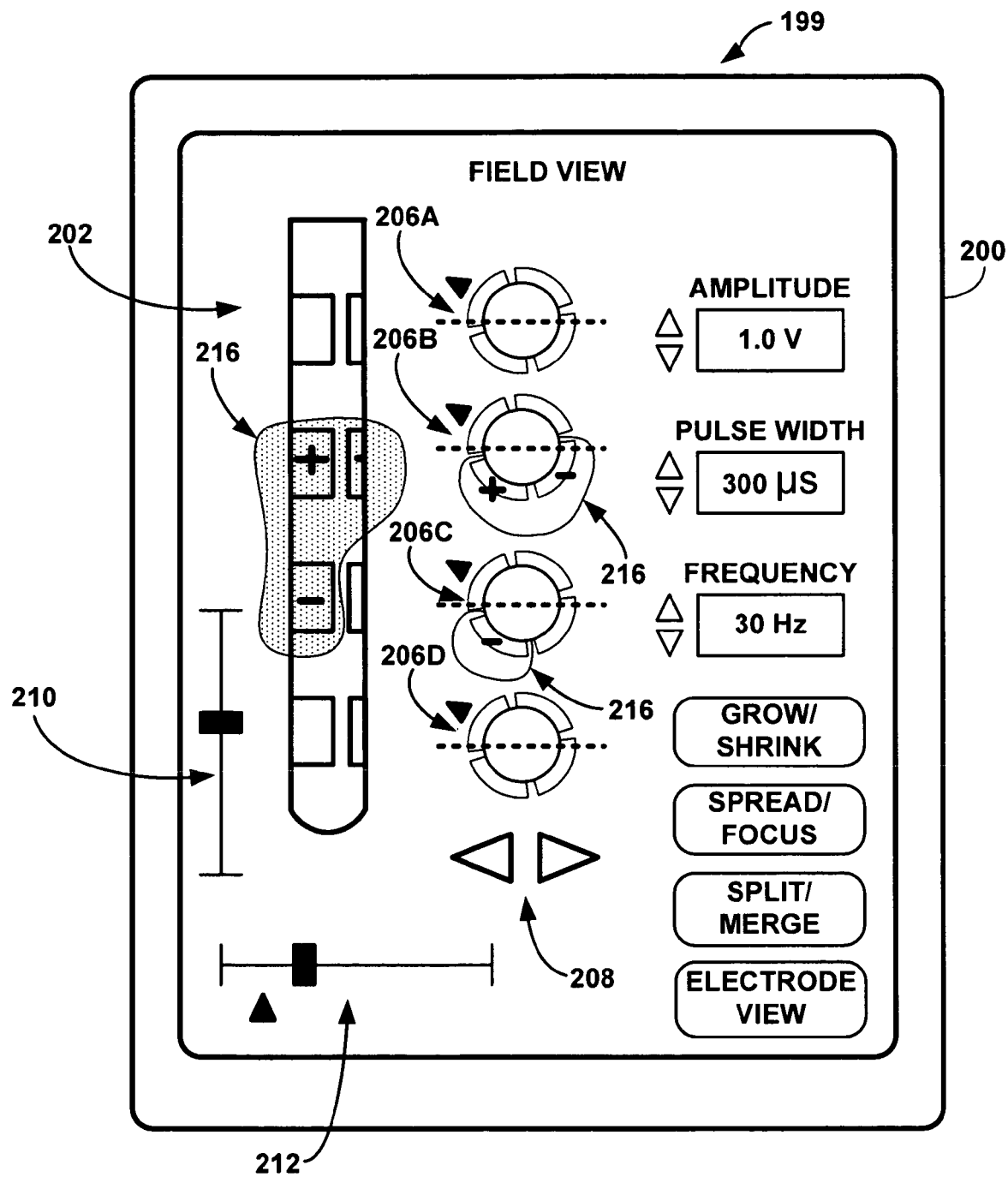

FIG. 14 illustrates user interface 199 of FIG. 13 upon vertical movement of stimulation field 216 instead of using scroll bar 210. Initially, stimulation field 216 is produced by an electrode combination positioned at levels 3 and 4 of the lead. The user moves stimulation field 216 upward by dragging the block in the scroll bar upward. In response, programmer 200 moves the stimulation field 216 upward so that it is produced by an electrode combination positioned at electrode levels 2 and 3 of the lead. The movement of stimulation field 216 is visible not only in side view 202, but also in cross-sectional views 206, which also show the stimulation field changing between electrode levels as it moves upward. For example, stimulation field 216 is initially shown in cross-sectional views 206C, 206D, corresponding to electrode levels 3 and 4, and then moves to cross-sectional views 206B, 206C.

Figure 15:
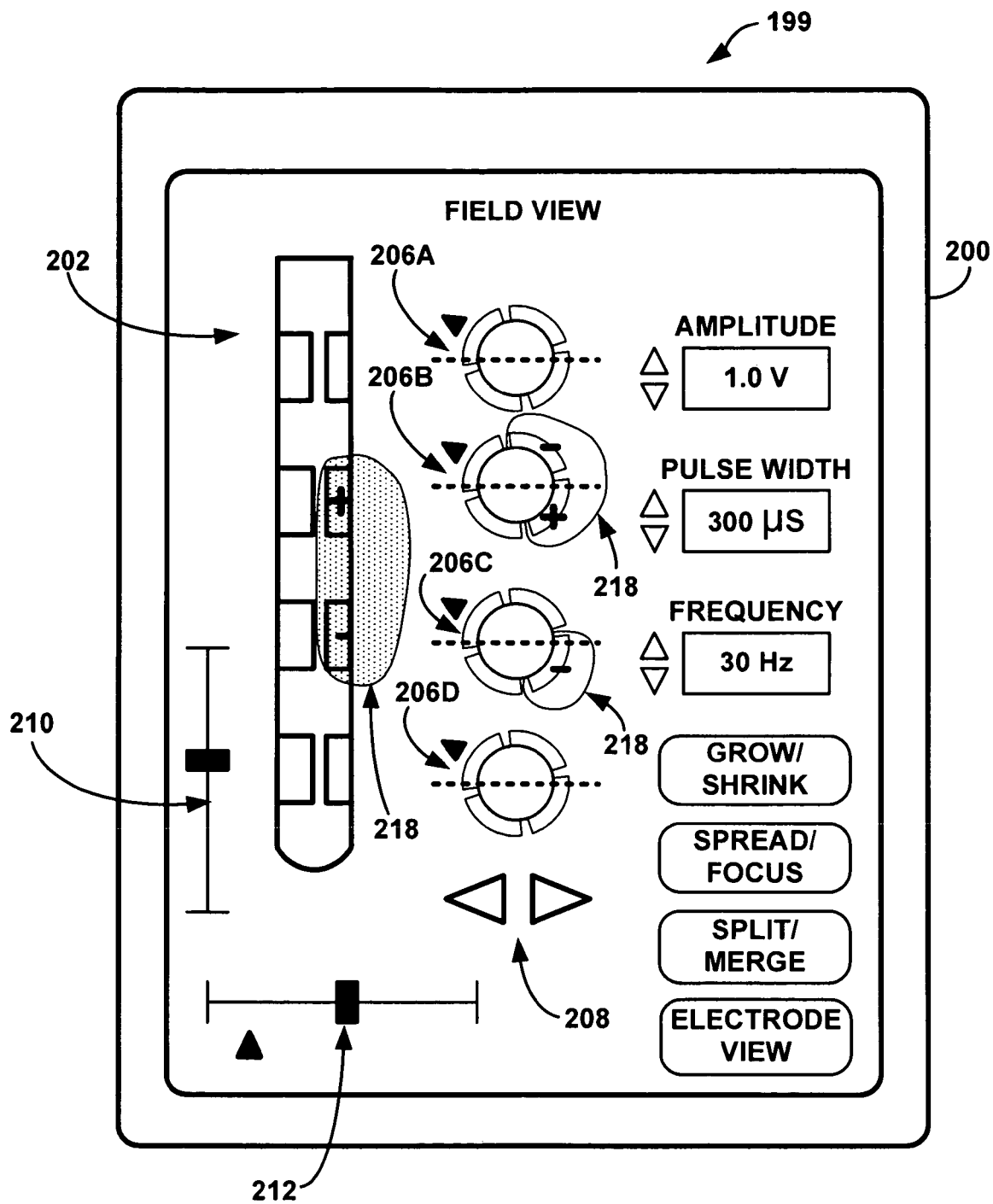

FIG. 15 generally corresponds to FIG. 14, but illustrates rotational movement of stimulation field 218. In the example of FIG. 15, a user moves the horizontal scroll bar 212 to rotate stimulation field 218 around the circumference of the lead. As shown in FIG. 15, the movement of stimulation field 218 is from left to right in side view 202 and counter-clockwise in cross-sectional views 206A-D. Again, programmer 200 responds to the rotational input entered by the user and automatically reconfigures the electrode combination and the stimulation parameter values to approximate stimulation field 218.

In the simple illustration of FIG. 15, stimulation field 218 rotates from electrodes at one set of angular positions to the electrodes at the next set of angular positions. In this example, the electrodes form quadrants, and stimulation field 218 moves from one quadrant to the next in a counter-clockwise direction in response to user input. However, the rotational movement need not span an entire quadrant. In some cases, the user may move stimulation field 218 such that it extends across adjacent quadrants, and programmer 200 adjusts the stimulation energy delivered by both quadrants to approximate the position of the stimulation field 218.

Rotational movement of stimulation field 218 is achieved by horizontal scroll bar 212, or other suitable input media, but rotational movement of the side and cross-sectional views may be accomplished by arrows 208. In particular, the user can press the left or right arrow 208 to rotate side view 202 in the pertinent direction and thereby view electrodes that otherwise are not visible in the two-dimensional representation of the lead.

Figure 16:
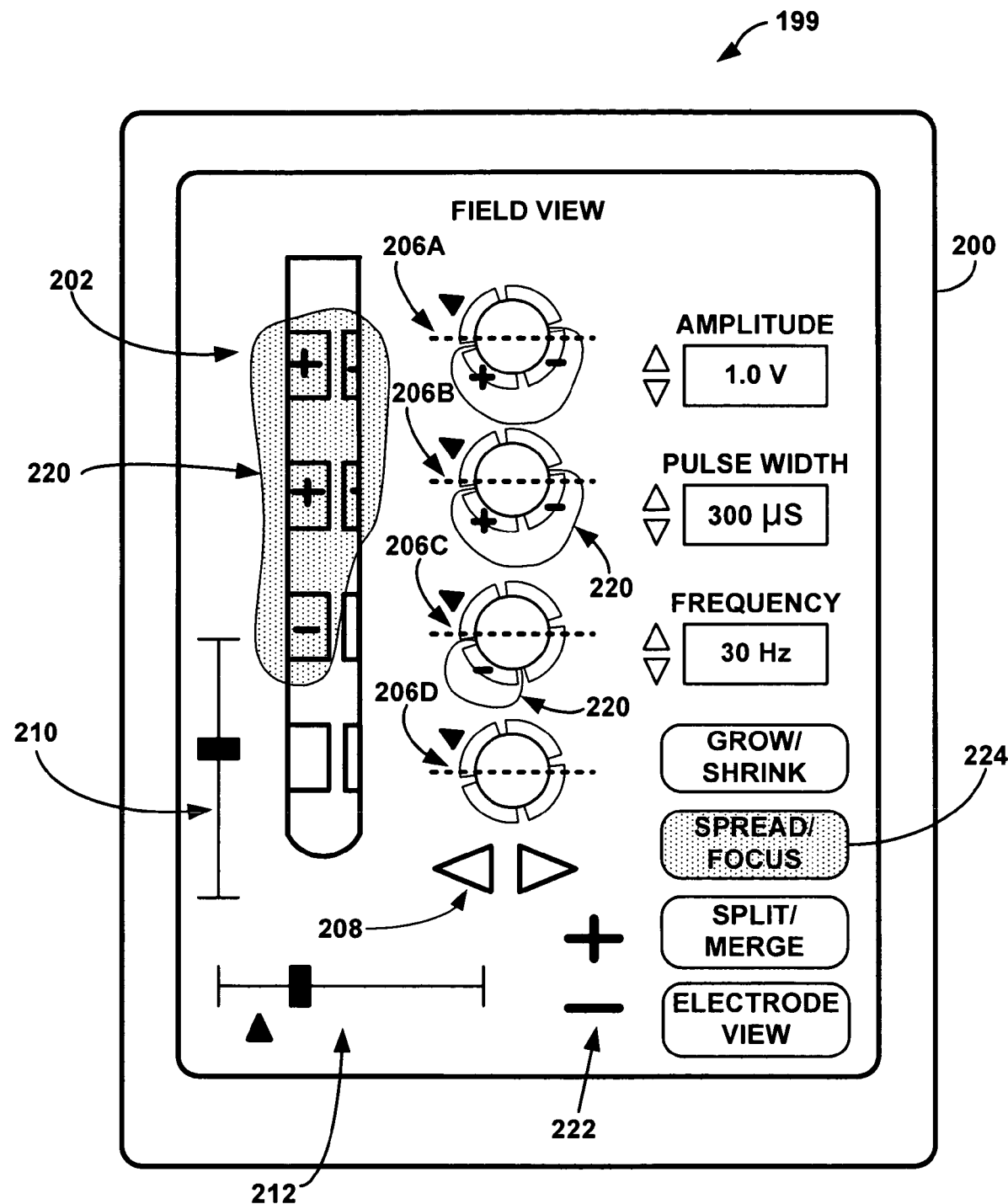

FIG. 16 corresponds substantially to FIGS. 11-15, but illustrates selection of a spread/focus command. Upon selection of the spread/focus command 224, the user may add additional electrodes to the current electrode combination, i.e., spread, or remove electrodes from the current electrode combination, i.e., focus. Upon selection of the spread/focus command 224, user interface 199 may display plus (+) and minus (−) input buttons. Using the plus/minus buttons 222, user increases or decreases, respectively, the number of electrodes in the current combination, thereby spreading or focusing stimulation field 220. The spreading and focusing may generally be configured to enlarge or shrink stimulation field 220 by addition or subtraction of electrodes, but preserve the vertical/horizontal/angular aspect ratios of the stimulation field.

The spread/focus command 224 may result in changes in the stimulation parameter values. For example, when stimulation field 220 spreads, the amplitude for each electrode may be reduced such that the overall amplitude remains substantially the same. Similarly, upon focusing stimulation field 220 to a smaller number of electrodes, the amplitude for each electrode may be increased. Alternatively, or additionally, pulse rate or pulse width may be increased or decreased as need to approximate the stimulation field specified by the user.

Figure 17:
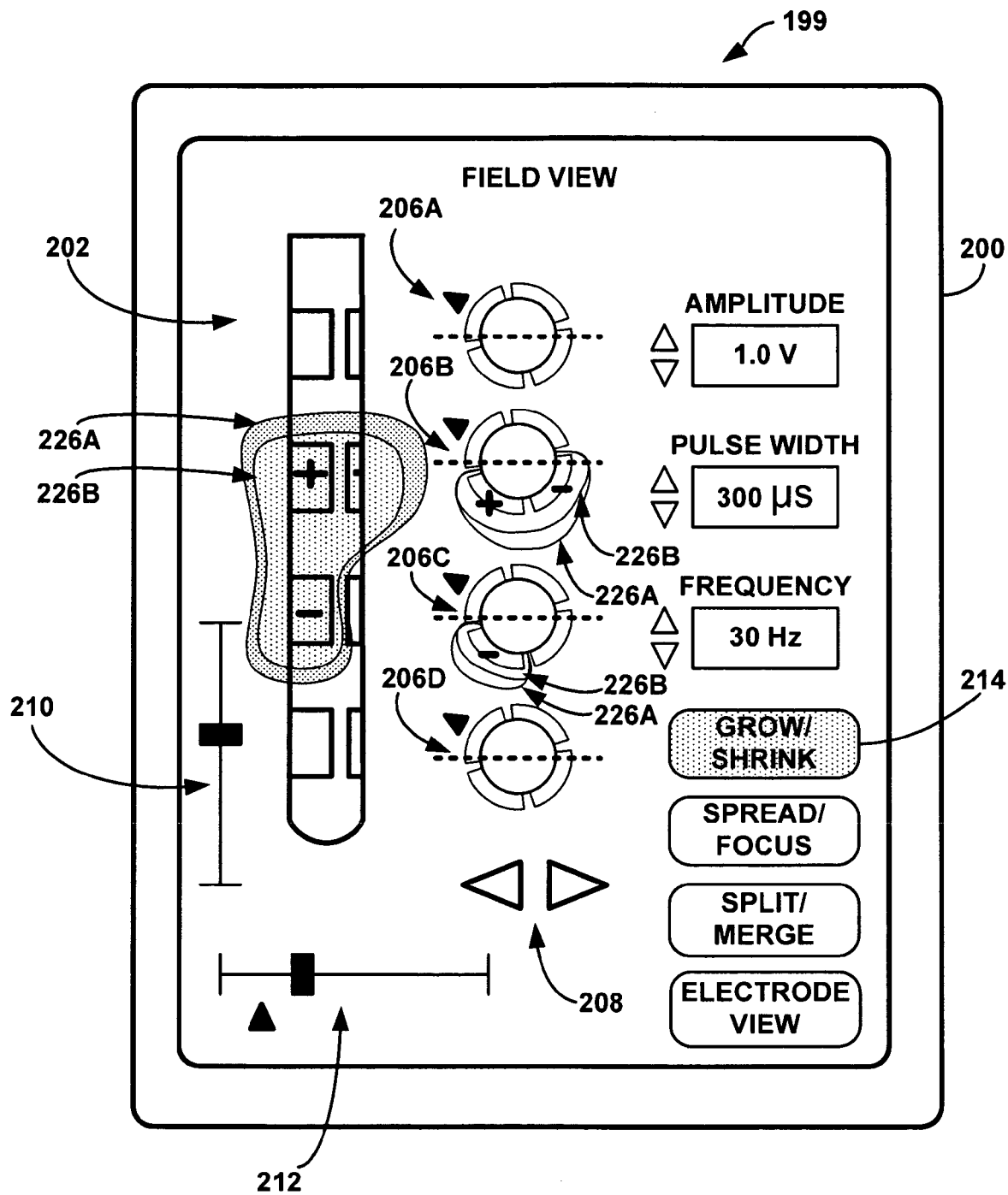

FIG. 17 substantially corresponds to FIG. 13, but illustrates both vertical movement of stimulation field 226 using vertical scroll bar 210 and growing of the field from initial stimulation field 226B to an expanded stimulation field 226A. In particular, stimulation field 226 is moved upward from electrode levels 3 and 4 (FIG. 13) to electrode levels 2 and 3, and expanded from field 226B to stimulation field 226A, all of which is visible in both side view 202 and cross-sectional views 206A-206D. When a user selects grow/shrink button 214, plus (+) and minus (−) input buttons or other media may be displayed by programmer 20 to permit selective growing or shrinking of the stimulation field 226.

Figure 18:
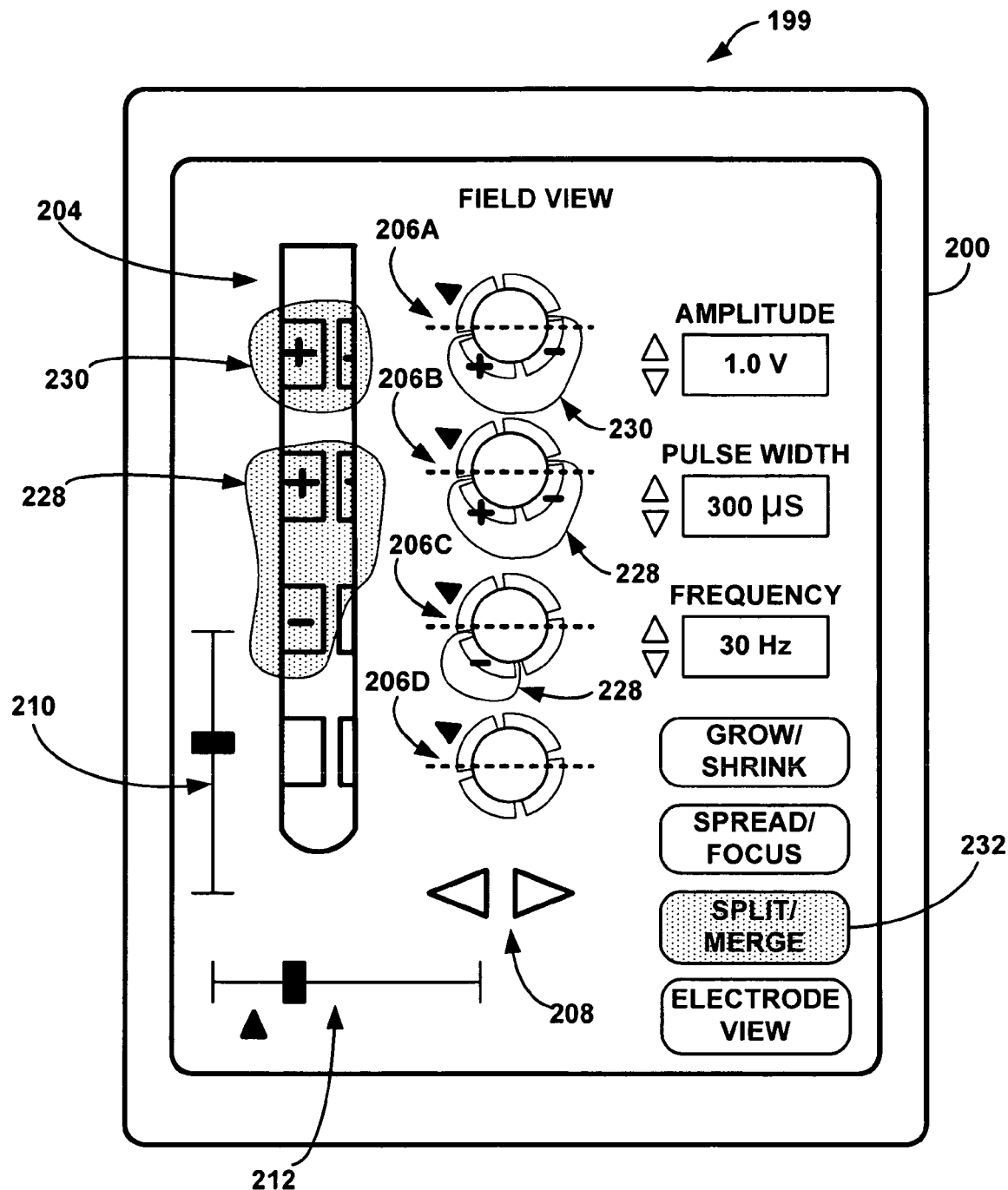

FIG. 18 illustrates a split/merge function in which user interface 199 permits a user to split a field into two separate fields or merge two separate fields into a single field. For example, to split a field, the user may click on the split/merge button 232 once, in which case programmer 200 divides the electrode combination into two separate electrode combinations and apportions parameter values between the electrode combinations to apply two distinct stimulation fields 228 and 230. Upon clicking split/merge button 232 twice, programmer 200 rejoins two or more separate electrode combinations and reconfigures stimulation parameters to form a single electrode combination that delivers a single stimulation field.

Figure 19:
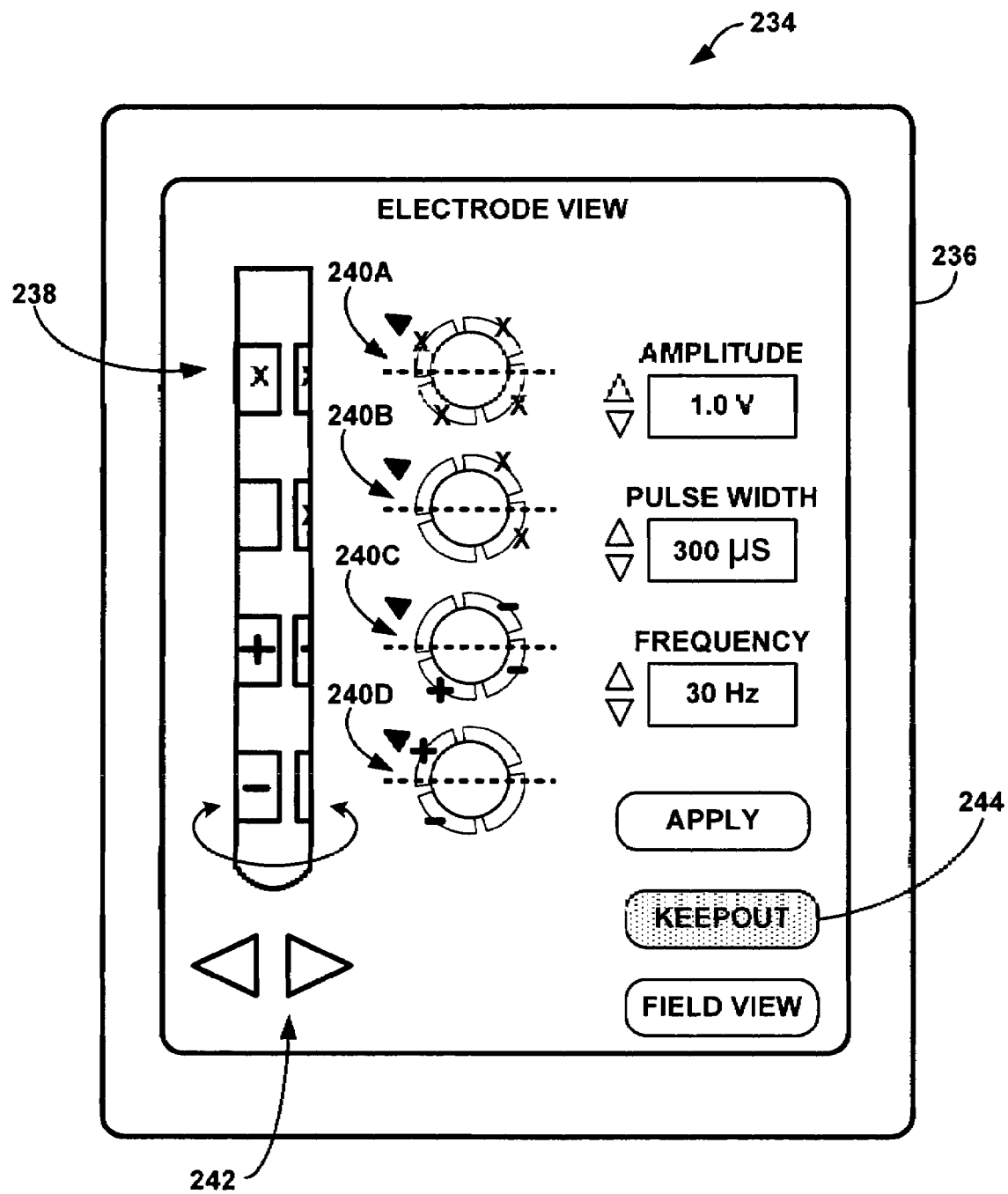

FIG. 19 illustrates an example embodiment in which user interface 234 permits the user, particularly the physician, to specify "keepout" regions in the electrode view. User interface 234 is an embodiment of user interface 98 and programmer 236 is an embodiment of programmer 19. For example, the physician may mark individual electrodes with an X on side view 238 and cross-sectional views 240A-D to specify that programmer 236 should not change settings for those electrodes. In some cases, the keep out electrodes may be near a sensitive anatomical structure. Accordingly, it may be desirable to prevent the physician or the patient from delivering stimulation via those electrodes. As another example, it may be desirable to prevent modification of stimulation settings associated with a particular electrode or set of electrodes so that a minimum or baseline level of stimulation is always delivered to the patient. In DBS, for example, sudden cessation of stimulation may cause adverse side effects. In other embodiments, the keepout regions may apply to ranges of stimulation parameter values, either globally or on an electrode-by-electrode basis. Such ranges may be specified using amplitude, pulse width and frequency controls illustrated in FIG. 19, or other similar control boxes for these stimulation parameters provided by a pop-up or the like. Alternatively, specific electrodes may be marked as keepout regions when an electrode is deemed unsafe for stimulation therapy. Unsafe electrodes may be determined by initial or periodic impedance tests of each electrode in which the impedance is above or below normal operating limits.

Figure 20:
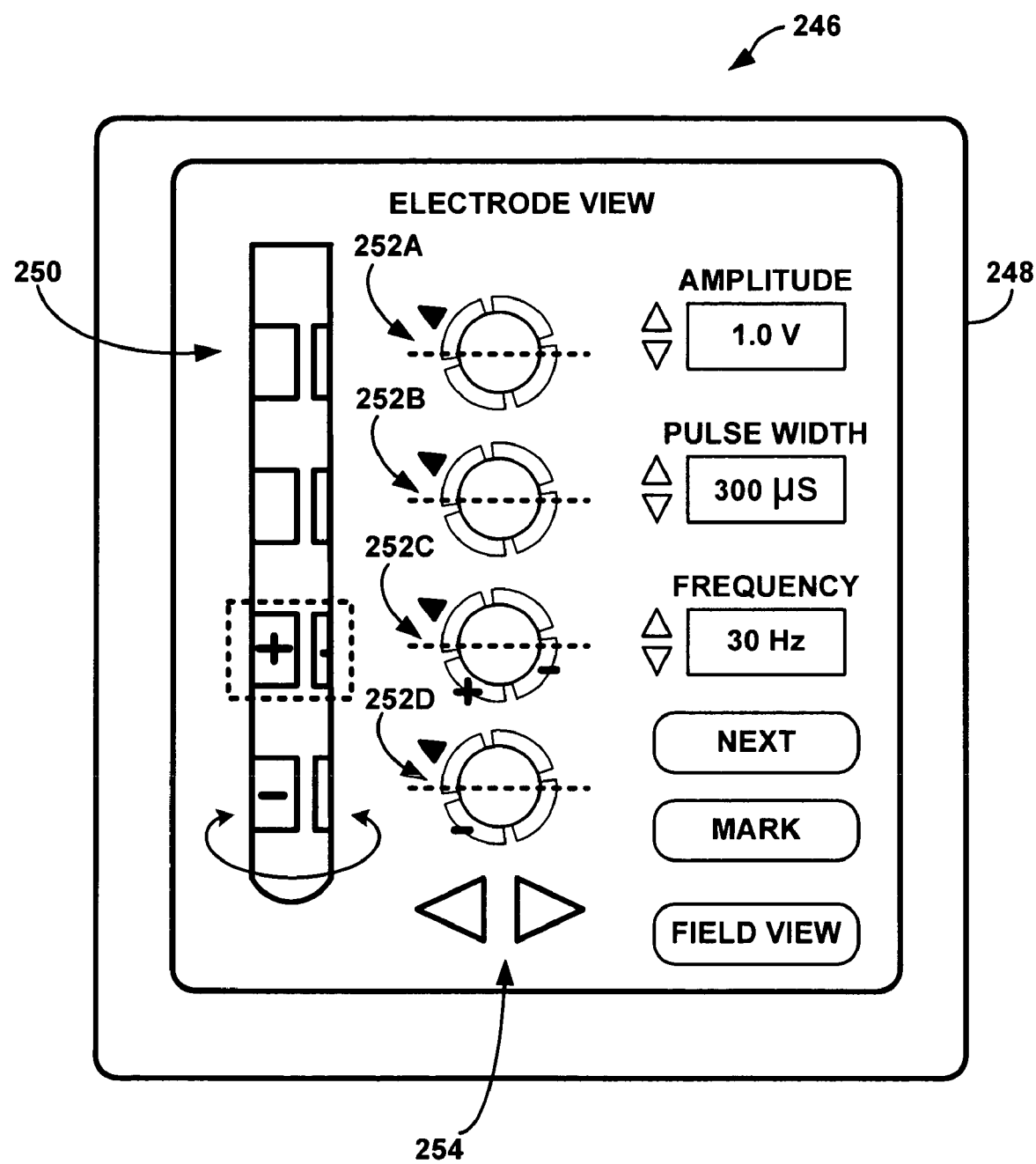

FIG. 20 is an example of a user interface presented by the programmer as part of a guided programming session. In this example, programmer 248 automatically selects or automatically proposes electrode combinations for evaluation by the user with user interface 246. Each time the user clicks on the "Next" button, programmer 248 presents another electrode combination. Programmer 248 may automatically select the electrode combination or present a prompt for user approval indicating that the electrode combination should be selected. User interface 246 is an embodiment of user interface 98 and programmer 248 is an embodiment of programmer 19.

For each electrode combination, the user may manually adjust parameter values or access the field view to manipulate the field. If a particular electrode combination is perceived to be efficacious, the user may click on the mark button. In response, programmer 248 records the electrode combination and associated parameter settings in the efficacy information 96 in memory 90 of FIG. 5 so that the user can later identify and retrieve programs that were observed to support therapeutic efficacy. In addition, programmer 248 may record user feedback information from each electrode combination in the form of subjective and/or objective feedback on therapy efficacy.

Figure 21:
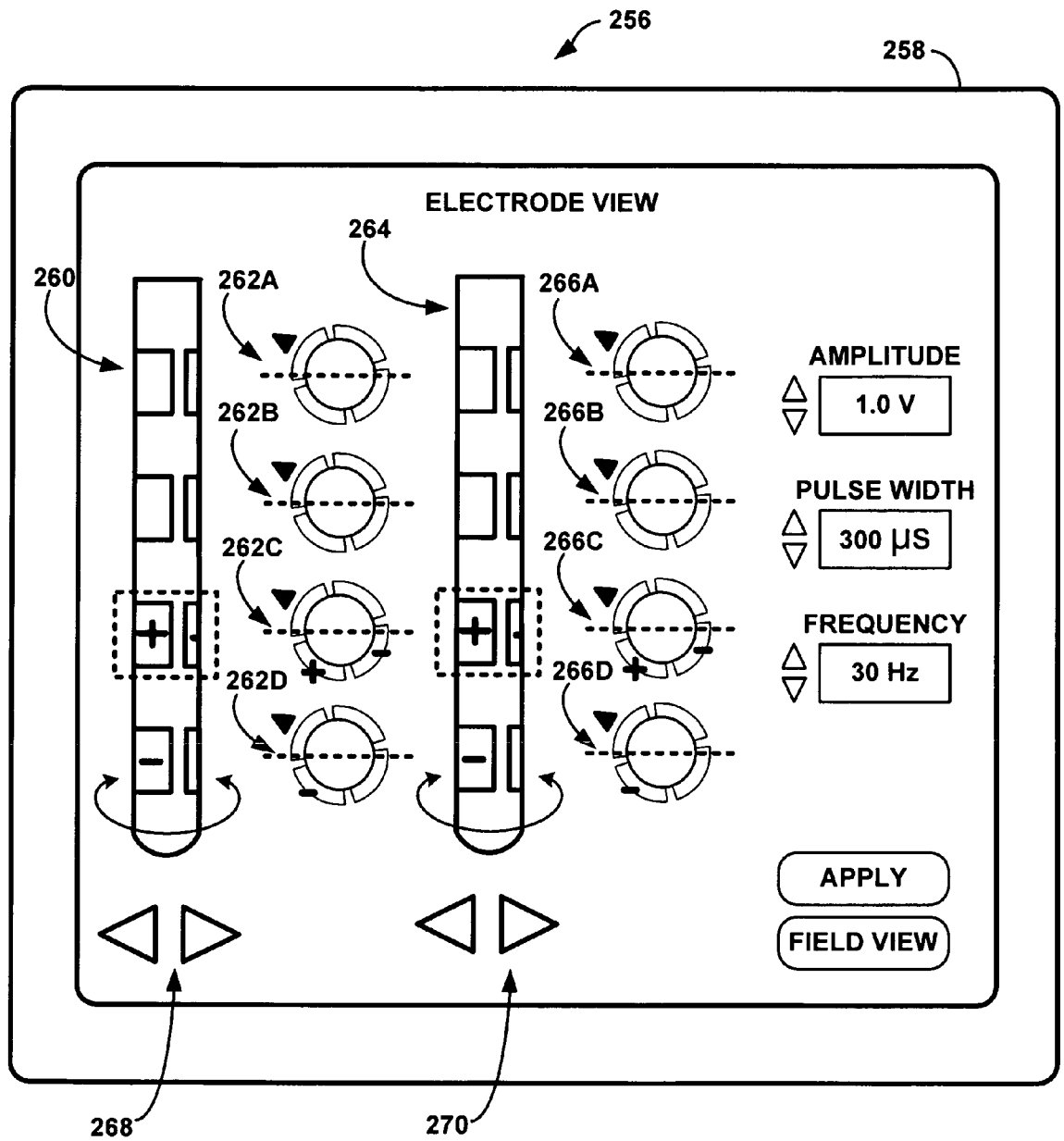

FIG. 21 generally corresponds to FIG. 6, but user interface 256 of programmer 258 presents two leads with associated side and cross-sectional views. User interface 256 shown in FIG. 21 may be useful, for example, in presenting combinations of multiple leads for bi-lateral DBS, spinal cord stimulation or other therapeutic applications. Arrows 268, 270, or similar input media, may permit the user to rotate side views 260 and 264 and cross-sectional views 262A-D and 266A-D to better observe the selected electrode combination. The field view may be selected to observe representations of stimulation fields produced by the selected electrode combination. User interface 256 is an embodiment of user interface 98 while programmer 258 is an embodiment of programmer 19.

Figure 22:
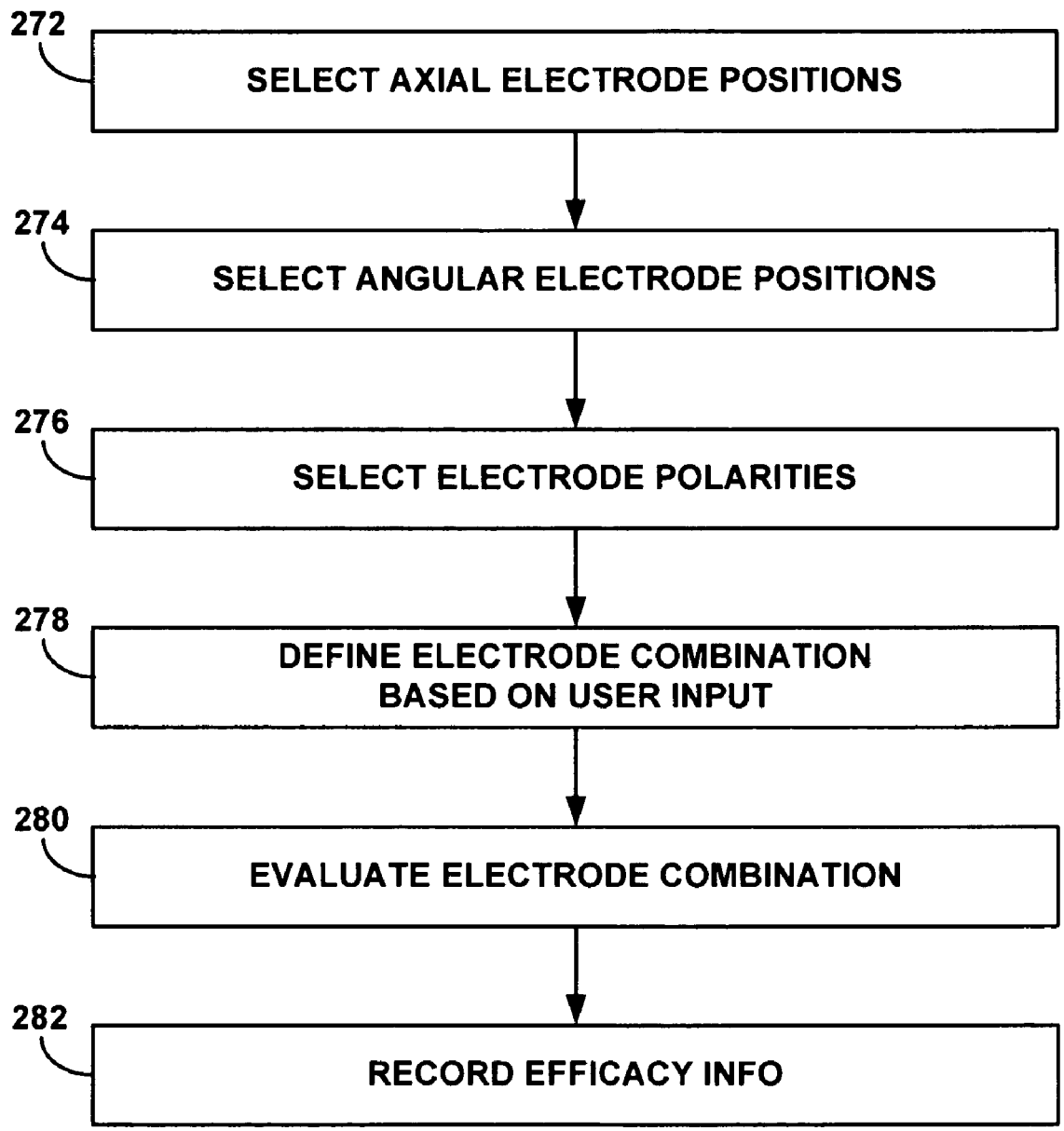
FIGS. 22-25 are flow diagrams illustrating example operation of the programmer of FIG. 5.

FIGS. 22-25 are flow diagrams illustrating example operation of a programmer. Although described with reference to programmer 19 of FIG. 5 and user interface 98, the techniques may be employed by any of the example programmers and user interfaces described herein. FIG. 22 generally illustrates a process for selecting electrode combination in a lead having a complex electrode array geometry. A user selects an axial electrode position (272), e.g., using the electrode view of user interface 98 or any embodiments thereof as described herein. The axial electrode position identifies an electrode level at one of several axial positions along the length of a distal portion of the lead. Upon identifying an axial position, the user selects an angular electrode position (274). The angular electrode position may selected by clicking on an electrode at the desired electrode level, either via the side view or the cross-sectional view. In the cross-sectional view, any of the electrodes may be readily selected. In the side view, it may be necessary to rotate the lead within user interface 98 to view a desired electrode to be selected. In some embodiments, a concentric axial view may be used instead of the cross-sectional view or an unwrapped 2D array view may be used instead of the side and cross-sectional view.

For one or more electrodes, specified by axial and angular position, the user selects the polarities of the electrodes such that the electrodes are designated as either a cathode or an anode (276). Programmer 19 defines the electrode combination (278) based on the selected axial positions, angular positions and polarities, and evaluates the electrode combination by applying stimulation to patient 12 via the electrode combination using parameter values selected or approved by the user (280). Upon application of the stimulation, the user may enter efficacy information, which programmer 19 records in memory 90 for later identification and retrieval (282).

Figure 23:
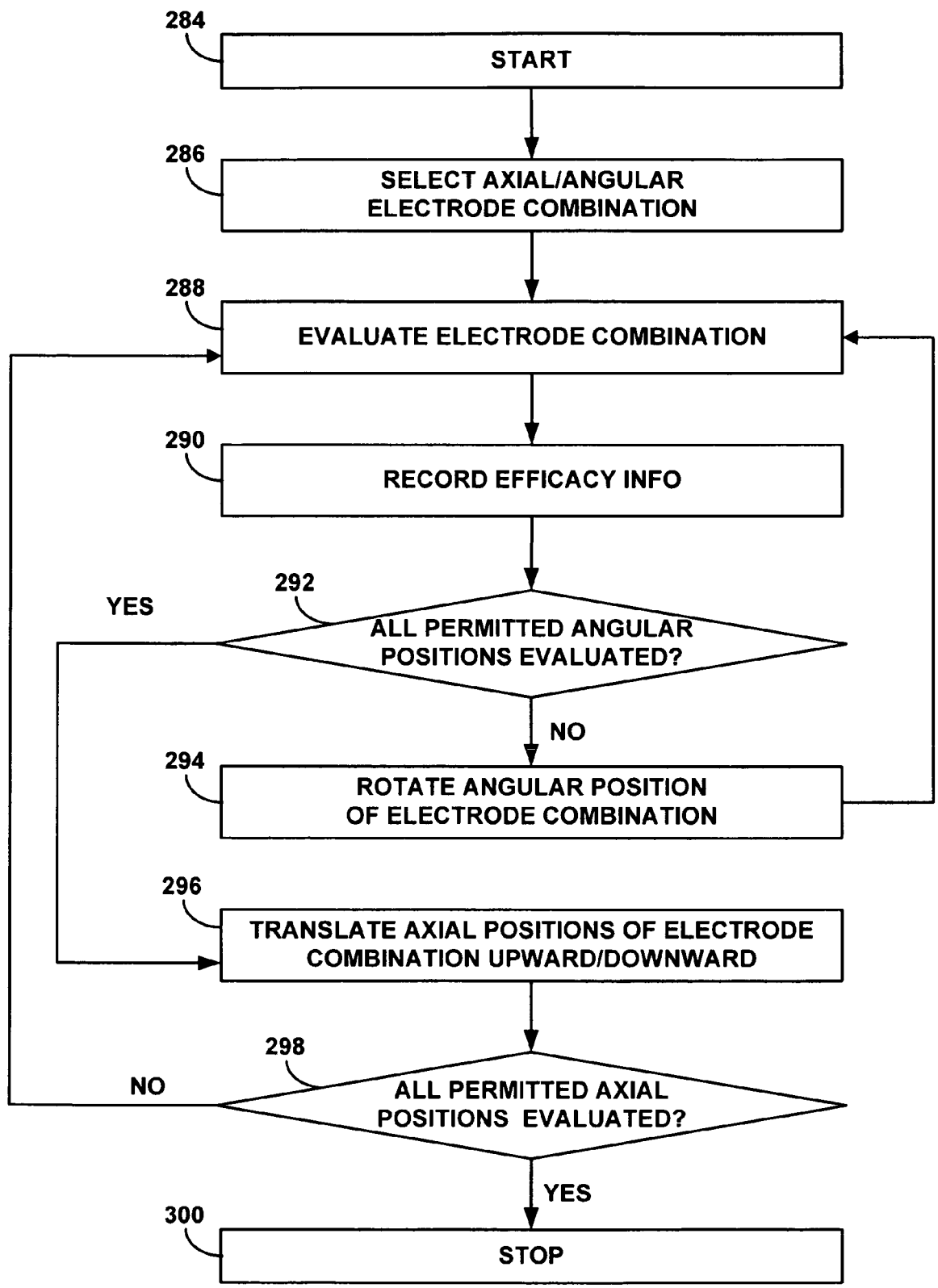

FIG. 23 shows a process for selecting and evaluating electrode combinations on a lead having a complex electrode array geometry. As shown in FIG. 23, via user interface 98 or other similar user interface as described herein, the user starts the selection process (284) and selects initial axial and angular positions of electrodes to form an initial electrode combination (286). The axial and angular positions may result in selection of multiple electrodes at a single axial electrode level or two or more different axial electrode levels. The initial electrode combination may be manually selected by the user, or recommended by programmer 19, e.g., according to a predetermined or dynamically generated evaluation sequence.

Upon selection of the initial electrode combination, programmer 19 instructs implantable stimulator 20 to apply stimulation energy via the selected combination. The user evaluates the electrode combination (288) and records efficacy information via user interface 98 (290). The efficacy information may be obtained by observation of patient 12 or by verbal or other feedback provided by the patient. If not all permitted angular positions have been evaluated (292), programmer 19 rotates the angular position of the electrode combination (294), e.g., clockwise, and evaluates the next electrode combination (288).

This process may continue iteratively until all permitted angular positions have been evaluated. An angular position is "permitted" in the sense that the user is permitted to evaluate it. In some cases, a physician may restrict some angular positions from evaluation, e.g., by designating them as keepout regions if adverse side effects could result due to stimulation of sensitive anatomical structures.

Once all angular positions have been exhausted, i.e., all permitted electrodes at different angular positions around the circumference of the lead have been tested (292), programmer 19 translates the axial position of the electrode combination upward or downward on the lead (296). At each axial position, programmer 19 repeats the process of evaluating different angular positions. The process ends when all permitted axial positions have been evaluated (298), or when a user otherwise wants to quit the process by stopping the process (300).

Figure 24:
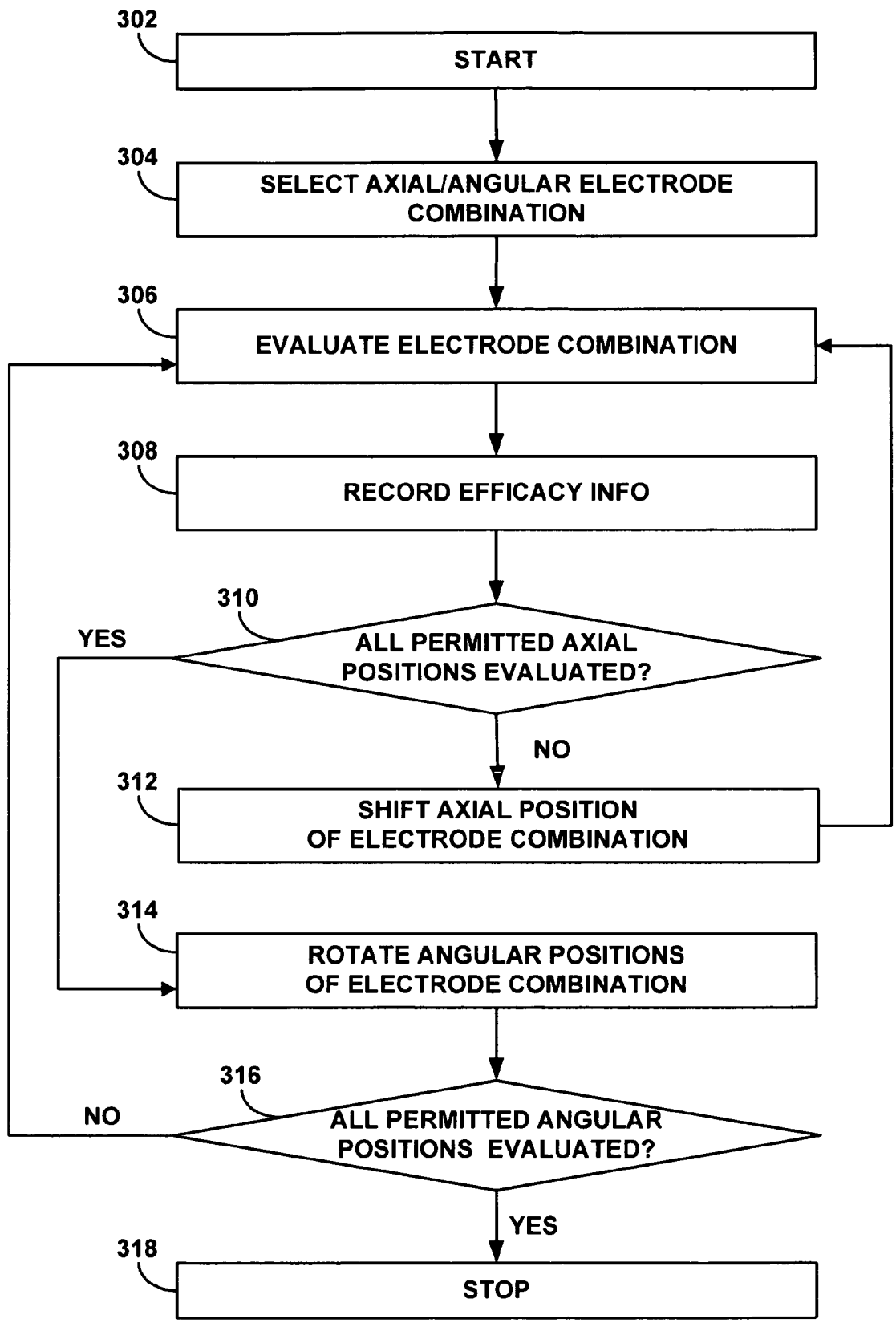

FIG. 24 illustrates a process similar to FIG. 23. However, axial positions are evaluated for different angular combinations. Hence, the process of FIG. 24 represents the opposite of the process of FIG. 23. In FIG. 24, via user interface 98 or other user interface described herein, the user starts the process (302) by selecting initial axial and angular positions of electrodes to form an initial electrode combination (304). Upon selection of the initial electrode combination, a programmer, e.g., programmer 19, instructs implantable stimulator 20 to apply stimulation energy via the selected combination. The user evaluates the electrode combination (306) and records efficacy information (308). Again, the efficacy information may be obtained by observation of patient 12 or by verbal or other feedback provided by the patient. If not all permitted axial positions have been evaluated (310), programmer 19 translates the axial position of the electrode combination, e.g., upward or downward (306), and evaluates the next electrode combination (306).

This process may continue iteratively until all permitted axial positions have been evaluated. An axial position is "permitted" in the sense that the user is permitted to evaluate it. In some cases, as in the example of FIG. 23, a physician may restrict some axial positions from evaluation, e.g., by designating them as keepout regions if adverse side effects could result due to stimulation of sensitive anatomical structures.

Once all axial positions have been exhausted (310), i.e., all permitted electrodes at different axial positions along the length of the lead have been tested, programmer 19 rotates the angular position of the electrode combination around the circumference of the lead (314). At each angular position, programmer 19 repeats the process of evaluating different axial positions (316). The process ends when all permitted angular positions have been evaluated (318).

Figure 25:
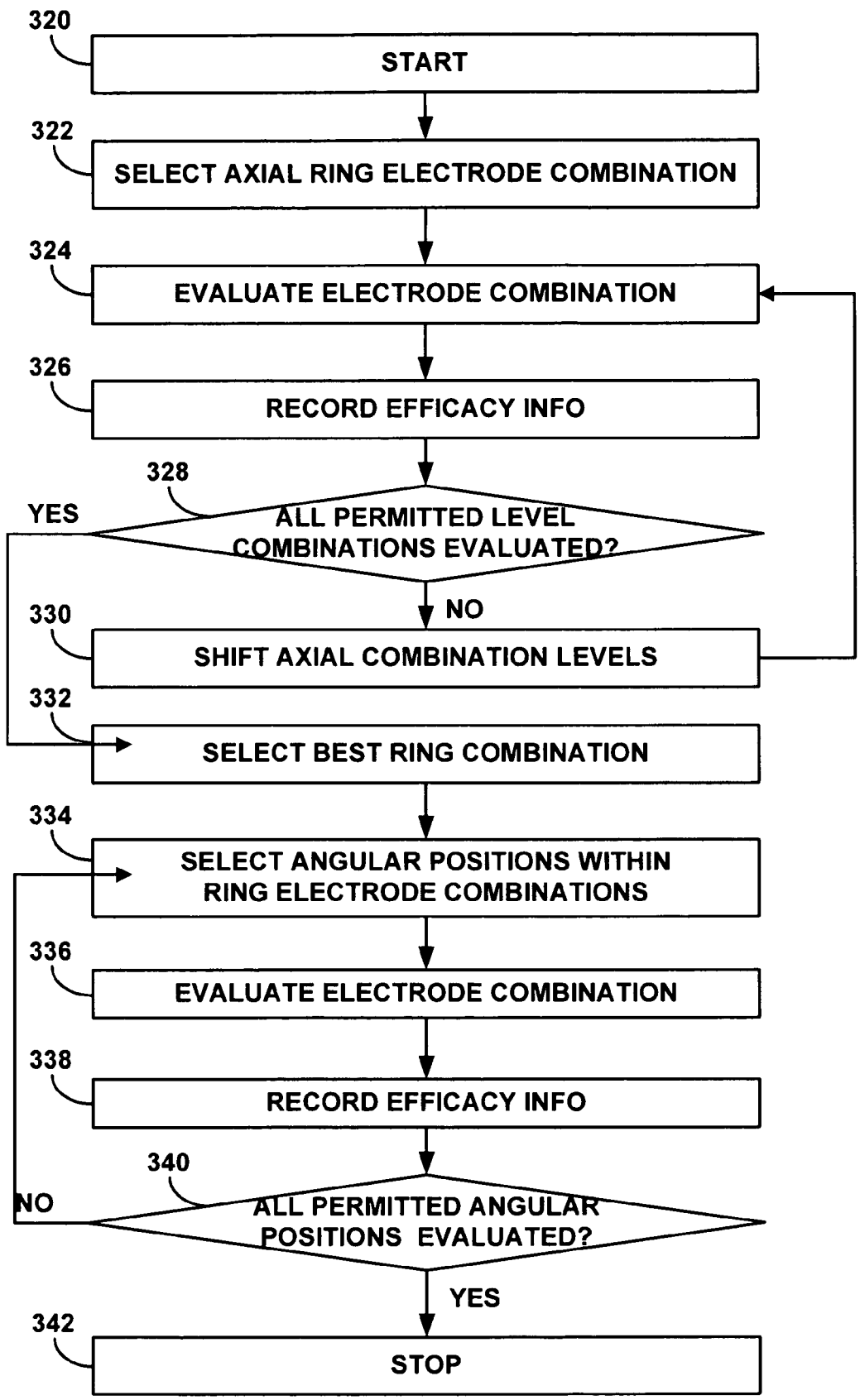

FIG. 25 shows another process for evaluating electrode combinations on a lead with a complex electrode array geometry. In the example of FIG. 25, the process starts (320) by selecting axial ring electrode combinations (322) and evaluating these electrode combinations made up of entire rings of electrodes disposed at different axial electrode levels. In this initial part of the process, programmer 19, or any other programmer described herein, treats the lead as if it were a conventional lead with ring electrodes. Alternatively, unipolar electrode rings may be activated and evaluated in addition to or instead of bipolar electrode rings.

Each electrode at a different angular position in a particular electrode level is activated simultaneously as if they formed a single ring electrode. Programmer 19 selects two or more electrode "rings" and evaluates stimulation efficacy. Programmer 19 selects additional rings, e.g., moving up and down the lead, until a "good" combination is found. This process results in a coarse tuning of the stimulation. Then, programmer 19 evaluates different angular positions of electrodes within that combination to fine-tune the stimulation.

As shown in FIG. 25, programmer 19 first selects an axial ring electrode combination. As an illustration, it is assumed that the lead includes four axial electrode levels, each including four electrodes at different angular positions around the lead circumference. An example of an axial ring electrode combination is the combination of all electrodes at electrode level 1 and all electrodes at another level such as electrode level 2, level 3 or level 4, producing, in effect, a combination of two or more ring electrodes. Alternatively, programmer 19 may also Programmer 19 directs the stimulator to deliver stimulation energy via the selected axial ring electrode combination. The user evaluates the electrode combination (324) and records efficacy information in programmer 19 (326). If not all permitted ring combinations have been evaluated (328), programmer 19 shifts the axial ring combination upward or downward on the lead, or otherwise selects a different axial ring combination (330).

For example, programmer 19 may shift a ring combination of level 1 and level 2 downward to produce a new combination of level 2 and level 3. However, programmer 19 may be configured to explore other possible combinations. For example, programmer 19 may shift a ring combination of level 1 and level 2 to a combination of level 1 and level 3, then level 1 and level 4, then level 2 and level 3, then level 2 and level 4, then level 3 and level 4, and so forth.

Upon evaluating each axial ring electrode combination and recording efficacy information, programmer 19 shifts to the next axial ring combination if not all of the permitted ring combinations have been evaluated. After all ring combinations have been evaluated (328), programmer 19 selects the best ring combination as a coarse tuning result (332), and then proceeds to fine tune the stimulation by evaluating different angular combinations.

In particular, upon selection of the "best" ring combination in terms of efficacy (or some other ring combination having at least acceptable efficacy), programmer 19 reduces the selected combination to a set of electrodes at one or more angular positions (334). For example, if the selected ring combination is a combination of all electrodes at levels 2 and 3, the programmer next selects individual electrodes at different angular positions in levels 2 and 3.

As an illustration, if the four electrodes in a level are numbered 1 through 4, the programmer may start with an electrode combination of level 1, electrode 1 and level 3, electrode 1. Upon evaluating the electrode combination (336) and recording efficacy information (338), programmer 19 selects another angular position with in the ring electrode combination. For example, the programmer may rotate the field to an electrode combination of level 1, electrode 2, and level 3, electrode 2. The process continues until all permitted angular positions have been evaluated (340). Then, the physician may stop the processor (342) and select one of the axial/angular electrode combinations to form a program for delivery of stimulation energy.

As a refinement to the process of FIG. 25, programmer 19 also may evaluate a plurality of different stimulation parameter settings for each axial ring electrode combination, each axial/angular combination, or both. In this manner, programmer 19 attempts to optimize the electrode positions and the stimulation parameter values delivered via the selected electrodes to provide overall efficacy.

Although the illustration above refers to the evaluation of individual electrodes at different angular positions, e.g., level 1, electrode 1, and level 3, electrode 1, each level may have more than one electrode activated at a time. For example, programmer 19 may not only evaluate individual angular positions, but also combinations of electrodes at angular positions. In particular, programmer 19 may evaluate a combination of axial level 1, electrodes 1 and 2 and axial level 3, electrodes 1 and 2, or any combination of electrodes in a given level, e.g., (a) 1 and 2, (b) 1 and 3, 1 and 4, (c) 2 and 3, (d) 2 and 4, (e) 3 and 4, (f) 1, 2, and 3, (g) 1, 2 and 4, (h) 1, 3 and 4, (i) 2, 3, and 4, and so forth. In some embodiments, each evaluation of one or more electrodes may comprise evaluation of the electrodes as cathodes in a bipolar configuration with one or more electrodes on the lead acting as an anode, or a monopolar configuration with an indifferent electrode, e.g., the housing of stimulator 20, acting as the anode.

Figure 26:
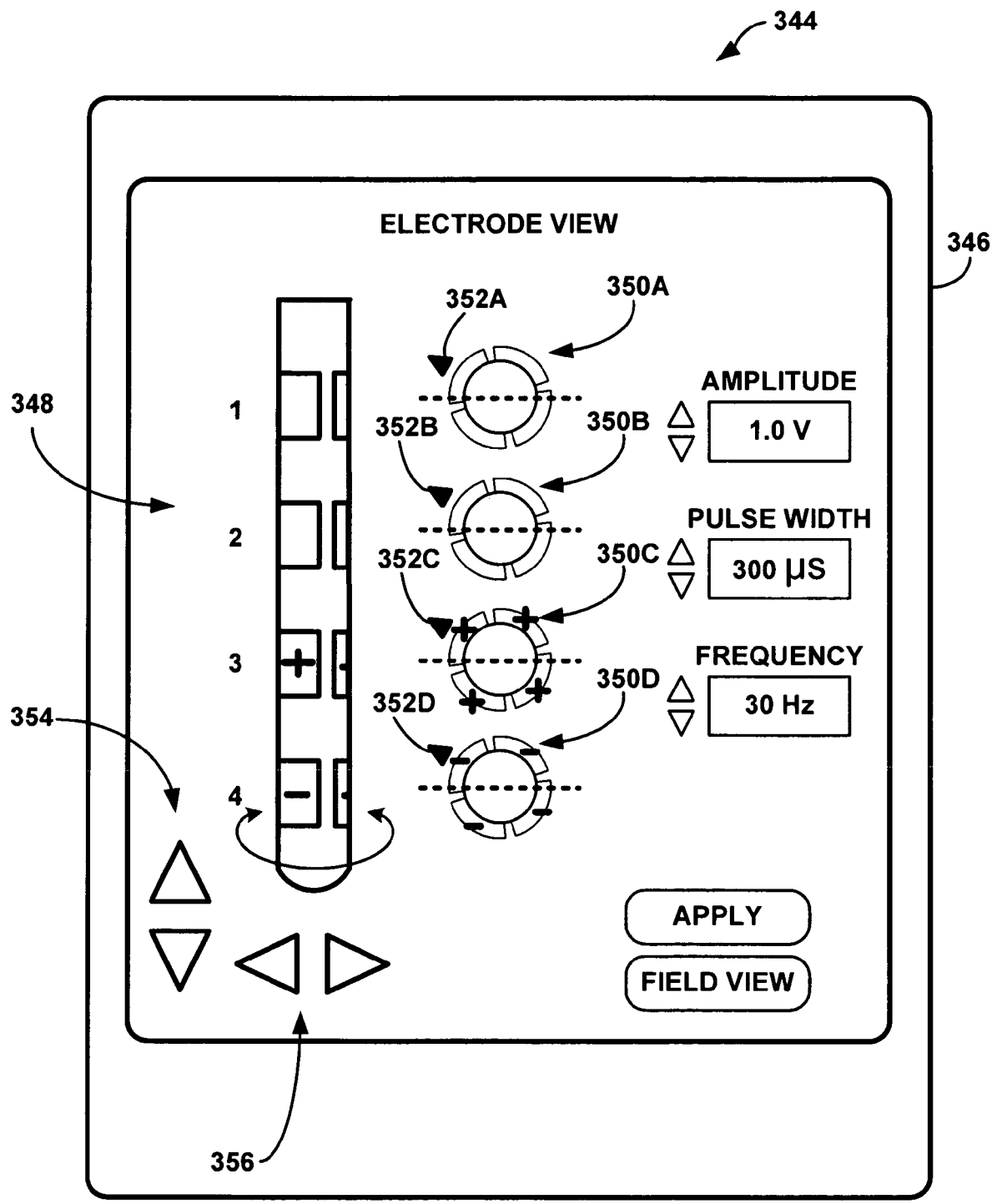
FIG. 26 is a diagram illustrating ring-based selection of axial positions on a lead having a complex electrode array geometry.

FIG. 26 is a diagram illustrating ring-based selection of axial positions on a lead having a complex electrode array geometry, as described in FIG. 25. An initial electrode combination may include a ring formed by all electrodes in a given level and all electrodes in another level. In the example of FIG. 26, as shown in side view 348 and cross-sectional views 350A-D, all electrodes at different angular positions in axial electrode level 3 are selected as "+" electrodes and all electrodes at different angular positions in axial electrode 4 are selected as "−" electrodes. Alternatively, unipolar electrode rings may be selected, e.g., only one anode or cathode ring. The opposite pole may be a specific electrode or the conductive housing of stimulator 12.

FIGS. 27 and 28 are diagrams illustrating selection of different electrode combinations on a lead having a complex electrode array geometry using guided evaluation sequences. The two-dimensional array shown in FIGS. 27 and 28 represents all of the axial and angular positions of electrodes on a lead having four electrode levels and four angular positions, resulting in a four-by-four array of possible electrodes.

FIG. 27 further illustrates the ring-based coarse tuning of stimulation described above with respect to FIGS. 25 and 26. Programmer 19 will be used as an example in FIGS. 27 and 28; however, any programmer described herein may be used in a similar manner. In FIG. 27A, programmer 19 initially evaluates effective ring electrodes formed by electrodes at all angular positions in electrode levels 1 and 2. In FIG. 27B, the axial ring combination is shifted to includes all electrodes in levels 2 and 3. In FIG. 27C, the axial ring combination is shifted to include all electrodes in levels 3 and 4.

Upon selecting one of the axial ring combinations, e.g., levels 2 and 3, programmer 19 rotates among different angular electrode positions to fine tune the electrode combination. In FIG. 27D, programmer 19 initially evaluates electrodes 2A and 3A, i.e., the electrodes in the first angular position in levels 3 and 4. In FIGS. 27E and 27F, programmer 19 rotates the field from 2A-3A to 2B-3B (FIG. 27E) and then from 2B-3B to 2C-3C (FIG. 27F).

Evaluation involves transmission of a program or instructions to the stimulator defining the electrode combination and associated parameter values, and activation of the stimulator to deliver stimulation energy according to the electrode combination and parameter values. This process shown in FIGS. 27A-27F may continue until several angular electrode combinations are evaluated for the selected axial ring combination. Again, the angular electrode combinations may include multiple electrodes in a given electrode level, and may explore all combinatorial possibilities or a subset of the possibilities. Ultimately, the physician selects one or more of the axial-angular combinations based on the evaluation and perceive efficacy.

FIGS. 28A-28F illustrate another guided evaluation sequence in which programmer 19 or the user specifies an initial axial/angular electrode combination, and the programmer selects additional electrodes to "orbit" around the initial electrode combination. In the example of FIG. 28A, an initial electrode combination of 2B−, 2C+ and 3C− is selected and evaluated by activating stimulation according to the specified electrode combination. Various stimulation parameter values may be adjusted and tested for the electrode combination. The user may record efficacy information via programmer 19.

Then, programmer 19 fine-tunes the electrode combination by "orbiting" around it. In the example of FIGS. 28A-28F, the 2C+ electrode serves as an anchor point, while the − electrodes are rotated around it. In particular, programmer 19 shifts from the initial combination (2B−, 2C+ and 3C−) to combinations of 2C+, 3B−, 3B− (FIG. 28B), 2C+, 2D−, 3C− (FIG. 28C), 1C−, 2C+, 2D+ (FIG. 28D), and 1C−, 2B−, 2C+ (FIG. 28E). In the example of FIG. 28F, upon orbiting around all positions of the electrode combination centered at 2C+, programmer 19 moves the anchor point to 3C+ and starts with 3B− and 4C− as the next initial electrode combination for the orbit process. While an anode is used as an example, a cathode may also be used as the anchor point in a similar manner.

The orbit process may continue across several different anchor points. For each anchor point and associated orbit, programmer 19 directs the stimulator to deliver stimulation via the specified electrode combination, permitting the user to evaluate and record stimulation efficacy. In some embodiments, the efficacy recorded for a particular electrode combination may be used to dynamically guide the orbit or the selection of anchor points. If anchor points 4A and 4B produce poor efficacy, for example, programmer 19 may avoid continued orbits in those areas of the electrode array geometry, and instead select different anchor points further away from those points.

Figure 29:
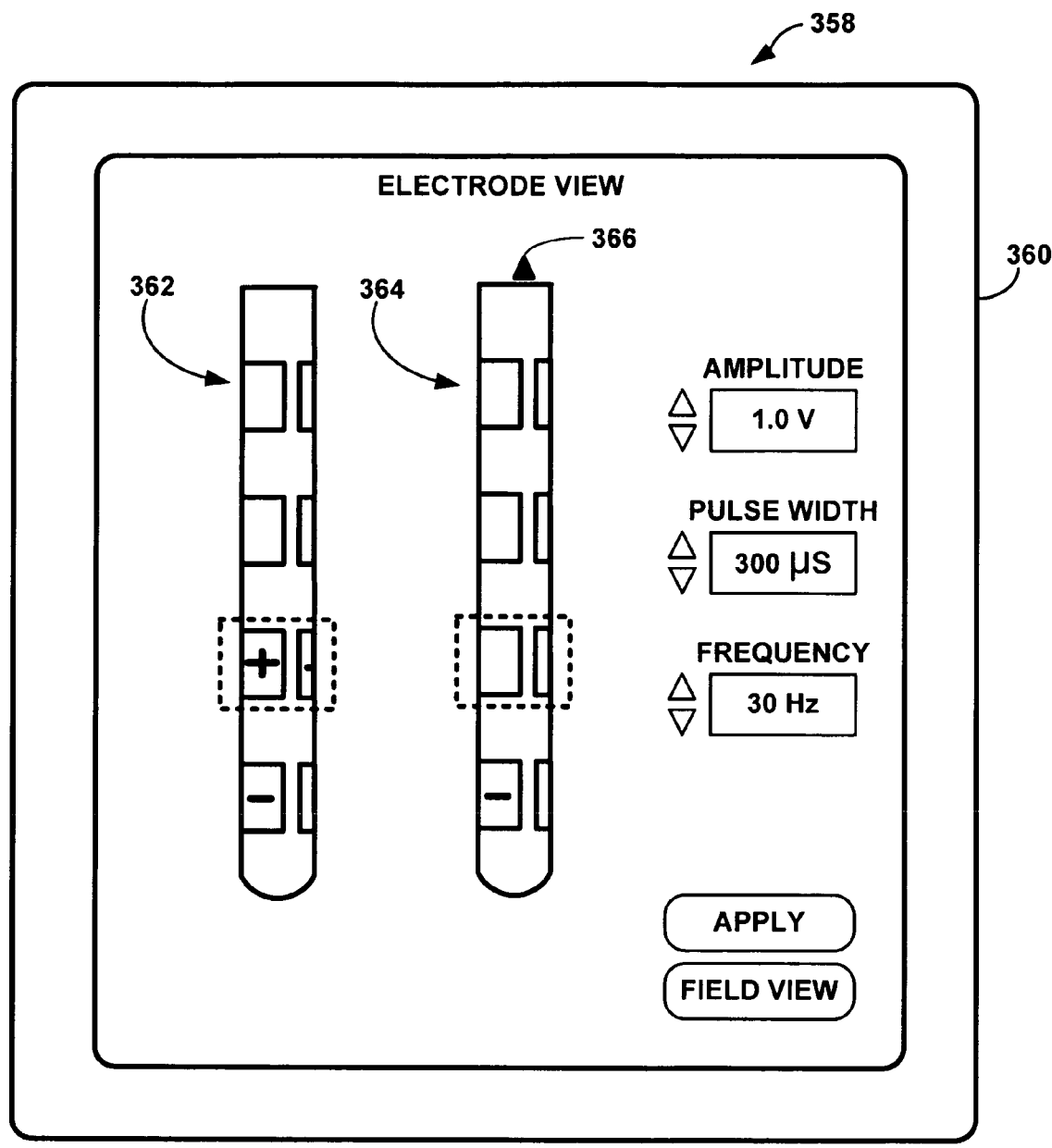
FIG. 29 is a diagram illustrating a user interface presenting two sides of a lead having a complex electrode array geometry.

FIG. 29 is a diagram illustrating a user interface present two side views 362 and 364 of one lead having a complex electrode array geometry. In the example of FIG. 29, user interface 358 of programmer 360 presents side view 362 and 364 of the two different sides of a single lead, so that all electrodes are simultaneously visible. For example, side view 362 shows a first 180 degree side of the lead while side view 364 shows a second 180 degree side of the lead. In some embodiments, side views 362 and 364 may be rotated to change the perspective of the lead. The electrodes may be selected using a stylus of other pointing device. In some embodiments, an orientation arrow 366 may be added to illustrate orientation of the lead relative to an anatomical structure. User interface 358 is an embodiment of user interface 98 and programmer 360 is an embodiment of programmer 19.

FIGS. 30A-D are conceptual diagrams of example cross-sections of stimulation templates stored for electrode combinations of two adjacent levels of a complex electrode array geometry. A stimulation template is a predetermined volumetric stimulation field that programmer 19 can use to match to a desired stimulation field from the clinician. The process of selecting one or more stimulation templates to generate stimulation parameters that fit the user defined stimulation field may be less computationally intensive for programmer 19 than using multiple equations or lookup tables to generate the stimulation parameters. The stimulation template may be a representation of an electrical field or other electrical stimulation related characteristic, e.g., current density, voltage gradient, or neuron activation, applied to a generic human tissue. In addition, the clinician may be able to switch between any of these representations when desired.

Cross-sections of example stimulation templates are provided to illustrate possible fields around the circumference of implanted lead 14. FIGS. 30A-D illustrate possible cross-sections of stimulation templates of an electrode of one electrode level paired to another electrode at another electrode level at the same circumferential position. Even through only cross-sections of stimulation templates are shown, they will be referred to as a stimulation template for simplicity. In some embodiments, programmer 19 may utilize stimulation templates to reduce the processing tasks of generating stimulation parameters for therapy. In this manner, programmer 19 may select one or more stimulation templates that best match the desired stimulation field. If only one electrode is chosen, at least one other electrode above or below the selected electrode must also be used to create the stimulation template. In other embodiments, similar stimulation templates may be created with complex electrode array geometries utilizing more or less than 4 electrodes in a give electrode level. The stimulation template may not indicate the exact shape of the resulting stimulation field, as the tissue adjacent to the electrode may affect the propagation of the electrical current.

Figure 30A:
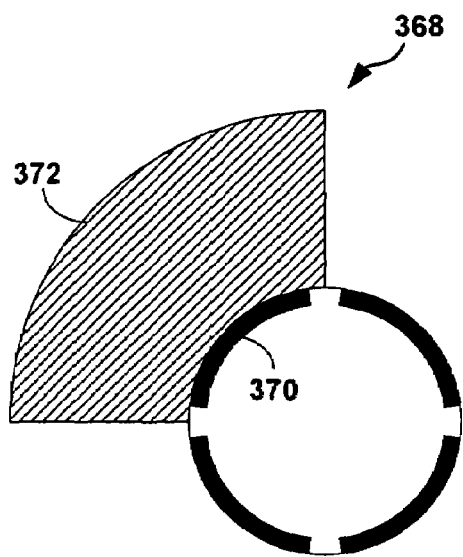
FIG. 30 is a conceptual diagram of example stimulation templates stored for electrode combinations.
Figure 30B:
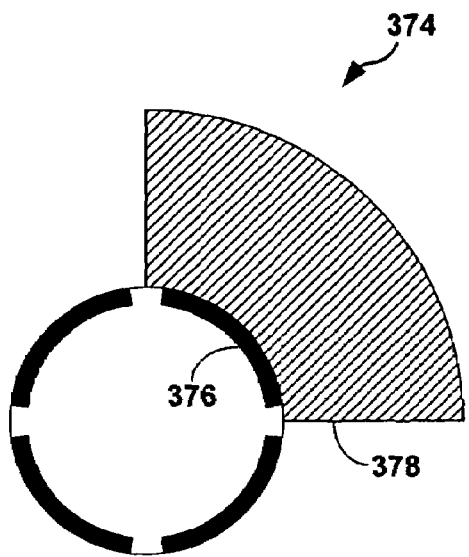
Figure 30C:
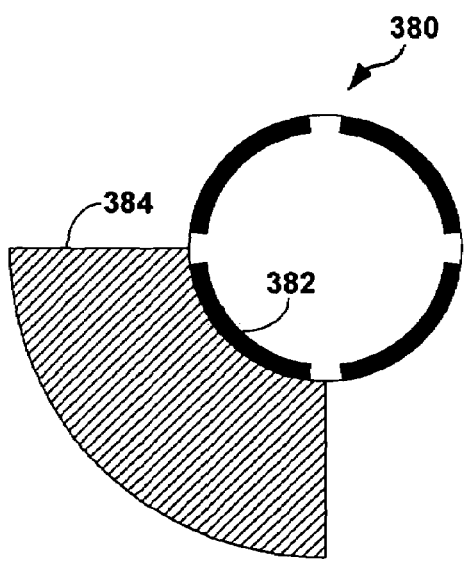
Figure 30D:
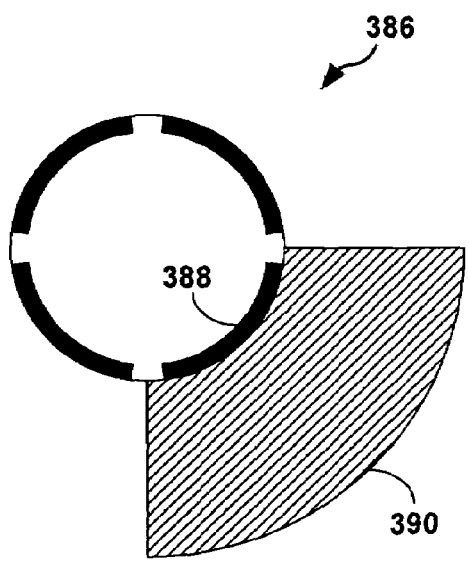

FIG. 30A shows electrode 370 and corresponding cross-section of idealized stimulation field 372 that creates stimulation template 368. FIG. 30B shows electrode 376 and corresponding cross-section of idealized stimulation field 378 that creates stimulation template 374. FIG. 30C includes stimulation template 380 which is created by electrode 382 and cross-section of idealized stimulation field 384 adjacent to the electrode. FIG. 30D indicates that stimulation template 386 is created from electrode 388 and cross-section of idealized stimulation field 386. The actual shape of each stimulation template may vary depending upon the surrounding tissue to the implanted lead. However, system 10 may use the idealized stimulation templates as approximate stimulation templates for the purpose of matching the best template to the user defined stimulation field. For all stimulation templates, programmer 19 may adjust the current amplitude or voltage amplitude to alter the size of the stimulation template to cover the desired stimulation field from the physician. In addition, programmer 19 may combine any of the stimulation templates 368, 374, 380 and 386 to stimulate tissue at desired locations around the lead. In some embodiments, the physician may have manual control to change the polarity of one or more electrode of a stimulation template such that the stimulation of the stimulation template set may be slightly changed to affect the therapy provided by the stimulation template set.

Figure 31:
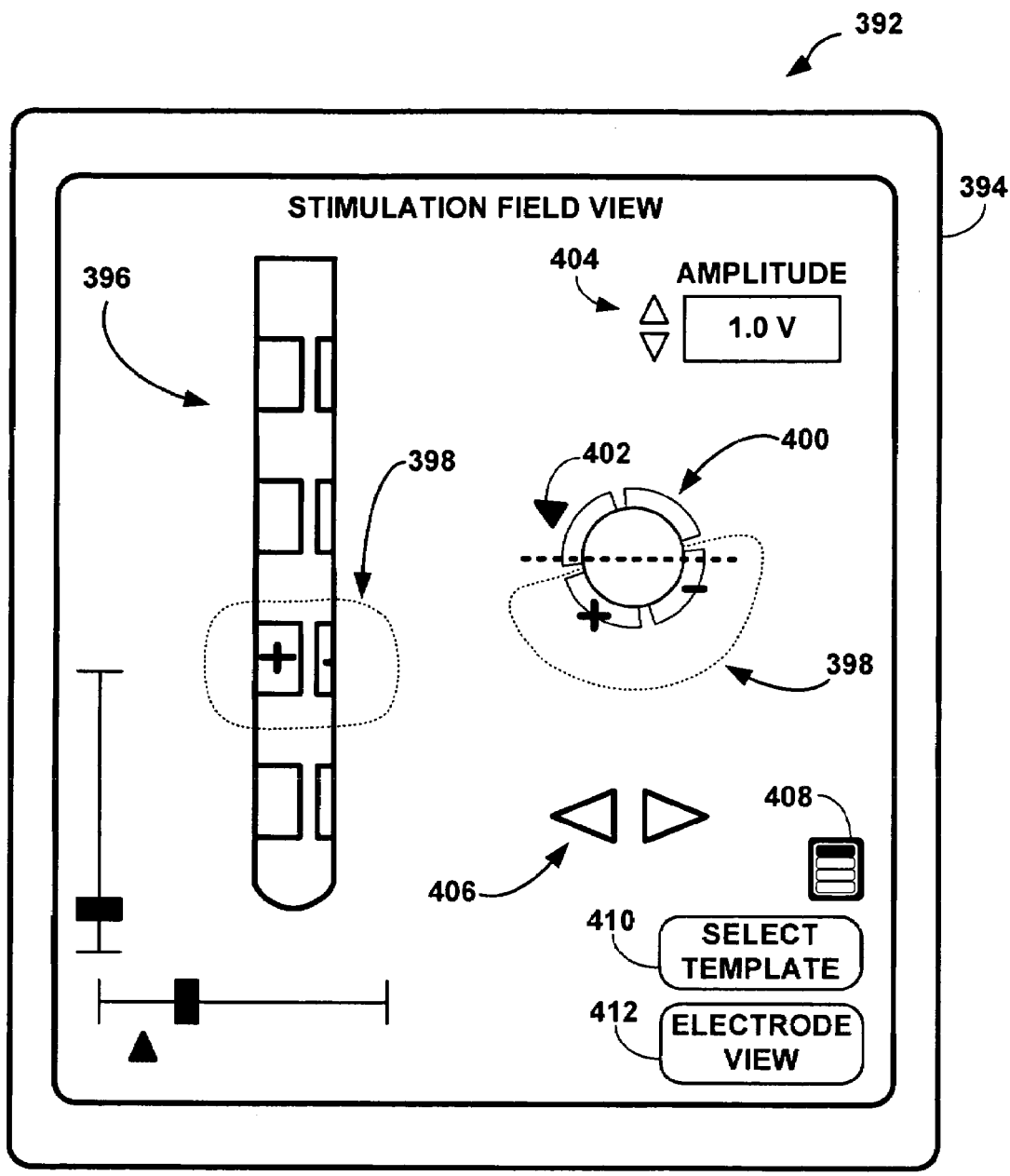
FIGS. 31-36 are schematic diagrams and a flow diagram illustrating example user interfaces that present stimulation templates to the user.
Figure 32:
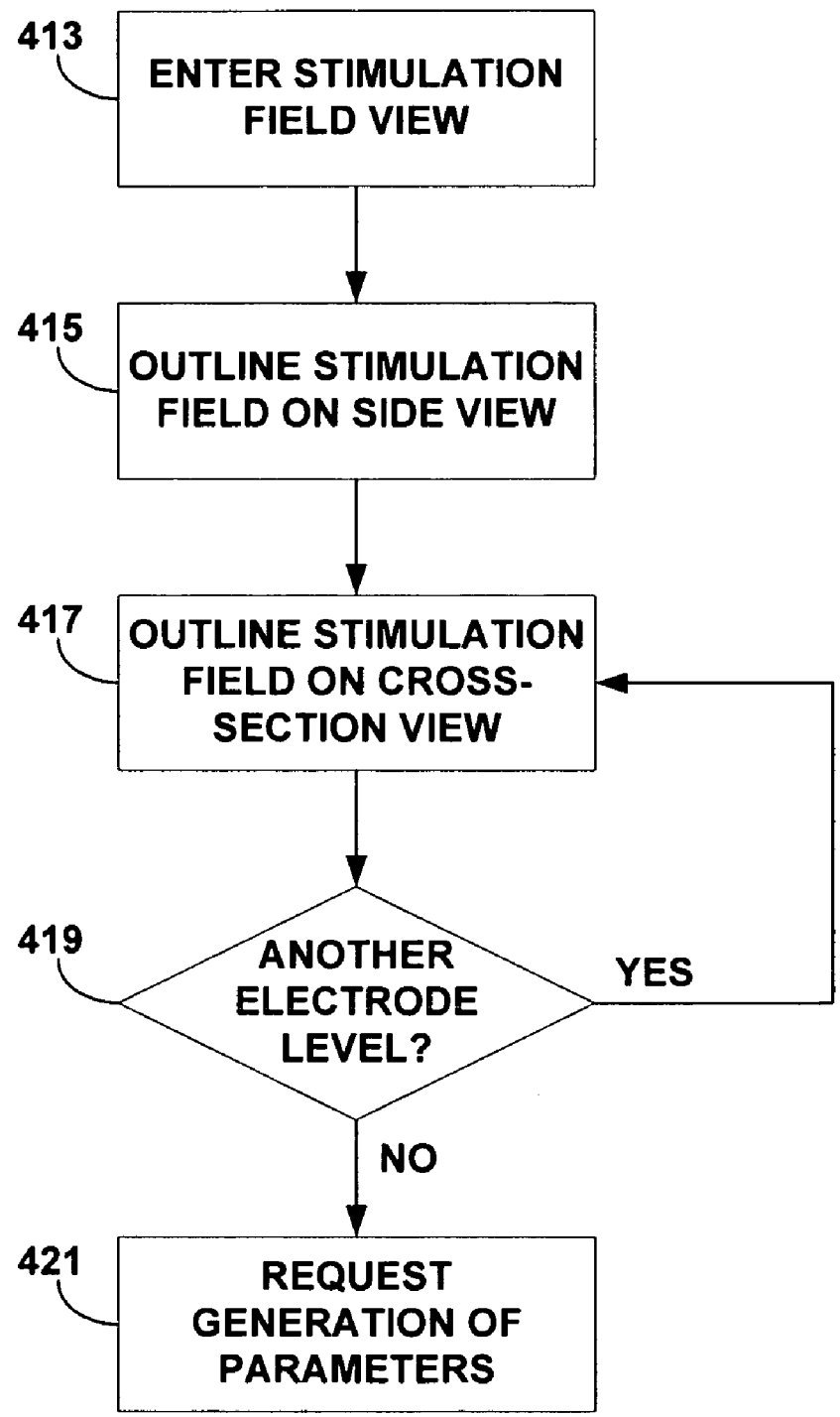

FIGS. 31-36 include schematic diagrams illustrating example user interfaces that present stimulation templates to the user. FIG. 32 illustrates example definition of a stimulation field. As shown in FIG. 31, user interface 392 presents a user defined stimulation field view the user via programmer 394. User interface 392 is an embodiment of user interface 98 and programmer 394 is an embodiment of programmer 19. User interface 392 allows the user to define stimulation field 398 by outlining the stimulation field on side view 396, cross-sectional view 400, or both. In addition to outlining stimulation field 398, the physician may drag any portion of the outline to change the shape or size of the field. Stimulation field 398 may represent the volume of patient 12 tissue around the implanted lead 14 to which the user desired to apply an electrical field from stimulator 20. In other embodiments, a stimulation field may be defined on any type of cross-sectional, concentric, or unwrapped view of lead 14.

As described above, the user may rotate side view 396 to view other electrodes of the lead or move stimulation field 398 with a slider or other input media. Amplitude adjustment mechanism 404 may be used to increase or decrease the size of stimulation field 398 by changing the amplitude of the stimulation therapy to be delivered to patient 12. The physician may also grab and drag stimulation field 398 to manipulate the size and shape of the field. In other embodiments, user interface 392 may present adjustment mechanisms for pulse width, pulse rate, or any other parameters. The user may use orientation marker 402 to identify where the lead position is with respect to known anatomical structures adjacent to the implanted lead 14. The user may use arrows 406 to change cross-sectional view 400 to another axial electrode level of the lead. When the physician is satisfied with stimulation field 398, the physician may select the select template button 410 to request that programmer 394 find the best stimulation template set and show the template set (described in FIGS. 33-35). In addition, the user may access other options provided by user interface 392 by selecting menu 408 or switch stimulation field view to the electrode view by selecting electrode view button 412.

FIG. 32 provides a flow diagram that illustrates an example method for defining a stimulation field as discussed above with respect to FIG. 31. In programmer 394, the physician may interact with user interface 392 to enter the stimulation field view (413). The physician then outlines stimulation field 398 on side view 396 with a stylus or other pointing device (415). Next, the physician outlines stimulation field 398 on cross-sectional view 400 to give the stimulation field another dimension that allows programmer 394 to generate the volumetric stimulation field 398 around the lead. If the physician desires to further define stimulation field 398 in other electrode levels (419), the physician selects a different cross-sectional view 400 and proceeds to define the field (417). Once the physician has completed defining stimulation field 398, the physician requests that programmer 394 generates stimulation parameters (421). As will be described below, the generation of parameters may include the selection of stimulation templates. However other equation sets, lookup tables, matrices, or other method may be employed for programmer 394 to select appropriate stimulation parameters from stimulation field 398.

In some embodiments, the physician may first define stimulation field 398 on cross-sectional view 400 prior to side view 398. However, both outlines are necessary for programmer 394 to generate the volumetric stimulation field. Stimulation field 398 is the desired area that the physician would like to stimulate with therapy. In other embodiments, the physician may be able to outline or otherwise define and manipulate the stimulation field in the field view 175 of FIG. 11 (or other similar embodiment). Therefore, a separate stimulation field view may not be required for a physician to request that the programmer automatically generate stimulation parameters from a defined stimulation field.

Figure 33:
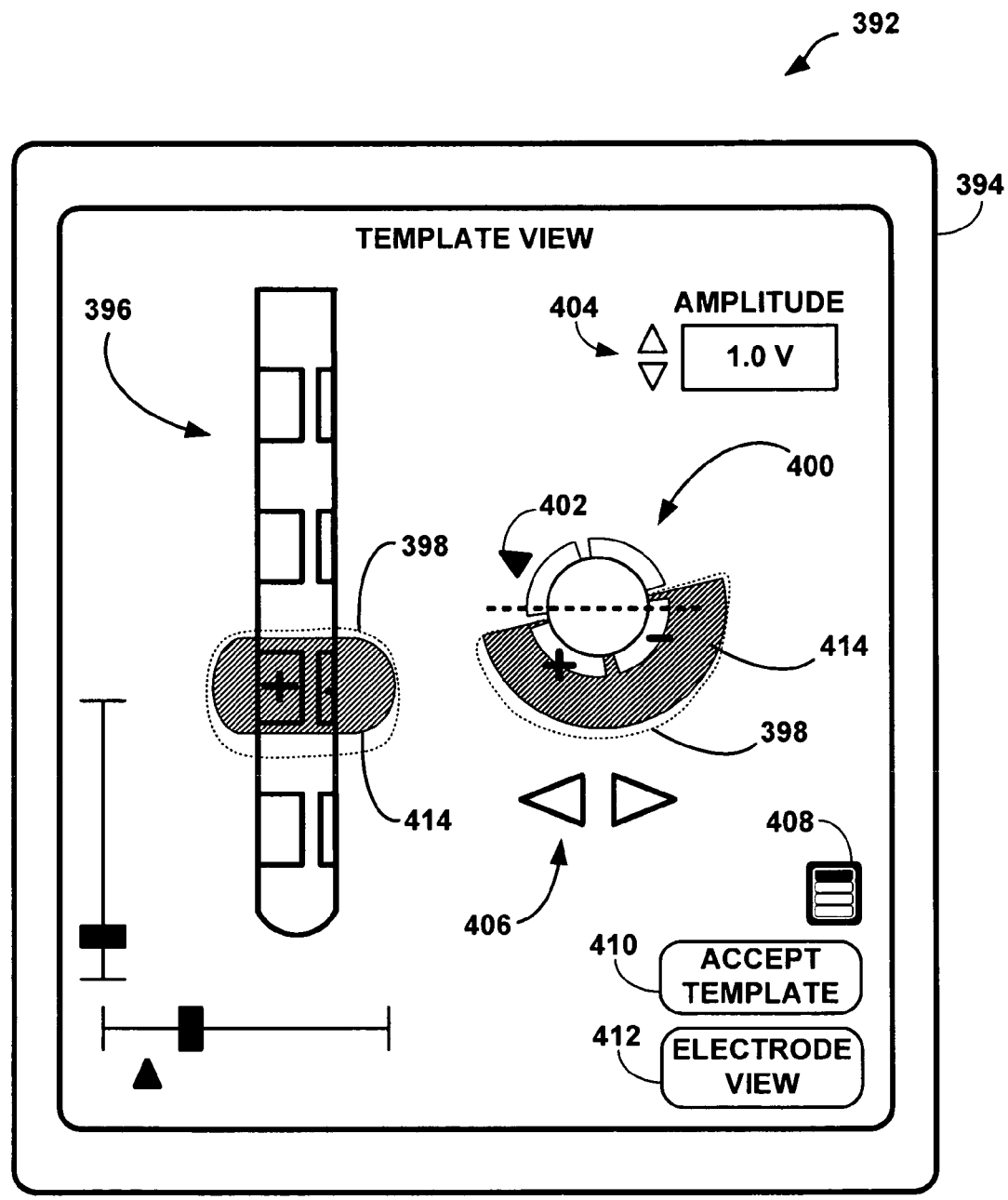

FIG. 33 illustrates user interface 392 that provides a template view to the user via programmer 394. Based upon stimulation field 398 that the user has defined in FIG. 32, programmer 394 creates a best fit stimulation template set 414 from volumetric stimulation templates stored in memory 90 of the programmer. Stimulation template set 414 is the best fit stimulation template set for stimulation field 398 because it covers the majority of the stimulation field without extending beyond the edge of the stimulation field. This preference may be beneficial because side effects may be much less desirable than completely eliminating the condition of patient 12. Alternatively, the best fit stimulation template set 414 may completely cover stimulation field 398 such that the entire desired volume of tissue is affected by the stimulation therapy.

The user may alter the size of stimulation template set 414 by dragging stimulation field 398 to a different shape, moving the stimulation field to a different location on the lead, or changing the magnitude of amplitude 404. Programmer 394 may create a new stimulation template set after stimulation field 398 changes enough that a new stimulation template set provides a better fit. As described above, stimulation template set 414 is representative of a stimulation parameter set that stimulator 20 uses to deliver stimulation therapy to patient 12. If the user is satisfied with stimulation template set 414, the user may select accept template button 410 to save the stimulation template set and transmit the associated stimulation parameters to stimulator 20 for therapy.

Figure 34:
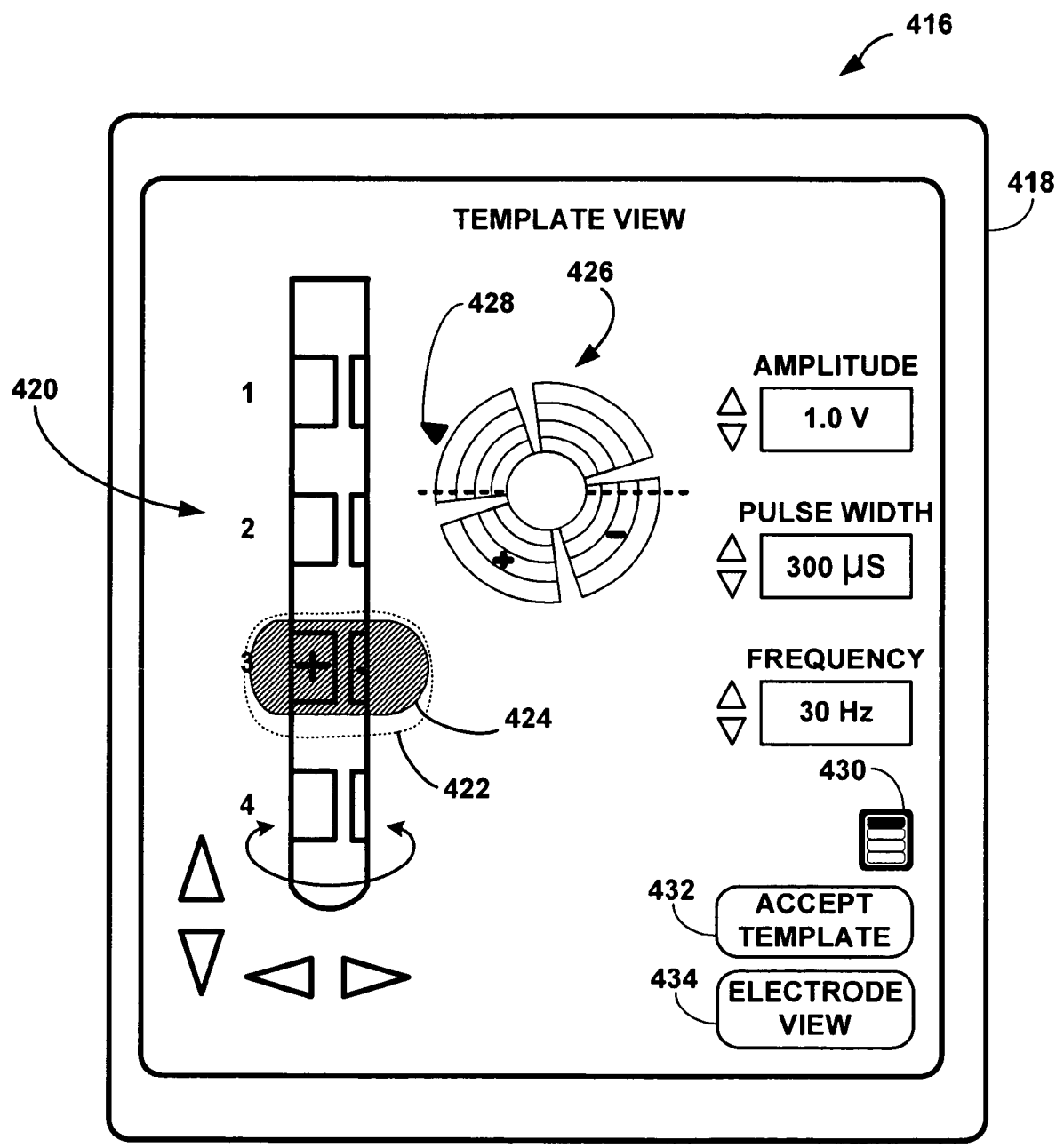

FIG. 34 illustrates user interface 416 which presents side view 420 and concentric axial view 426 to the user via programmer 418. User interface 416 is substantially similar to user interface 392, but user interface 416 provides concentric axial view 426 instead of cross-sectional view 400. The user has defined stimulation field 422 on side view 420 and programmer 418 has created stimulation template set 424 to fit the stimulation field. The user may alter stimulation field 422 or move the stimulation field, and in response programmer 418 may create a new stimulation template set. In some embodiments, programmer 418 presents plus and minus signs on the electrodes associated with stimulation template set 424. The physician may decide to change the polarity of one or more electrodes to modify the effective stimulation therapy to patient 12. In the change in polarity alters the shape or size of stimulation template set 424, programmer 418 may change the representation of the template set accordingly.

In some embodiments, the user may define stimulation field 422 on concentric axial view 426 in addition to side view 420. The stimulation field may be shown to cover each respective electrode of concentric axial view that would be used for therapy. In addition, stimulation template set 424 altered as the user determines that stimulation template set 424 is not sufficient to deliver efficient therapy to patient 12. When the user determines that stimulation template set 424 is ready to be used for stimulation therapy, the user may select accept template button 432 to transmit the stimulation parameters of the stimulation template to stimulator 20.

Figure 35:
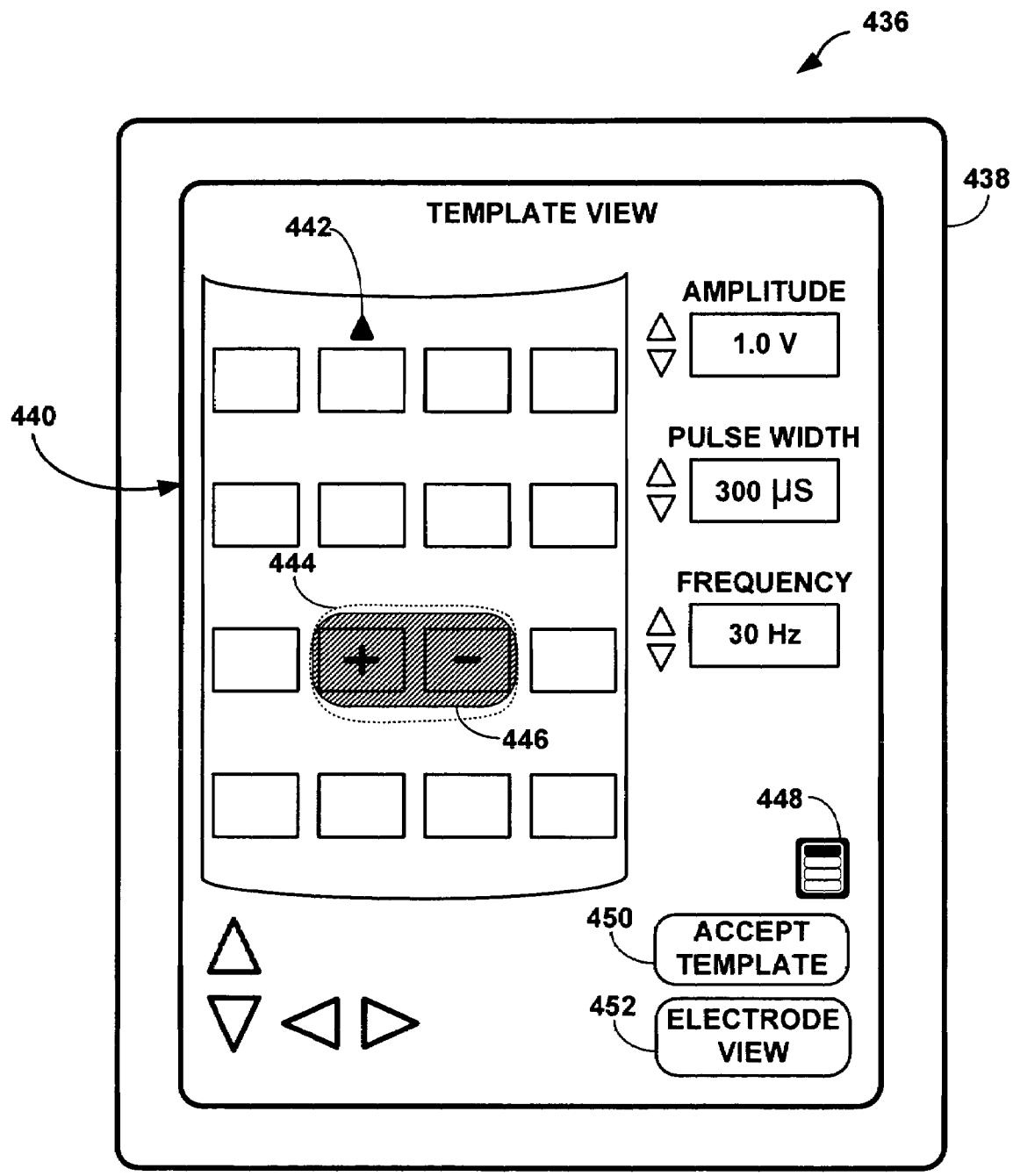

FIG. 35 illustrates user interface 436 which presents unwrapped 2D array view of the lead to the user via programmer 438. User interface 436 is substantially similar to user interface 392, but user interface displays the electrodes of the lead in a different manner. In the example of FIG. 35, the user has defined stimulation field 444 on unwrapped 2D array view 440 to fir the stimulation field. The user may alter stimulation field 444 or move the stimulation field such that programmer 438 will change stimulation template set 446 to match the new stimulation field. The user may also use orientation marker 442 to recognize the orientation of the lead to the anatomical structures of patient 12. When the user is satisfied with stimulation template set 446, the user may select accept template button 450 to accept the stimulation template set and transmit the corresponding stimulation parameters to stimulator 20 for therapy.

Figure 36:
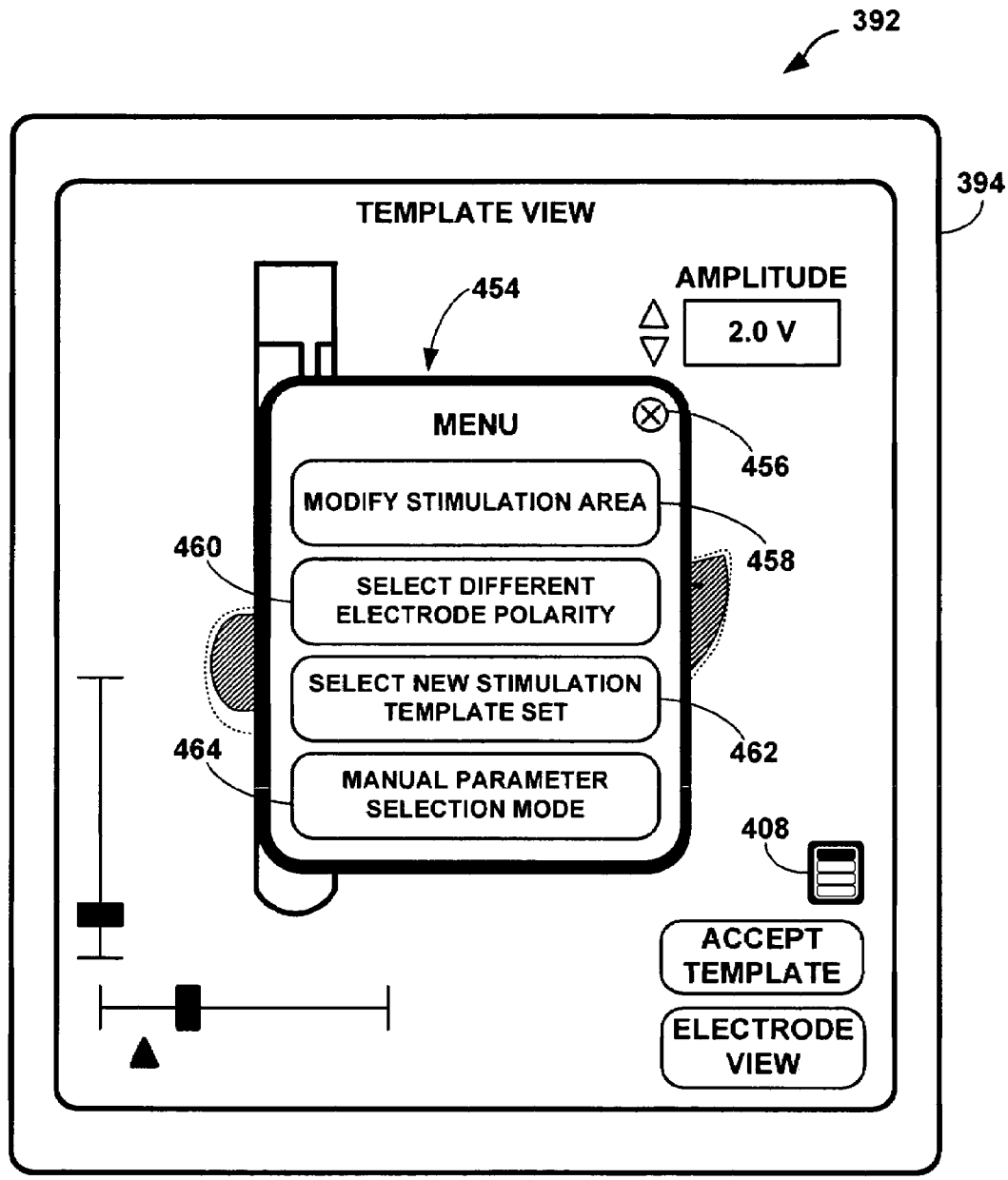

FIG. 36 illustrates an exemplary template menu of any user interfaces 392, 416, and 436. As shown in the example of FIG. 36, template menu 454 is presented to the user when the user presses menu 408. Template menu 454 includes modify stimulation field button 458 which allows the physician to modify stimulation field 398, select polarity button 460 to change the polarity of each electrode, new template set button 462 which forces programmer 394 to select a new stimulation template set, and manual selection button 464 which allow the user to return to the electrode view to manually select stimulation parameters in user interface 392. The user may close template menu 454 by selecting exit 456. In other embodiments, template menu 454 may provide different options to the user to enter any other mode offered by programmer 394.

Figure 37:
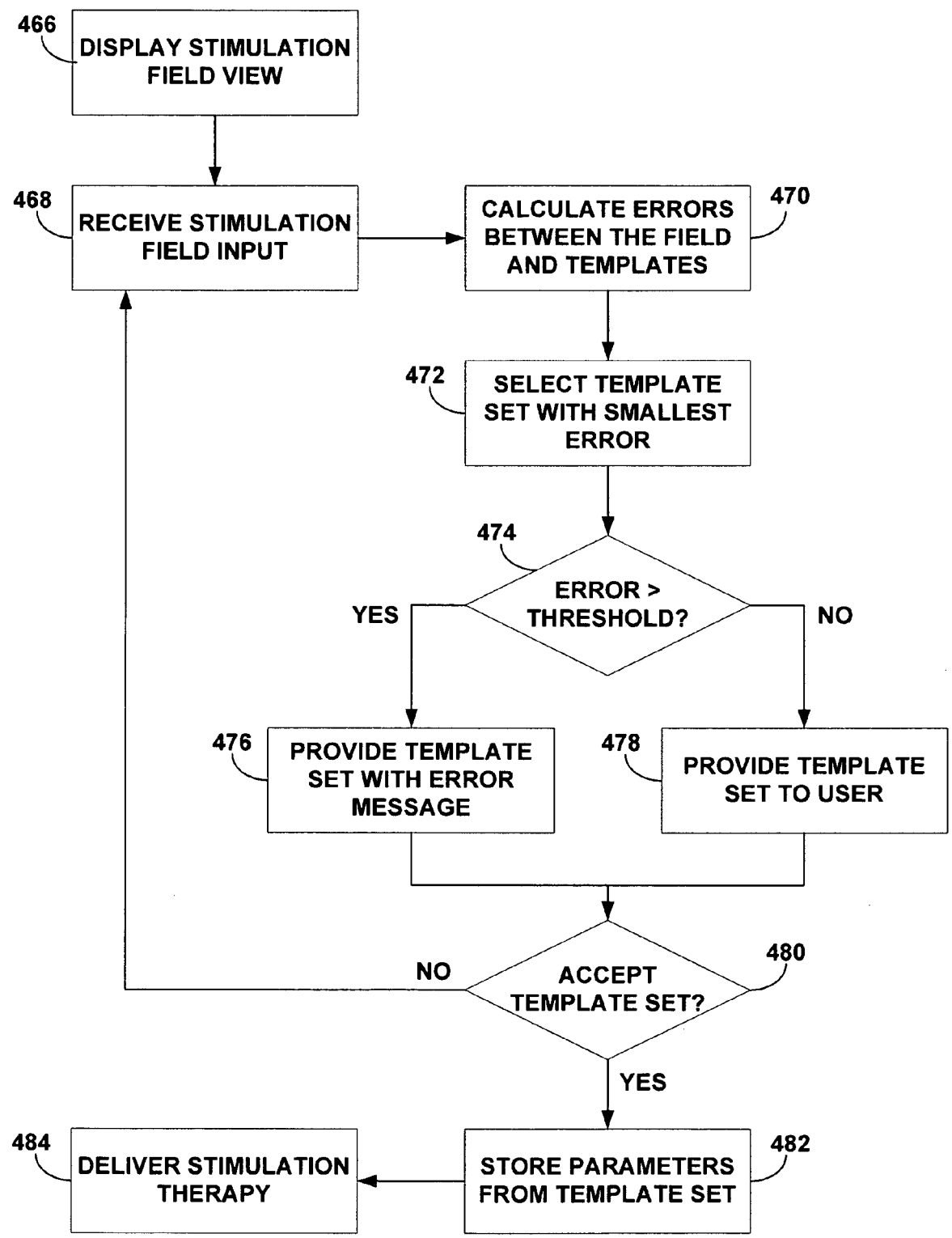
FIG. 37 is a flow diagram illustrating example operation of the programmer for selecting one or more stimulation templates.

FIG. 37 is a flow diagram illustrating example operation of the programmer for selecting a stimulation template set. User interface 392 and programmer 394 is used herein as an example, but any programmer may be used in the example of FIG. 37. As shown in FIG. 37, user interface 392 displays the stimulation field view to the user (466). User interface 468 next receives stimulation field input from the user (468). The stimulation field input may include outlining the stimulation field on one or more views of the lead or altering a stimulation field produced manually from an electrode view or automatically in the stimulation field view. Programmer 394 calculates the error between the stimulation field and the available stimulation templates (470). The error may be calculated as the difference in volume between the defined stimulation area and the volumetric stimulation template set, divided by the defined stimulation area. However, other methods of calculating the error may be used to identify the "fit" of the stimulation template set to the defined stimulation field. From the error calculations, programmer 394 selects the stimulation template set with the smallest error between the templates and the stimulation field (472). Typically, the template set must remain within the defined stimulation area to prevent stimulation of non-target tissue. However, some embodiments, may allow stimulation template sets that best fit the stimulation area even when a portion of the stimulation template set stimulates tissue outside of the stimulation field.

If the best fit stimulation template set error is greater than a predetermined threshold (474), user interface 392 will provide the stimulation template set to the physician with an error message indicating that the template set exceeds the error (476), and in some embodiments of user interface 392, programmer 394 may force the physician to modify the stimulation field. If the best fit stimulation template set error is less than the predetermined threshold (474), user interface 392 provides the stimulation template set to the physician (478). If the physician does not accept the created stimulation template set (480), user interface 392 will again receive stimulation field input (468). If the physician wants to accept the stimulation template set for therapy (480), programmer 394 stores the stimulation parameters from the stimulation template set (482). Programmer 394 then delivers the stimulation parameter sets to stimulator 20 which delivers the stimulation therapy to patient 12 (484).

Figure 38:
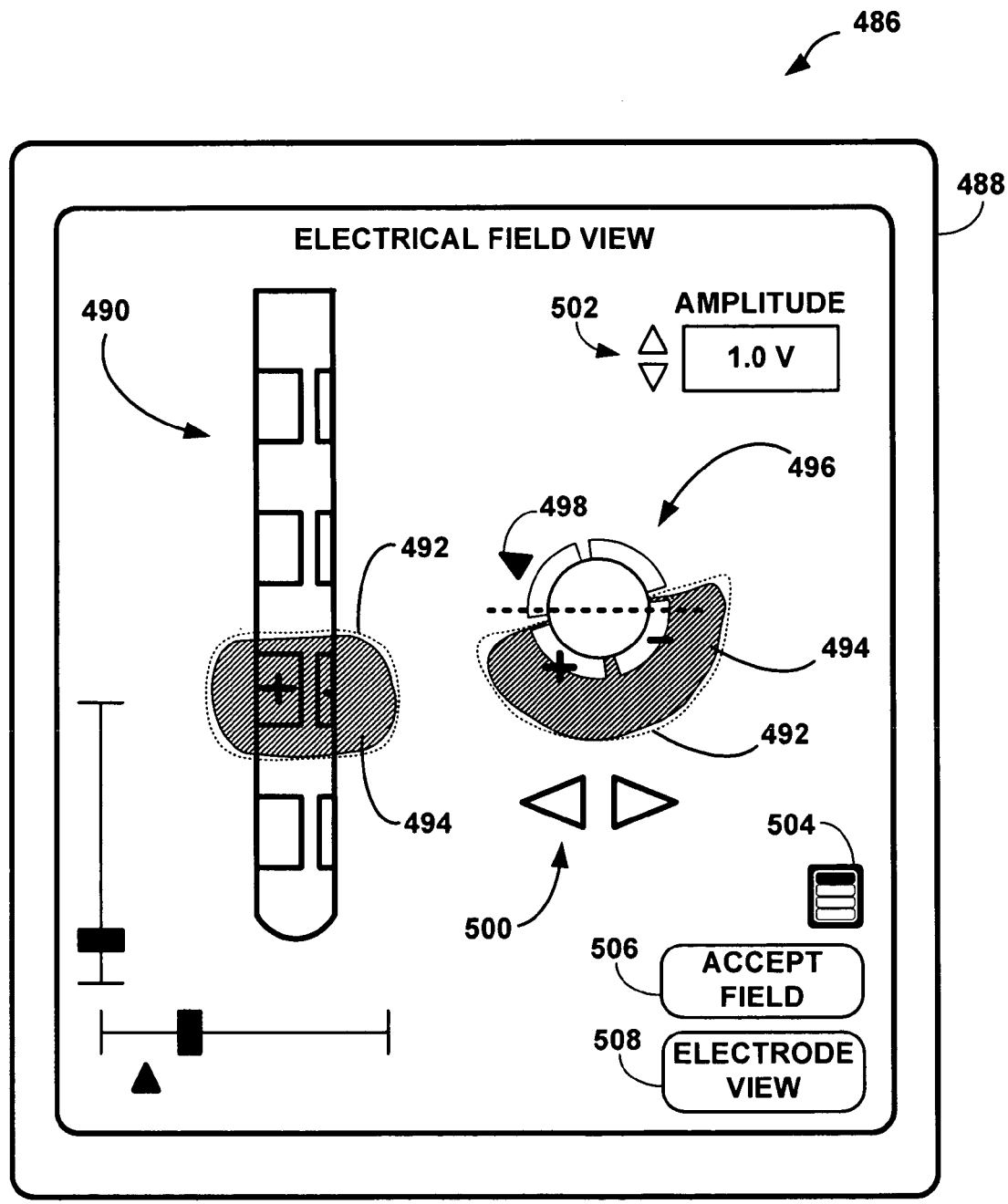
FIGS. 38-44 are schematic diagrams illustrating example user interfaces that present electrical field models and activation field models to the user.

FIGS. 38-44 are schematic diagrams illustrating example user interfaces that present electrical field models and activation field models to the user. FIG. 38 illustrates an example user interface 486 that displays a field view to the user via programmer 488. User interface 486 is an embodiment of user interface 98 and programmer 488 is an embodiment of programmer 19. User interface 486 displays side view 490 and cross-sectional view 496 of the implanted lead, and the user defines stimulation field 492 on the side and cross-sectional views. From stimulation field 494, programmer 488 generates stimulation parameters for therapy and generates an electrical field model that estimates the electrical field of the therapy. The electrical field model is displayed as electrical field 494, within stimulation field 492. In other embodiments electrical field 494 be a representation of another electrical stimulation related characteristic, e.g., current density, or voltage gradient. In addition, the clinician may be able to switch between any of these representations when desired.

Electrical field 494 represents where the electrical current will propagate from the implanted lead 14 within brain 18, as tissue variation within brain 18 may change the electrical current propagation from the lead in some directions. The variations in electrical field propagation may affect the ability of the therapy to actually treat a desired structure or cause a side-effect. The horizontal and axial views of electrical field 494 illustrated in FIG. 38 are 2D slices of the volumetric electrical field model created by programmer 488. Programmer 488 utilizes the patient anatomy data with electrical field model equations that define electrical current propagation. More specifically, programmer 488 may apply the electrical field model equations that define how the electrical field is propagated from an origin location away from the origin. The electrical field equations require the physical tissue characteristics of the tissue adjacent lead 14, which is included in the patient anatomy data set. From this information, programmer is able to generate the estimated electrical field 494 that will be produced in therapy. Electrical field 494 may differ from the field view in FIG. 11 because the field view only includes general tissue characteristics not specific from patient 12. In other embodiments, the electrical field equations may utilize matrices or other mathematical model of the electrical field. In this manner, electrical field 494 can be estimated and modeled for the physician. Accordingly, the physician may be able to increase or decrease the amplitude of the stimulation parameters with amplitude 502 to change the size and possibly shape of electrical field 494 or directly manipulate electrical field 494. If the user is satisfied with electrical field 494, the user may select accept field button 506 to transmit the stimulation parameters to stimulator 20 and bring therapy.

Figure 39:
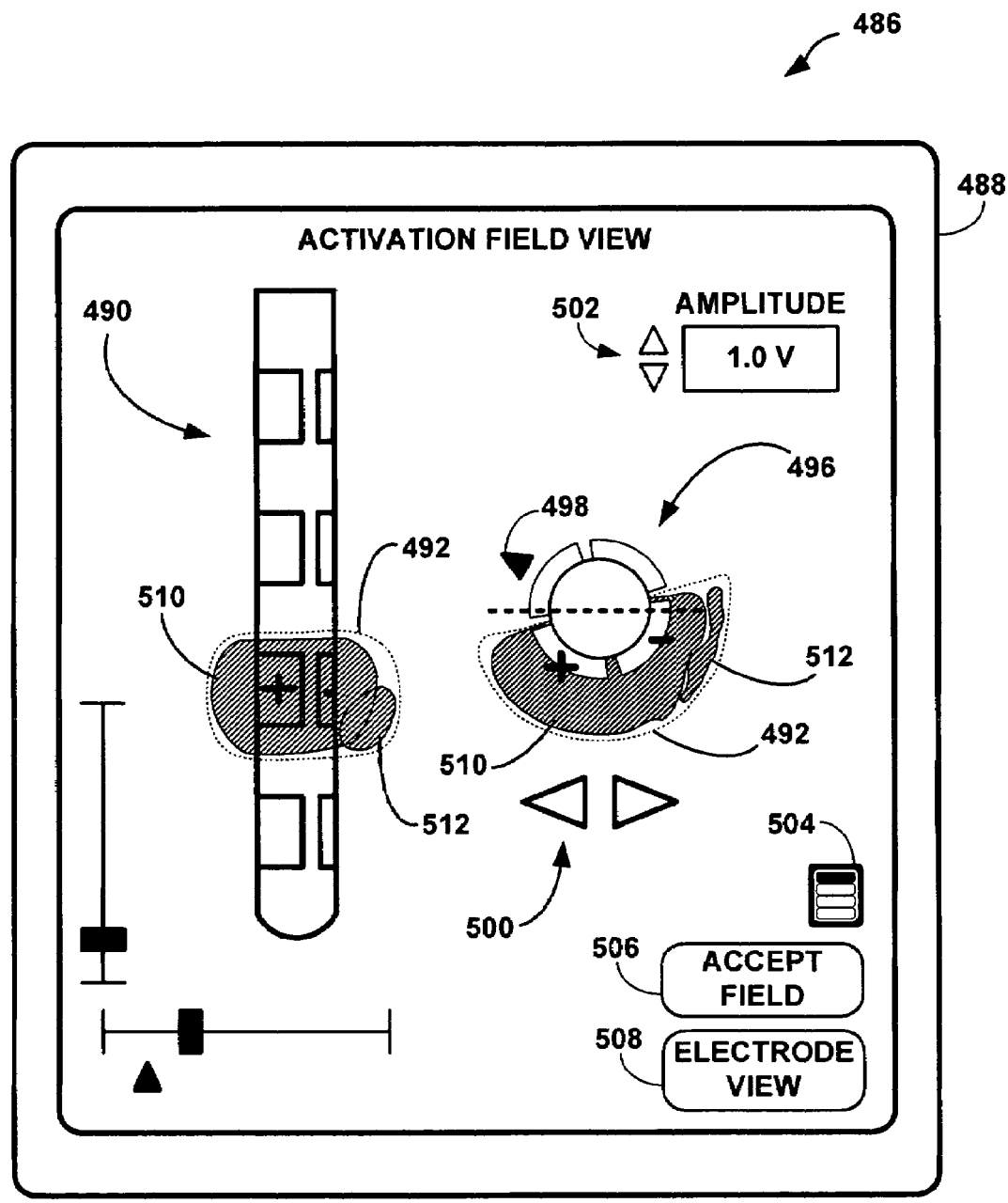

FIG. 39 is similar to FIG. 38 and illustrates an example user interface 486 that displays an activation field view to the user via programmer 488. From the defined stimulation field 492 on the side view 490 and cross-sectional view 492, programmer 488 generates stimulation parameters for therapy and generates an activation field model based upon the electrical field model of FIG. 38 and a neuron model that estimates which neurons within the electrical field model will be activated by the voltage of the electrical field during therapy. The neuron model may be a set of equations, a lookup table, or another type of model that defines threshold action potentials of particular neurons that make up the anatomical structure, as defined by the patient anatomy data, affected by the electrical field. If the voltage or current amplitude of the electrical field is above the threshold of any neuron within the electrical field, that neuron will be activated, e.g., cause a nerve impulse. The activation field model is displayed as activation fields 510 and 512, within stimulation field 492.

Activation fields 510 and 512 of the activation field model indicate to the user where neurons around the lead will be activated from the stimulation therapy. Due to changes in electrical current propagation and voltage thresholds to activate a neuron, the activation of neurons may vary with the location of tissue around the lead. Some neurons may activate further from the lead with smaller voltages while other neurons may only be activated close to the lead because of a high voltage threshold. These differences in neurons may account for separate activation fields 510 and 512 within a contiguous stimulation field 492. The user may view cross-sections at other electrode levels with arrows 500. In addition, the user may increase or decrease the size and/or shape of activation fields 510 and 512 by changing the amplitude with amplitude 502 or directly manipulate the activation fields to automatically modify the stimulation parameters. Once the user is satisfied with activation fields 510 and 512, the user may select accept field 506 to transmit the corresponding stimulation parameters to stimulator 20 for therapy.

Figure 40:
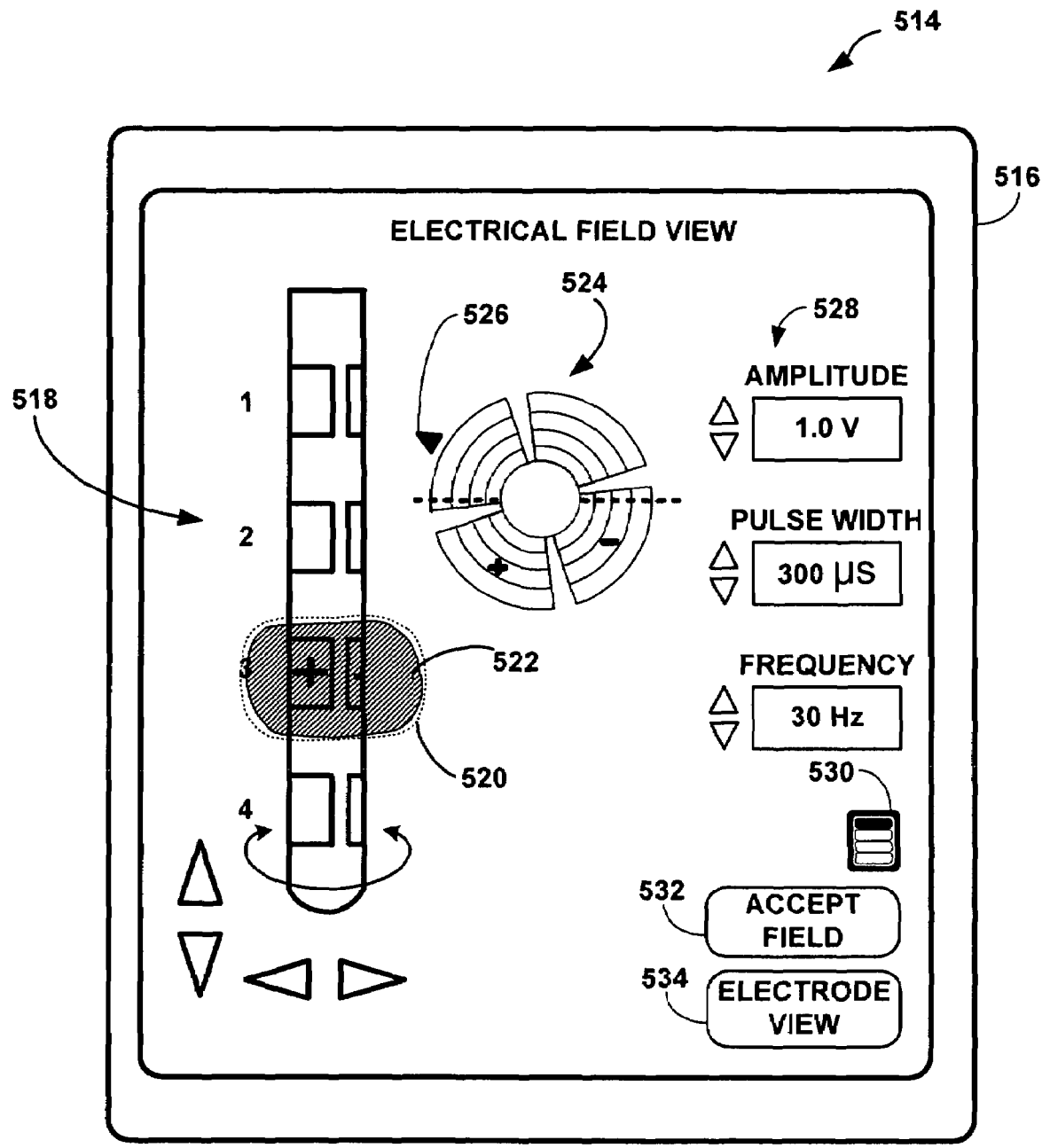

FIG. 40 illustrates an example user interface 514 that displays an electrical field view to the user via programmer 516. User interface 514 displays side view 518 and concentric axial view 524 of the implanted lead, and the user defines stimulation field 520 on the side view. From stimulation field 520, programmer 516 generates stimulation parameters for therapy and generates an electrical field model that estimates the electrical field of the therapy, similar to programmer 488 of FIG. 38. While electrical field 522 is not shown over concentric axial view 524, other embodiments may include the electrical field displayed over the appropriate electrodes of the concentric axial view. Once the user is satisfied with electrical field model, the user may select accept field button 532 to begin stimulation therapy. Stimulation field 520 is not shown in user interface 514 because the stimulation field may not accurately show the field to the physician. However, in some embodiments, stimulation field 520 may also be shown over concentric axial view 524 to approximate the field in the axial dimension.

Figure 41:
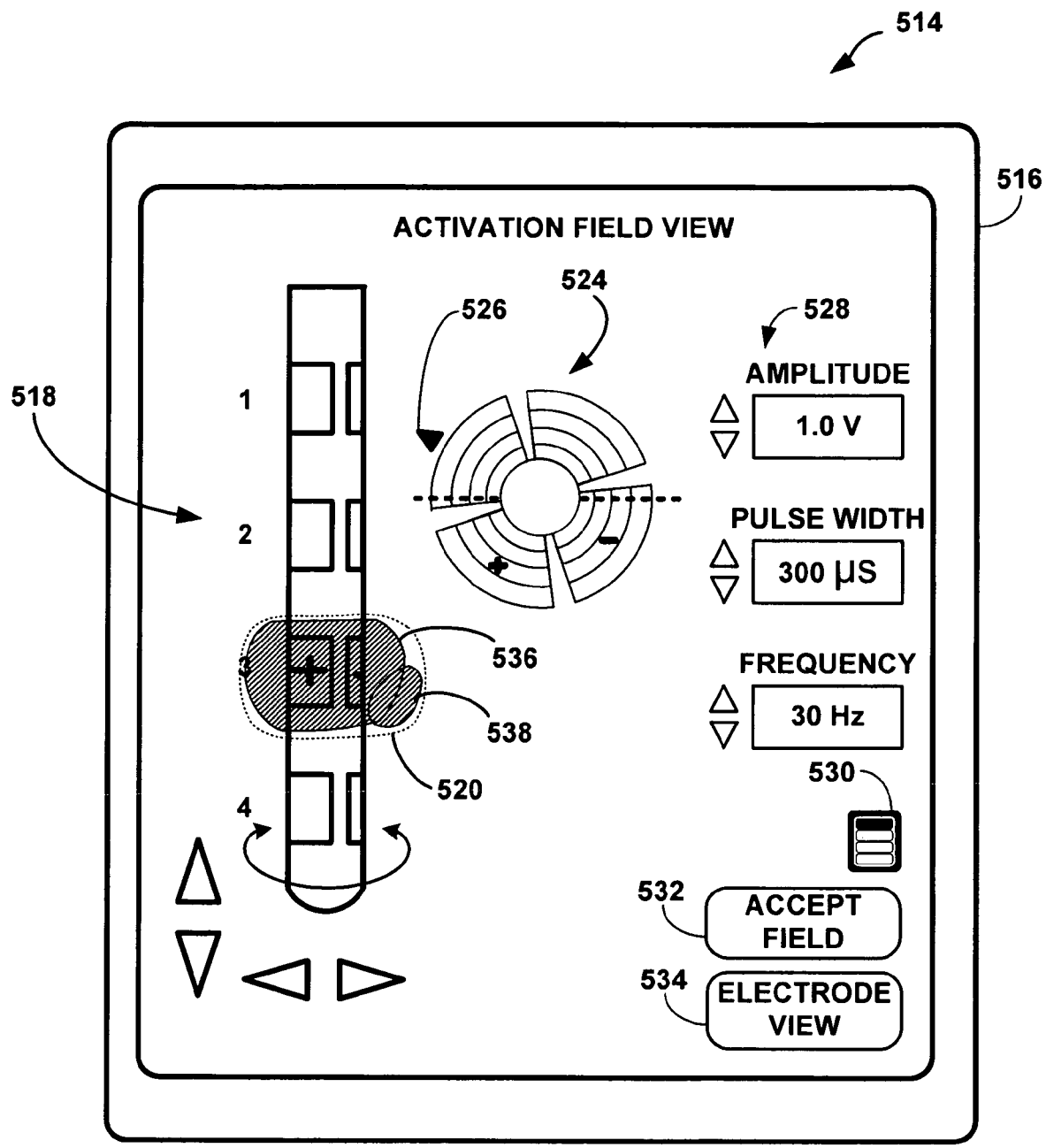

FIG. 41 is similar to FIG. 40 and illustrates an example user interface 514 that displays an activation field view to the user via programmer 516. Activation field view of FIG. 41 may be substantially similar to FIG. 39 with respect to generating and displaying the activation field model. From the defined stimulation field 520 on the side view 518, programmer 516 generates stimulation parameters for therapy and generates an activation field model based upon the electrical field model of FIG. 40 and a neuron model that estimates which neurons within the electrical field model will be activated by the voltage of the electrical field during therapy. The activation field model is displayed as activation fields 536 and 538, within stimulation field 520. While activation fields 536 and 538 are not shown over concentric axial view 524, other embodiments may include the activation fields displayed over the appropriate electrodes of the concentric axial view for a different perspective of the activation field model. Once the user is satisfied with activation fields 536 and 538, the user may select accept field 532 to transmit the corresponding stimulation parameters to stimulator 20 for therapy.

Figure 42:
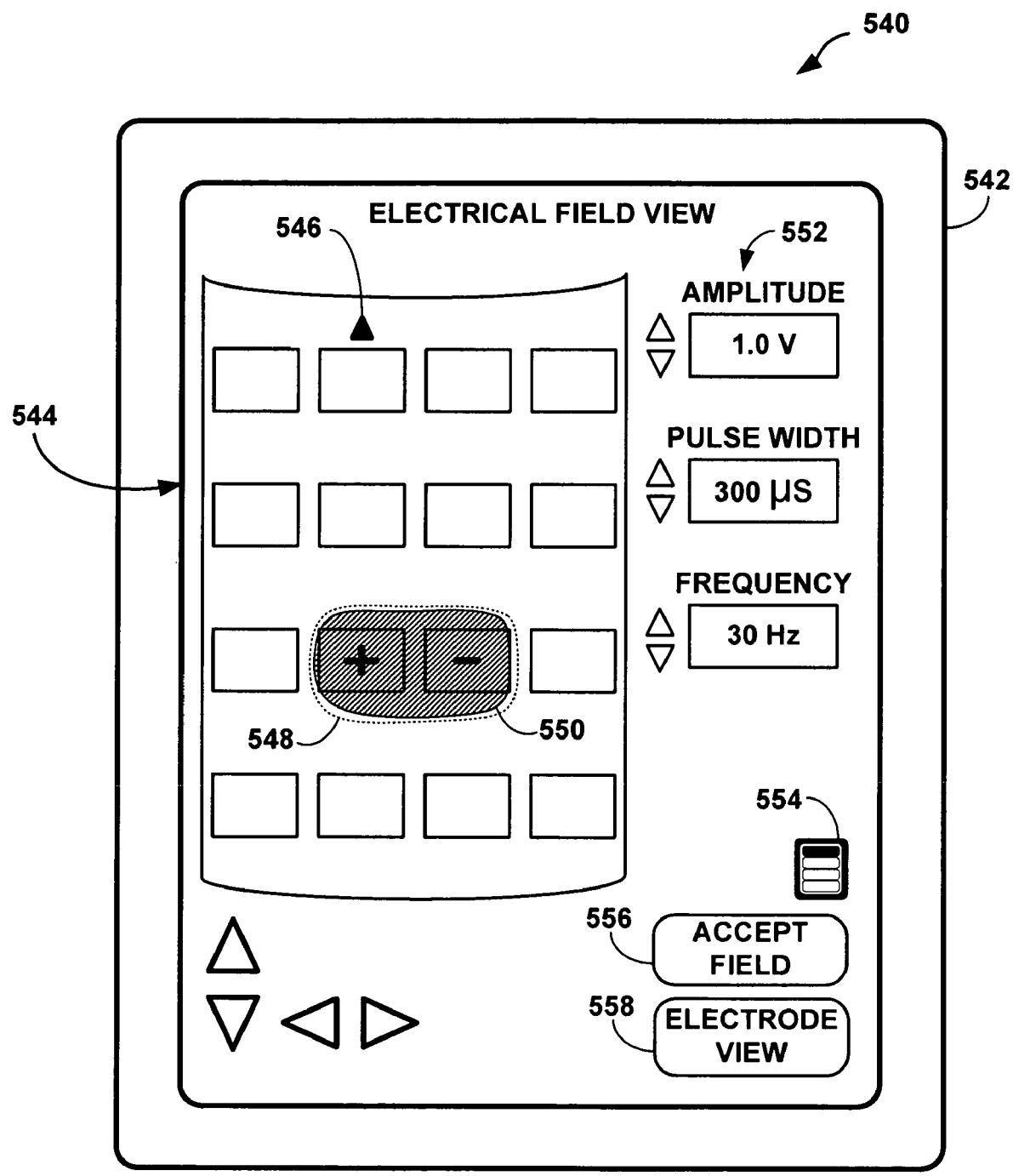

FIG. 42 illustrates an exemplary user interface 540 that displays an electrical field view to the user via programmer 542. User interface 542 is an embodiment of user interface 486 and programmer 542 is an embodiment of programmer 488. User interface 540 displays unwrapped 2D array view 544 and orientation arrow 546 of the implanted lead, and the user defines stimulation field 548 on the unwrapped 2D array view. From stimulation field 548, programmer 542 generates stimulation parameters for therapy and generates an electrical field model that estimates the electrical field of the therapy, similar to programmer 488 of FIG. 38. In some embodiments, user interface 540 may allow the user to rotate or flip unwrapped 2D array view to view the profile of electrical field 550 away from the electrodes of the lead. In other words, the physician may be able to view the distance away from the electrodes that the electrical field will propagate. Once the user is satisfied with electrical field model, the user may select accept field button 556 to begin stimulation therapy.

Figure 43:
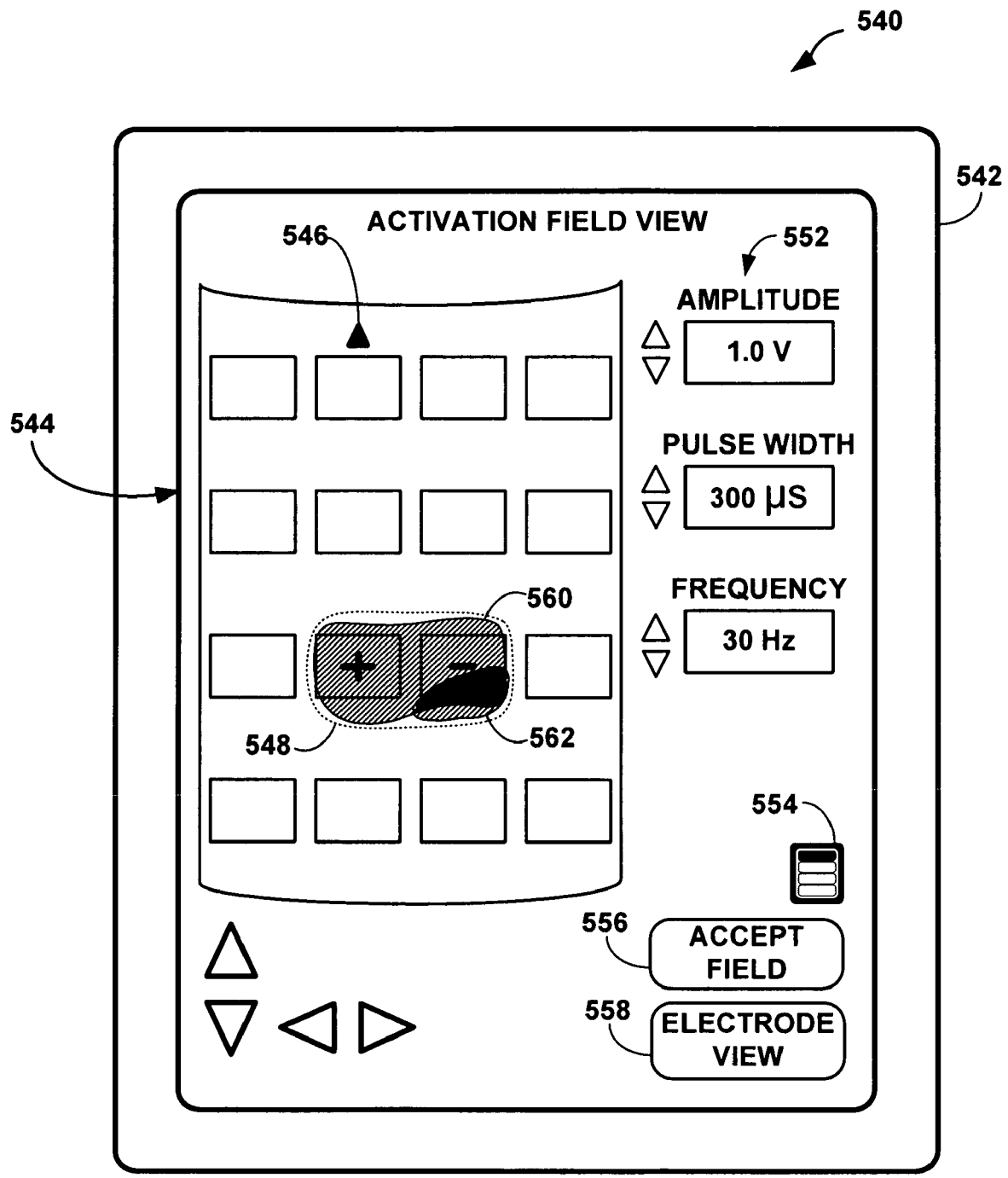

FIG. 43 is similar to FIG. 42 and illustrates an example user interface 540 that displays an activation field view to the user via programmer 542. The activation field view of FIG. 43 may be substantially similar to FIG. 39 with respect to generating and displaying the activation field model. From the defined stimulation field 548 on unwrapped 2D array view 544, programmer 542 generates stimulation parameters for therapy and generates an activation field model based upon the electrical field model of FIG. 42 and a neuron model that estimates which neurons within the electrical field model will be activated by the voltage of the electrical field during therapy. The activation field model is displayed as activation fields 560 and 562, within stimulation field 560. Similar to FIG. 42, some embodiments of user interface 540 may allow the user to rotate or flip unwrapped 2D array view 544 to view the profile of activation fields 560 and 562 away from the electrodes of the lead. Once the user is satisfied with activation fields 560 and 562, the user may select accept field 556 to transmit the corresponding stimulation parameters to stimulator 20 for therapy. While the activation field model has been shown to include two separate activation fields, any number of activation fields may be produced from the electrical field model and the neuron model. For example, one contiguous activation field may be produced by the programmer or several smaller activation fields may be produced. The examples of FIGS. 38, 40 and 42 are merely examples of potential activation fields.

Figure 44:
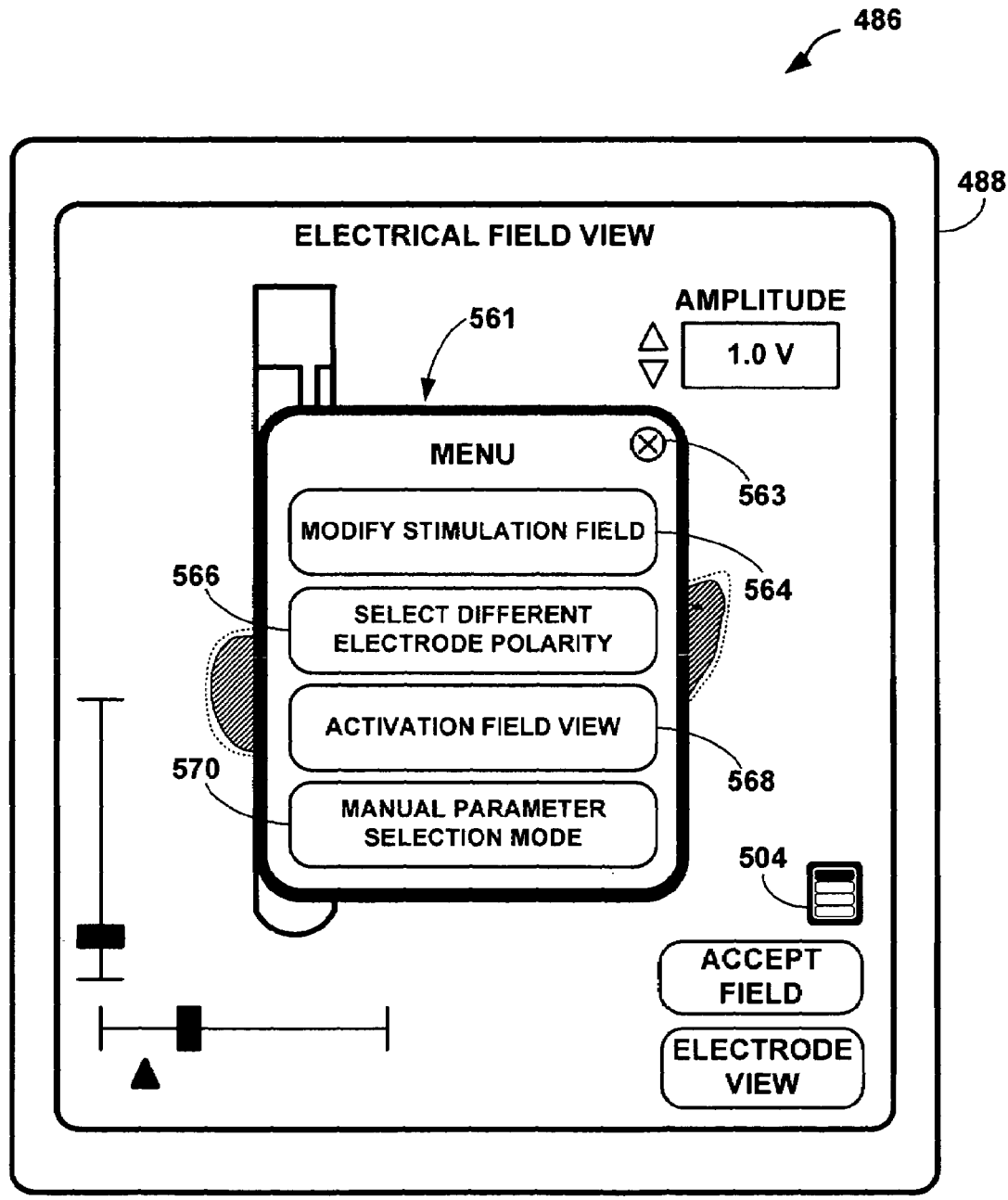

FIG. 44 illustrates an example field menu of any user interfaces 486, 514, and 540. As shown in the example of FIG. 44, user interface 486 presents field menu 561 to the user when the user presses menu 504. Field menu 561 includes modify stimulation field button 564 to redefine the stimulation field, select polarity button 566 to alter the polarity of any electrodes, change field view button 568 to modulate between electrical or activation field views, and manual mode button 570 which allows the user to manually select the stimulation parameters in the electrode view, e.g., FIG. 11. The user may close field menu 560 by selecting exit 563. In other embodiments, template menu 560 may provide different options to the user to enter any other mode offered by programmer 488.

In alternative embodiments, the electrical field model or activation field model may be used in place of the generic field view 175 of FIG. 11. For example, upon selection of electrodes in the electrode view, the programmer may generate the corresponding electrical field model or activation field model and present one of these customized fields of patient 12 to the physician in place of the generic field view described in FIG. 11. In addition, an electrical field view or activation field view may be applied to any side, cross-sectional, concentric axial, or unwrapped lead views described herein.

Figure 45:
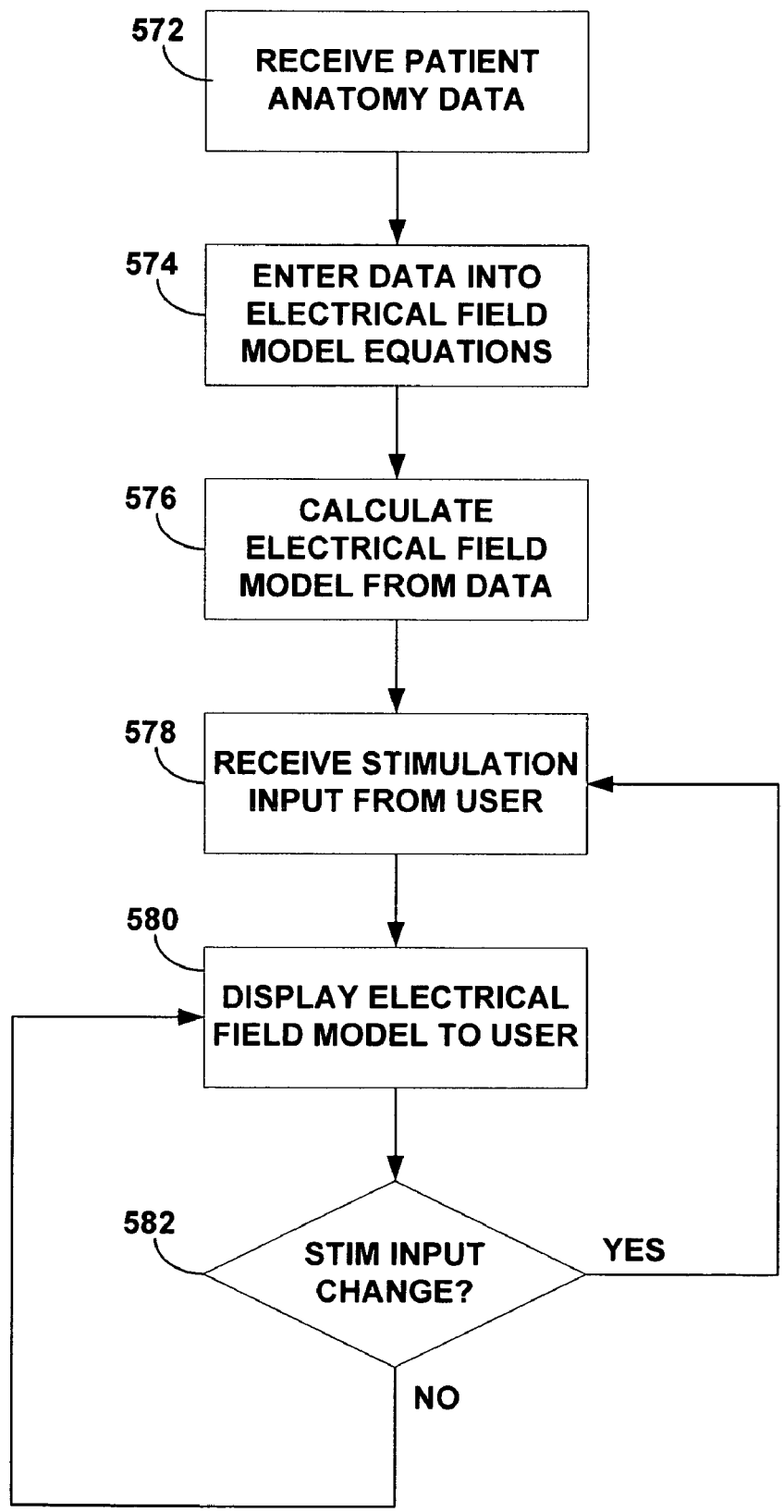
FIG. 45 is a flow diagram illustrating example operation of the programmer for generating and presenting an electrical field model.

FIG. 45 is a flow diagram illustrating an example technique for calculating and displaying the electrical field model of defined stimulation according to FIGS. 37, 39 and 41. As shown in FIG. 45, user interface 486 receives patient anatomy data necessary for creating an electrical field (572), as described in FIG. 38. Programmer 488 enters the patient anatomy data in stored electrical field model equations or equation sets to satisfy anatomical variable (574). Programmer 488 next calculates the electrical field model from the data and equations (576). Once user interface 486 receives stimulation input from the physician defining the stimulation field (578), the electrical field may be displayed to the physician via the user interface (580). If the physician desires to change the stimulation input (582), user interface 486 receives a change in the stimulation input (578). If the physician does not request a stimulation input change (582), user interface continues to display the electrical field to the physician (580).

Figure 46:
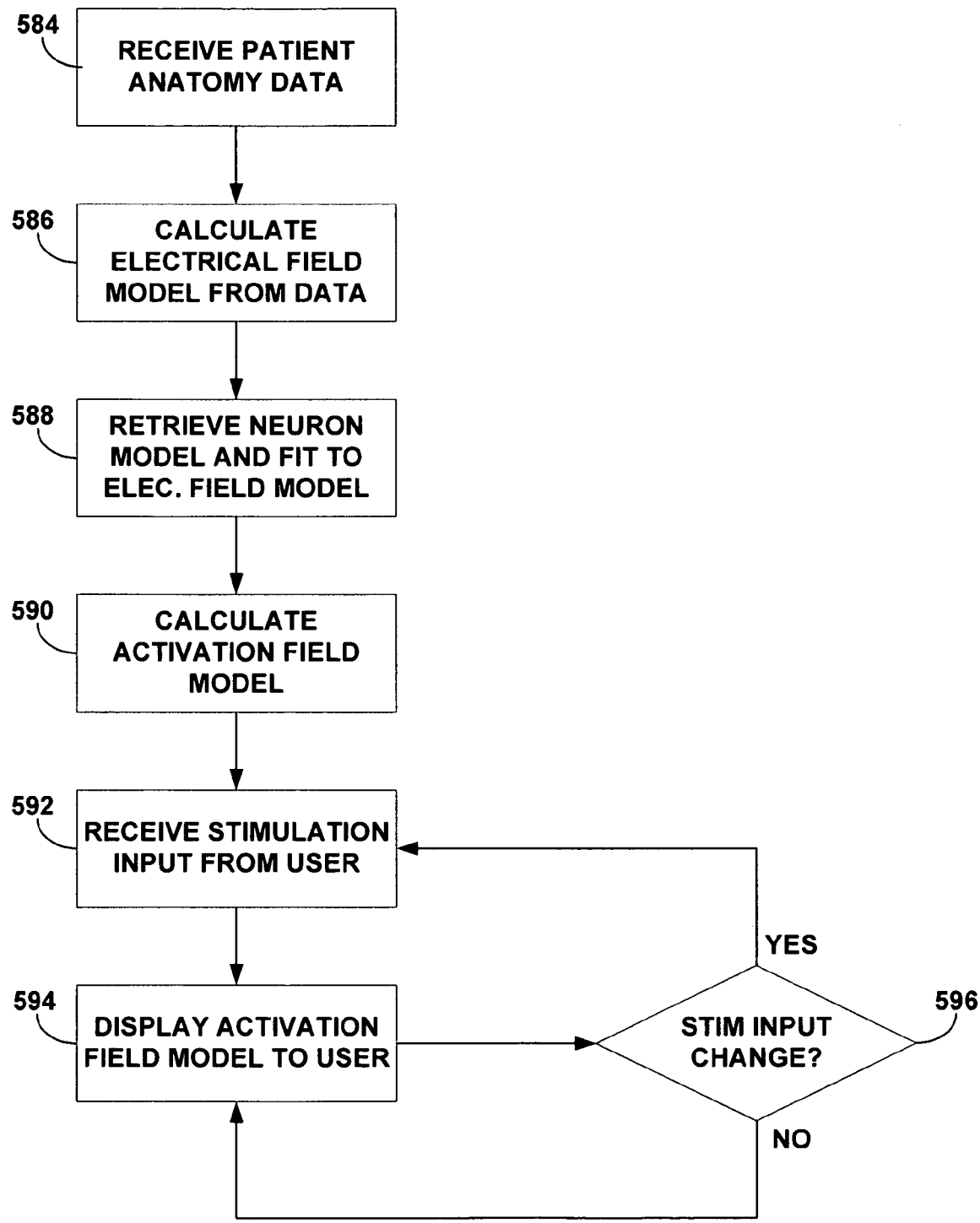
FIG. 46 is a flow diagram illustrating example operation of the programmer for generating and presenting an activation field model.

FIG. 46 is a flow diagram illustrating an example technique for calculating and displaying the activation field model of defined stimulation according to any of FIG. 38, 40 or 42. As shown in FIG. 46, user interface 486 receives patient anatomy data indicative of the anatomy of patient 12 (584) and programmer 488 calculates the electrical field model from the patient anatomy data (586). Programmer 488 then retrieves the neuron model and fits the neuron model to the electrical field (588). Programmer 488 then calculates the activation field model based upon the electrical field model and neuron model (590). User interface 486 then is able to receive stimulation input from the physician defining the stimulation field (592). The resulting activation field model is displayed by user interface 486 (594). If the physician desires to change the stimulation input (596), user interface 486 receives stimulation input from the physician modifying the previous stimulation input (592). If the stimulation input does not need to be changed (596), the activation field model continues to be displayed by user interface 486 (594).

Figure 47:
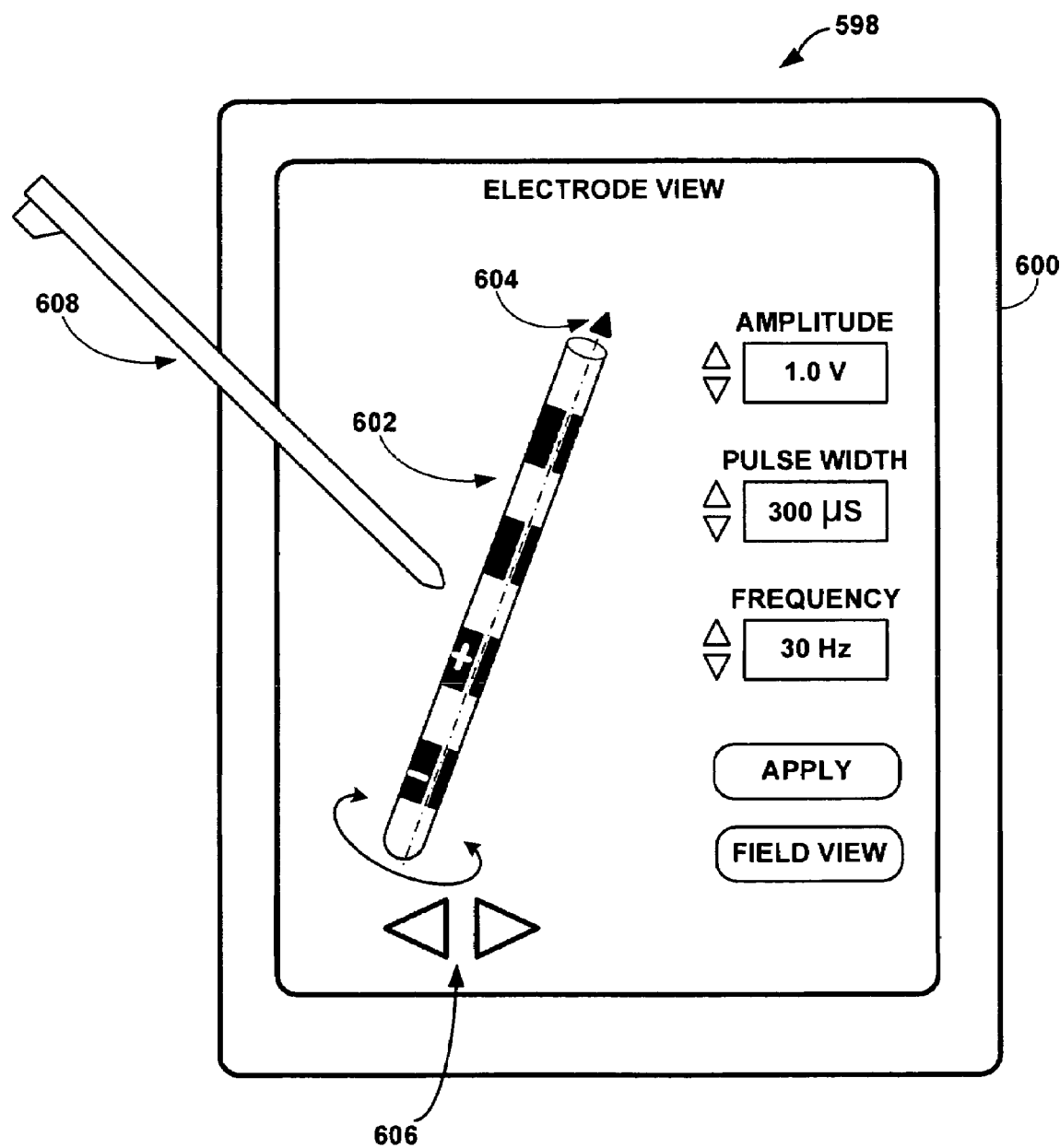
FIG. 47 is a diagram illustrating a user interface presenting a three-dimensional electrode view of a lead having a complex electrode array geometry.

FIG. 47 is a diagram illustrating a user interface 598 presenting three-dimensional view of a lead having a complex electrode array geometry. Although other embodiments emphasize presentation of two or more two-dimensional views of a lead with a complex electrode array geometry, a three-dimensional representation also may be useful. User interface 598 is an embodiment of user interface 98 and programmer 600 is an embodiment of programmer 19. In the example of FIG. 30, user interface 598 of programmer 600 presents an isometric view 602 of the lead to present a virtual three-dimensional view of the lead. Arrows 606 or other input media may be provided to permit the user to rotate the three-dimensional representation of the lead. In particular, user interface 598 may rotate the lead about its longitudinal axis to show electrodes on different sides of the lead. As in other embodiments, a user may select electrodes, e.g., with a stylus 608, and specify parameter values in an electrode view.

Figure 48:
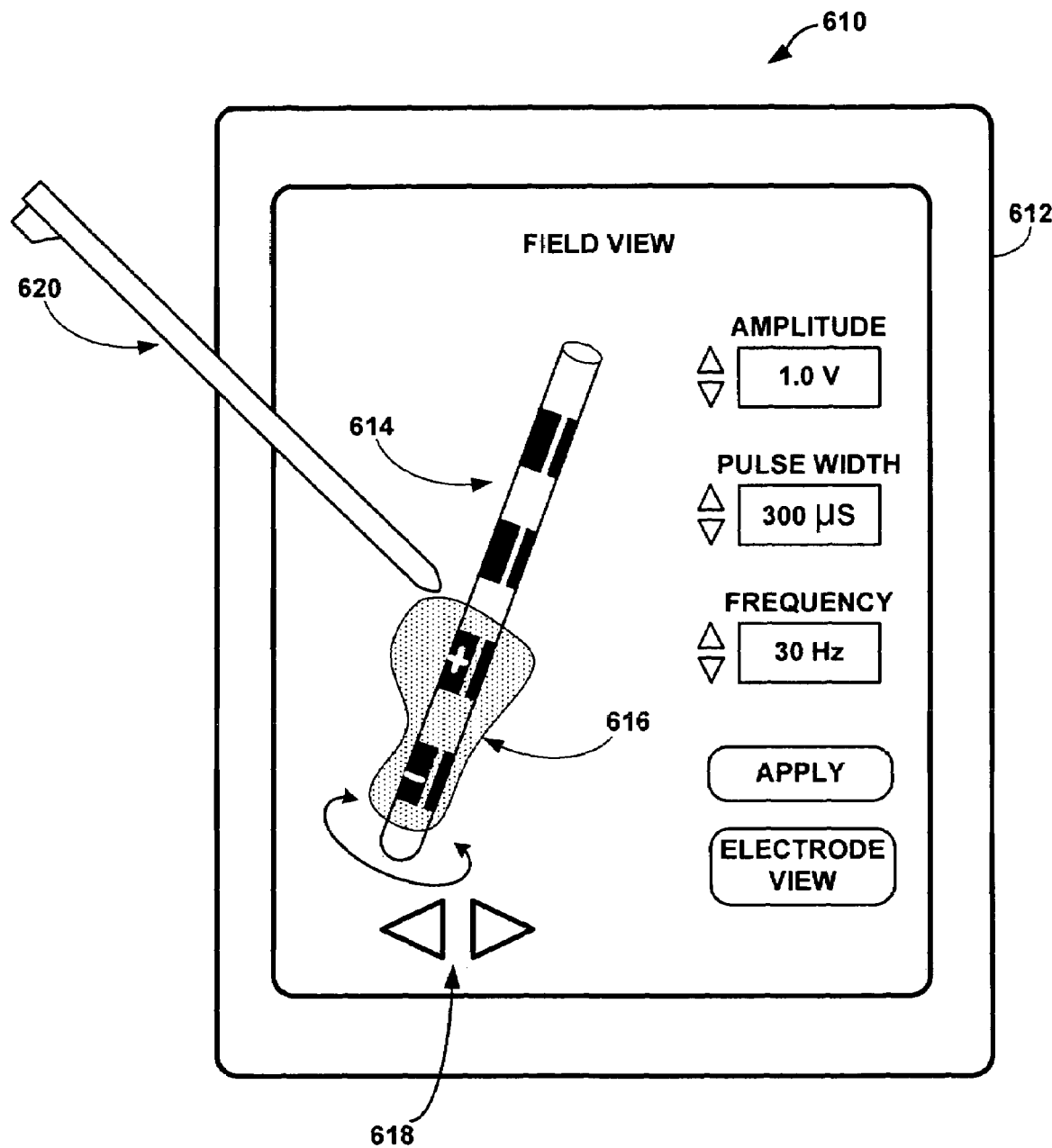
FIG. 48 is a diagram illustrating a user interface presenting a three-dimensional field view of a lead having a complex electrode array geometry.

Also, the user may select a three-dimensional field view, as shown in FIG. 48. User interface 610 is an embodiment of user interface 98 and similar to user interface 598. Programmer 612 is an embodiment of programmer 19 and similar to programmer 600. In the field view, user interface 610 may allow the field to be manipulated by the user in terms of size, shape, location, or the like, as previously discussed. Programmer 612 responds by selecting electrode combinations, polarities and parameter values sufficient to approximate stimulation field 616 manipulated by the user. In the three-dimensional electrode view of FIG. 47 and the field view of FIG. 48, the three-dimensional representation may be displayed alone or in combination with other views, such as two-dimensional views, e.g., a side view a cross-sectional view, a concentric axial view, or an unwrapped 2D array view. Many other combinations of three-dimensional and two-dimensional views are conceivable, as well as other three-dimensional views in addition to the illustrated isometric view. Also, orientation markers 604 also may be provided as shown in FIG. 46 to show the orientation of the electrodes of the lead relative to an anatomical structure.

Although this disclosure has referred to neurostimulation applications generally, and DBS and SCS applications more particularly, such applications have been described for purposes of illustration and should not be considered limiting of the invention as broadly embodied and described herein. The invention may be more generally applicable to electrical stimulation of tissue, such as nerve tissue or muscle tissue, and may be applicable to a variety of therapy applications including spinal cord stimulation, pelvic floor stimulation, deep brain stimulation, cortical surface stimulation, neuronal ganglion stimulation, gastric stimulation, peripheral nerve stimulation, or subcutaneous stimulation. Such therapy applications may be targeted to a variety of disorders such as chronic pain, peripheral vascular disease, angina, headache, tremor, Parkinson's disease, epilepsy, urinary or fecal incontinence, sexual dysfunction, obesity, or gastroparesis. Also, the invention is not necessarily limited to use with completely implanted neurostimulators, and may also be applicable to external stimulators coupled to implanted leads via a percutaneous port.

In addition, although electrode array geometries having four or eight axial electrode levels and four angular electrode positions have been described, the disclosure may be applicable to a wide variety of electrode array geometries including virtually any number of axial and angular electrode positions. Again, a complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead. Another example of a simple electrode array geometry is a planar array of electrodes on a paddle lead.

An example of a complex electrode array geometry, in accordance with this disclosure, is an array of electrodes positioned at different axial positions along the length of a lead, as well as at different angular positions about the circumference of the lead. In some embodiments, the electrodes in the complex array geometry may appear similar to non-contiguous, arc-like segments of a conventional ring electrode. A lead with a complex electrode array geometry may include multiple rings of electrode segments. Each axially positioned ring is disposed at a different axial position. Each electrode segment within a given ring is disposed at a different angular position. The lead may be cylindrical or have a circular cross-section of varying diameter. Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section. Also, electrodes positioned at particular axial or angular positions need not be aligned with other electrodes. Rather, in some embodiments, electrodes may be arranged in a staggered or checkerboard-like pattern.

Further, although a single lead may be useful in various stimulation applications, multiple leads may be useful in other applications such as bi-lateral DBS, SCS, or multi-site stimulation for gastric, pelvic or peripheral nerve stimulation. Accordingly, electrode combinations may be formed between electrodes carried by a single lead, electrode combinations formed between electrodes carried by one lead of a pair of leads, or electrode combinations formed between electrodes on different leads, as well as electrodes carried by a stimulator housing, e.g., in a so-called active can configuration.

The techniques described herein may be applied to a programming interface or control interface associated with a physician programmer, a patient programmer, or both. Hence, a physician may use a physician programmer in clinic to program and evaluate different electrode combinations and stimulation parameter values. A patient may use a patient programmer during daily use to adjust parameter values, select different electrode combinations, subject to keepout zones and ranges specified by the physicians. The physician programmer or patient programmer may be a small, portable, handheld device, similar to a personal digital assistant (PDA). Alternatively, in the case of a physician programmer, the programmer may be implemented in a general purpose desktop or laptop computer, computer workstation, or dedicated desktop programming unit.

In addition, the programming functionality described in this disclosure may be used to program an implantable stimulator coupled to one or more implantable leads or an external stimulator coupled to one more percutaneous leads. For example, the invention may be used for trial stimulation or chronic stimulation. In addition, the guided evaluation techniques provided by programmer 19 may be used in the physician programmer or in the patient programmer. In the case of a patient programmer, guided evaluation may automatically select electrode combinations and stimulation parameters for evaluation by the patient over a period of time, or present such combinations and parameters to the patient for proposed evaluation.

The patient may enter efficacy feedback into the patient programmer to indicate the perceived efficacy of each electrode combination and set of parameter values. The feedback may be recorded as efficacy information in the programmer for later retrieval by the physician to identify programs that are most effective for the patient. In addition, the feedback information may be used to rate different programs and present the ratings for selection of programs by the patient.

In some cases, the patient programmer may guide the patient through different electrode combinations by forcing the patient to evaluate new or unevaluated programs over a period of time. For example, once evaluated, a program (including electrode combination and parameter values) may be hidden from view or locked out so that the patient cannot reevaluate the same program. This encourages the patient to continue trying new stimulation options.

The physician programmer, patient programmer or both may include the ability to present both an electrode view for manual selection of electrodes and parameter values, and a field view for manipulation of stimulation field size, position or shape followed by automatic programming of electrode combination and parameter values to approximate the desired stimulation field. The stimulation field may be defined by the selected stimulation parameters in the electrode view or by outlining and defining the stimulation field first. The stimulation field may be manipulated by a variety of input media, including soft keys, touchscreen keys, hard keys, scroll wheels, touchpad's, joysticks, a mouse, a trackball, or other devices.

In general, such input devices may be used to provide different viewing perspectives (side, cross-sectional, concentric axial, and unwrapped 2D array) of a lead with complex electrode array geometry, and permit rotation of the perspective views to observe sides of the lead that may not be visible in a single two-dimensional side view. Other perspective view, independent or in conjunction with axial and cross-sectional views, are possible. Fore example, skewed views looking down the length of the lead from above are possible. In addition, views showing both sides of a lead are possible.

The disclosure also contemplates computer-readable media comprising instructions to cause a processor to perform any of the functions described herein. The computer-readable media may take the form of any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Various embodiments of the invention have been described. These and other embodiments are within the scope of the following claims.

The invention claimed is:

1. A method comprising:
presenting on a display at least one view of a representation of an implantable lead having a complex electrode array geometry;
receiving user input defining a stimulation field on the representation of the lead;
selecting at least one predefined volumetric stimulation template from a memory based on the stimulation field, wherein the at least one volumetric stimulation template is stored in the memory prior to receiving user input defining the stimulation field; and
selecting an electrical stimulation parameter set associated with the selected volumetric stimulation template in the memory.

2. The method of claim 1, further comprising communicating the electrical stimulation parameter set to an electrical stimulator.

3. The method of claim 1, further comprising delivering electrical stimulation therapy to a patient according to the electrical stimulation parameter set.

4. The method of claim 1, further comprising:
generating at least one volumetric stimulation template for each electrode of an electrical stimulation lead based upon at least one of modeled data and experimental data; and
storing the generated volumetric stimulation templates in the memory for selection based on the stimulation field.

5. The method of claim 1, wherein selecting at least one volumetric stimulation template comprises selecting the volumetric stimulation template based on a comparison of at least one of the volumes and shapes of the volumetric stimulation template and the user-defined stimulation field.

6. The method of claim 1, wherein selecting at least one volumetric stimulation template comprises selecting a volumetric stimulation template that fills at least a portion of the stimulation field without covering any portion of the anatomical region not included in the stimulation field.

7. The method of claim 1, wherein selecting at least one volumetric stimulation template comprises selecting a volumetric stimulation template that fills at least the entire stimulation field.

8. The method of claim 1, further comprising presenting a message to the user when the stimulation template set fails to match the stimulation field by an error that is greater than a predetermined error threshold.

9. The method of claim 1, wherein presenting on a display at least one view of a representation of an implantable lead comprises presenting on the display a side view and a cross-sectional view of the representation of the lead.

10. The method of claim 1, presenting on a display at least one view of a representation of an implantable lead comprises presenting on the display a side view and a concentric axial view of the representation of the lead.

11. The method of claim 1, wherein presenting on a display at least one view of a representation of an implantable lead comprises presenting on a display an unwrapped two-dimensional array view of the representation of the lead.

12. The method of claim 1, wherein receiving user input defining a stimulation field on the representation of the lead comprises receiving user input drawing the stimulation field on the representation of the lead.

13. The method of claim 1, wherein receiving user input defining a stimulation field on the representation of the lead comprises:
presenting a representation of the stimulation field on the representation of the lead; and
receiving user input modifying the representation of the stimulation field.

14. The method of claim 1, further comprising adjusting the at least one volumetric stimulation template based on the stimulation field.

15. A system comprising:
a user interface that displays at least one view of a representation of an implantable lead having a complex electrode array geometry, and receives user input defining at least one stimulation field on the representation of the lead;
a memory that stores a plurality of predefined volumetric stimulation templates prior to the user interface receiving user input defining the at least one stimulation field; and
a processor that selects at least one of the plurality of predefined volumetric stimulation templates based on the at least one user-defined stimulation field, and selects an electrical stimulation parameter set associated with the selected volumetric stimulation template in the memory.

16. The system of claim 15, further comprising a medical device, wherein the processor controls the medical device to deliver electrical stimulation therapy to the patient according to the selected electrical stimulation parameter set.

17. The system of claim 15, wherein the processor selects the volumetric stimulation template based on a comparison of at least one of the volumes and shapes of the volumetric stimulation template and the user-defined stimulation field.

18. The system of claim 15, wherein the processor selects the volumetric stimulation template based on a determination that the template fills at least a portion of the stimulation field without covering any portion of the anatomical region not included in the stimulation field.

19. The system of claim 15, wherein the processor selects the one or more volumetric stimulation templates based on a determination that the templates fill at least the entire stimulation field.

20. The system of claim 15, wherein the user interface presents a side view and a cross-sectional view of the representation of the lead.

21. The system of claim 15, wherein the user interface presents a side view of and a concentric axial view of the representation of the lead.

22. The system of claim 15, wherein the user interface presents an unwrapped two-dimensional array view of the representation of the lead.

23. The system of claim 15, wherein the user interface receives a drawing of the stimulation field on the representation of the lead.

24. The system of claim 15, wherein the user interface presents a representation of the stimulation field one the representation of the lead, and receives user input modifying the representation of the stimulation field.

25. The system of claim 15, wherein the processor adjusts the at least one of the plurality of volumetric stimulation template based on the stimulation field.

26. The system of claim 15, wherein the user interface comprises at least one of a touchscreen and a pointing device.

27. The system of claim 15, wherein the programmer comprises at least one of a patient programmer or a clinician programmer.

28. The system of claim 15, further comprising a programmer that comprises the user interface, the memory, and the processor.

29. A computer-readable medium comprising instructions that cause a processor to:
present on a display at least one view of a representation of an implantable lead having a complex electrode array geometry;
receive user input defining a stimulation field on the representation of the lead;
select at least one predefined volumetric stimulation template from a memory based on the stimulation field, wherein the at least one volumetric stimulation template is stored in the memory prior to receiving user input defining the stimulation field; and
select an electrical stimulation parameter set associated with the selected volumetric stimulation template in the memory.

30. The computer-readable medium of claim 29, wherein the instructions that cause a processor to select at least one volumetric stimulation template comprise instructions that cause a processor to select the volumetric stimulation template based on a comparison of at least one of the volumes and shapes of the volumetric stimulation template and the user-defined stimulation field.

31. The computer-readable medium of claim 29, wherein the instructions that cause a processor to select at least one volumetric stimulation template comprise instructions that cause a processor to select a volumetric stimulation template that fills at least a portion of the stimulation field without covering any portion of the anatomical region not included in the stimulation field.

32. The computer-readable medium of claim 29, wherein the instructions that cause a processor to select at least one volumetric stimulation template comprise instructions that cause a processor to select a volumetric stimulation template that fills at least the entire stimulation field.

33. The computer-readable medium of claim 29, further comprising instructions that cause a processor to present a message to the user when the stimulation template set fails to match the stimulation field by an error that is greater than a predetermined error threshold.

34. The computer-readable medium of claim 29, further comprising instructions that cause the processor to adjust the at least one volumetric stimulation template based on the stimulation field.

* * * * *